US011844834B2

(12) United States Patent
Seo et al.

(10) Patent No.: US 11,844,834 B2
(45) Date of Patent: Dec. 19, 2023

(54) VACCINE ADJUVANT

(71) Applicant: SL VAXIGEN, INC., Seongnam-si (KR)

(72) Inventors: Yong Bok Seo, Seoul (KR); Youngwoo Choi, Seoul (KR); Sang Hee Sim, Seongnam-si (KR)

(73) Assignee: SL VAXIGEN, INC., Seongnam-si (KR)

(*) Notice: Subject to any disclaimer, the term of this patent is extended or adjusted under 35 U.S.C. 154(b) by 0 days.

(21) Appl. No.: 16/966,726

(22) PCT Filed: Jan. 30, 2019

(86) PCT No.: PCT/KR2019/001262
§ 371 (c)(1),
(2) Date: Jul. 31, 2020

(87) PCT Pub. No.: WO2019/151759
PCT Pub. Date: Aug. 8, 2019

(65) Prior Publication Data
US 2020/0360514 A1 Nov. 19, 2020

(30) Foreign Application Priority Data
Feb. 2, 2018 (KR) ........................ 10-2018-0013329

(51) Int. Cl.
*A61K 39/29* (2006.01)
*A61K 39/39* (2006.01)
*A61P 35/00* (2006.01)
*A61K 39/00* (2006.01)

(52) U.S. Cl.
CPC ............ *A61K 39/39* (2013.01); *A61K 39/292* (2013.01); *A61P 35/00* (2018.01); *A61K 2039/55538* (2013.01)

(58) Field of Classification Search
CPC .......... A61K 45/06; A61K 2039/55538; A61K 2039/55522; A61K 2039/55527; A61K 39/12; A61K 2039/53; A61K 2300/00; A61K 38/208; A61P 37/04; A61P 37/02; A61P 37/06; C07K 14/5434; C07K 14/54; C07K 16/244; C07K 14/7155; C07K 14/7158; C07K 14/523; C07K 14/005; C12N 2502/1157; C12Q 2600/106
See application file for complete search history.

(56) References Cited

U.S. PATENT DOCUMENTS 5,571,515 A 11/1996 Scott et al.
6,811,773 B1 * 11/2004 Gentz .................... C07K 1/113 514/21.3
10,201,592 B2 * 2/2019 Wong ..................... A61K 35/28
10,993,967 B2 * 5/2021 Lu ........................ C12N 5/0668
11,103,555 B2 * 8/2021 Wong ................. A61K 38/4873
11,464,806 B2 * 10/2022 Günther .................. A61P 35/00
2012/0258126 A1 10/2012 Scholler

FOREIGN PATENT DOCUMENTS

CN 102123732 A 7/2011
JP 2017-525364 A 9/2017
KR 10-0399728 B 9/2003
KR 10-2013-0116079 A 10/2013
KR 10-2013-7025903 A 10/2013
KR 10-2017-0045254 A 4/2017
KR 10-2017-0062467 A 6/2017
WO 96/33739 A1 10/1996
WO 03/103589 A2 12/2003
WO 2014/151279 A1 9/2014
WO 2016/026854 A2 2/2016
WO 2016/054003 A1 4/2016
WO 2019/151760 A1 8/2019

OTHER PUBLICATIONS

Li et al., "Characterization of Antibody Responses Elicited by Human Immunodeficiency Virus Type 1 Primary Isolate Trimeric and Monomeric Envelope Glycoproteins in Selected Adjuvants" J Virol., 2006, vol. 80, No. 3, pp. 1414-1426.
Ott et al., "MF59 Design and Evaluation of a Safe and Potent Adjuvant for Human Vaccines", Pharm Biotechnol., 1995; vol. 6, pp. 277-296, Abstract Only.
Tian et al., "IL-21 and IL-12 Inhibit Differentiation of Treg and TH17 Cells and Enhance Cytotoxicity of Peripheral Blood Mononuclear Cells in Patients with Cervical Cancer", Int J Gynecol Cancer, 2011, vol. 21, pp. 1672-1678.
NCBI, Genbank Accession No. XP_004037971.1, 'Predicted: interleukin-12 subunit alpha [Gorilla gorilla gorilla], Nov. 4, 2016, EAW61576.1, 'interleukin 12B (natural killer cell stimulatory factor 2, cytotoxic lymphocyte maturation factor 2, p40) [*Homo sapiens*]', Mar. 23, 2015, XP_012328409.1, 'interleukin-21 [*Aotus nancymaae*]', Jun. 28, 2017, XP_004041964.1, Predicted: C-C motif chemokine 3 [Gorilla gorilla gorilla]', Nov. 4, 2016.
Tatsumi et al. "Disease-associated Bias in T Helper Type 1 (Th1)/Th2 CD4+ T Cell Responses Against MAGE-6 in HLA-DRB1*0401+ Patients With Renal Cell Carcinoma or Melanoma", J. Exp. Med. 196(5) 619-628, 2002.

(Continued)

*Primary Examiner* — Bao Q Li

(74) *Attorney, Agent, or Firm* — Vorys, Sater, Seymour and Pease LLP; Mih Suhn Koh

(57) ABSTRACT

There is provided a novel vaccine adjuvant, and more specifically, a vaccine adjuvant for stimulating a T lymphocyte-specific immune response, which includes an IL-12 protein and an IL-21 protein as active ingredients, or includes the polynucleotide encoding an IL-12 protein and the polynucleotide encoding an IL-21 protein as active ingredients.

15 Claims, 13 Drawing Sheets

Specification includes a Sequence Listing.

(56) References Cited

OTHER PUBLICATIONS

Charron et al., "Neuron Specificity of the Neurofilament Light Promoter in Transgenic Mice Requires the Presence of DNA Unwinding Elements", J. Biol. Chem. 1995, 270: 25739-25745.
Pagano et al., "Association of cdk2 Kinase with the Transcription Factor E2F During S Phase", (1992) Science 255, 1144-1147.
Gyuris et al., "Cdi1, a Human G1 and S Phase Protein Phosphatase That Associates with Cdk2", (1995) Cell 75, 791-803.
Dou et al., "Comparison of Immune Responses Induced in Mice by Vaccination with DNA Vaccine Constructs Expressing Mycobacterial Antigen 85A and Interleukin-21 and Bacillus Galmette-Guerin", Immunological Investigations, 2008, vol. 37, pp. 113-127.
Ferrone et al., "Adjuvanticity of Plasmid DNA Encoding Cytokines Fused to Immunoglobulin Fc Domains", Clinical Cancer Research, 2006, vol. 12, No. 18, pp. 5511-5519.
Kishida et al., "Interleukin (IL)-21 and IL-15 Genetic Transfer Synergistically Augments Therapeutic Antitumor Immunity and Promotes Regression of Metastatic Lymphoma", Molecular Therapy, 2003, vol. 8, No. 4, pp. 552-558.

* cited by examiner pCMV
IL-12p35
IRES
IL-12p40
pRSV
IL-21

FIG. 2

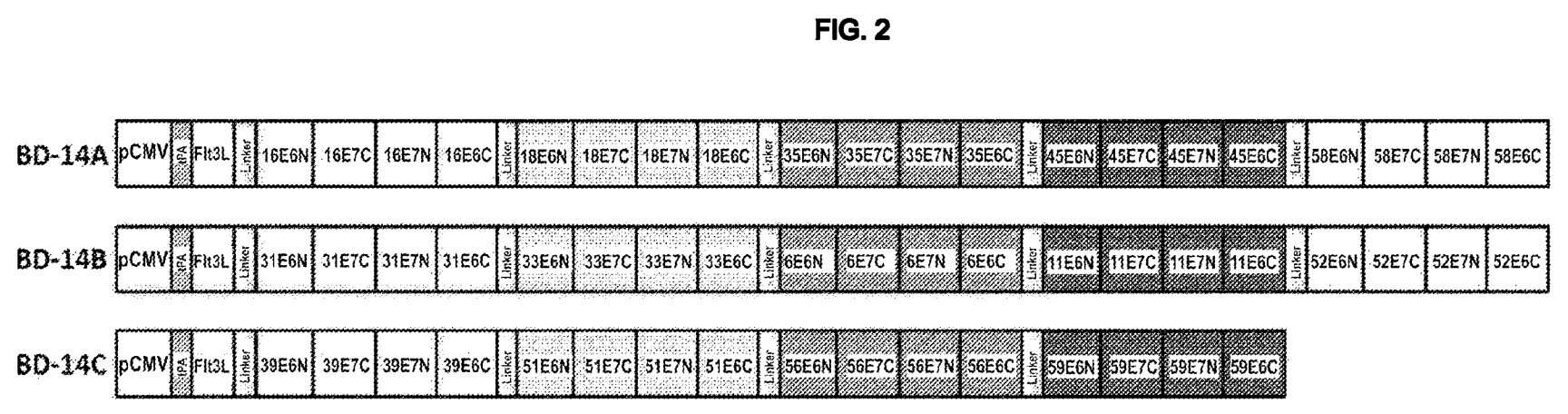

BD-14A: pCMV | tPA | Flt3L | Linker | 16E6N | 16E7C | 16E7N | 16E6C | Linker | 18E6N | 18E7C | 18E7N | 18E6C | Linker | 35E6N | 35E7C | 35E7N | 35E6C | Linker | 45E6N | 45E7C | 45E7N | 45E6C | Linker | 58E6N | 58E7C | 58E7N | 58E6C BD-14B: pCMV | tPA | Flt3L | Linker | 31E6N | 31E7C | 31E7N | 31E6C | Linker | 33E6N | 33E7C | 33E7N | 33E6C | Linker | 6E6N | 6E7C | 6E7N | 6E6C | Linker | 11E6N | 11E7C | 11E7N | 11E6C | Linker | 52E6N | 52E7C | 52E7N | 52E6C BD-14C: pCMV | tPA | Flt3L | Linker | 39E6N | 39E7C | 39E7N | 39E6C | Linker | 51E6N | 51E7C | 51E7N | 51E6C | Linker | 56E6N | 56E7C | 56E7N | 56E6C | Linker | 59E6N | 59E7C | 59E7N | 59E6C FIG. 3
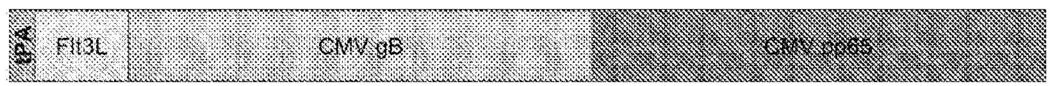
FIG. 4a
tPA-Flt3L-gB-UL39
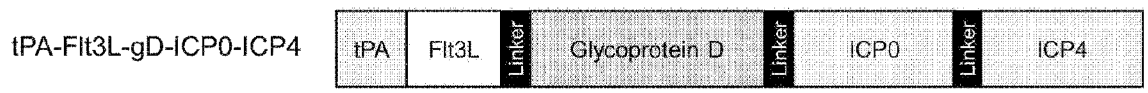
FIG. 4b
tPA-Flt3L-gD-ICP0-ICP4
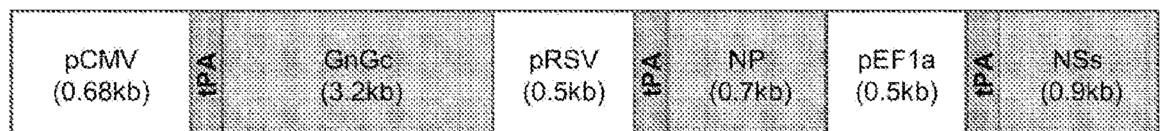
FIG. 5
| pCMV (0.68kb) | tPA | GnGc (3.2kb) | pRSV (0.5kb) | tPA | NP (0.7kb) | pEF1a (0.5kb) | tPA | NSs (0.9kb) |
|---|---|---|---|---|---|---|---|---|
FIG. 6
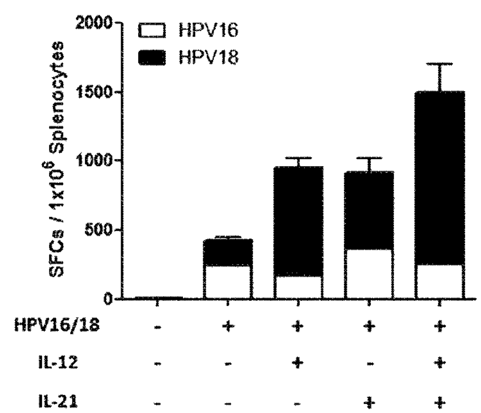

FIG. 12a
EP (I.M) C57BL/6
-28 -14 -7 0 day
Vaccination Depo-provera (2mg)
HSV-2 infection
FIG. 12b
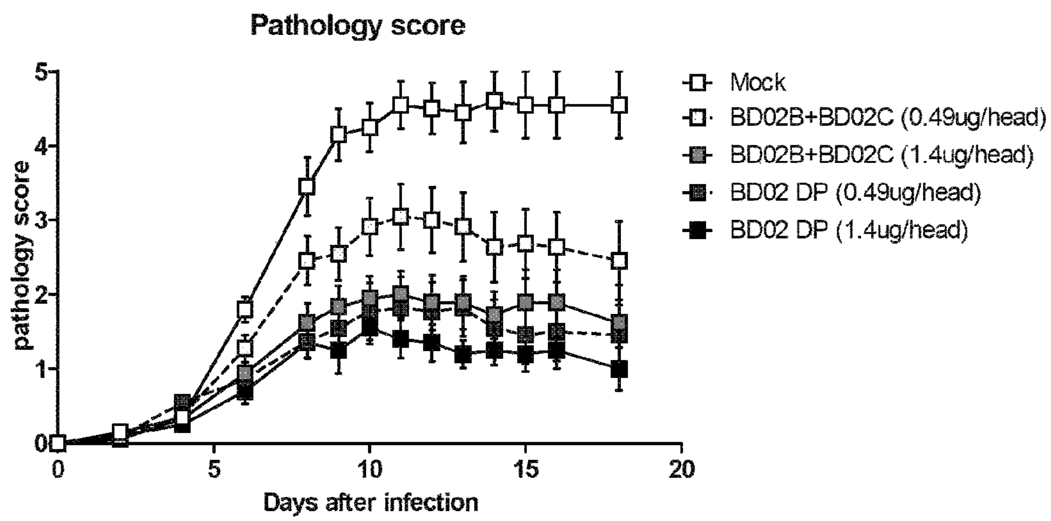
FIG. 12c
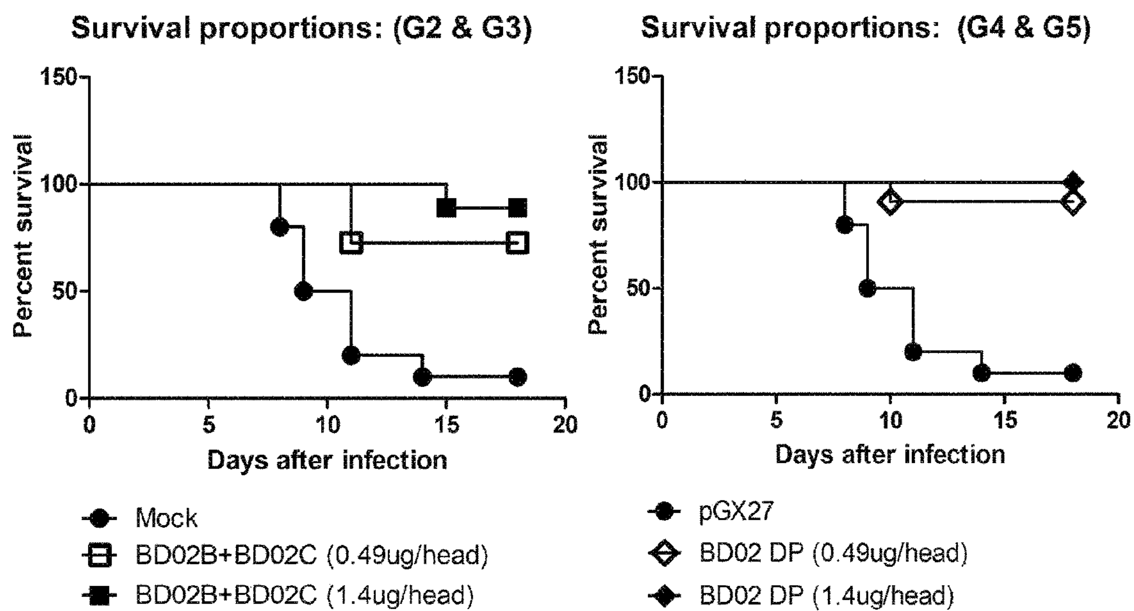

SEQUENCE LISTING

```
<160> NUMBER OF SEQ ID NOS: 68

<210> SEQ ID NO 1
<211> LENGTH: 253
<212> TYPE: PRT
<213> ORGANISM: Homo sapiens

<400> SEQUENCE: 1

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160
```

```
Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250


<210> SEQ ID NO 2
<211> LENGTH: 328
<212> TYPE: PRT
<213> ORGANISM: Homo sapiens

<400> SEQUENCE: 2

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285
```

```
Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 3
<211> LENGTH: 155
<212> TYPE: PRT
<213> ORGANISM: Homo sapiens

<400> SEQUENCE: 3

Met Glu Arg Ile Val Ile Cys Leu Met Val Ile Phe Leu Gly Thr Leu
1               5                   10                  15

Val His Lys Ser Ser Ser Gln Gly Gln Asp Arg His Met Ile Arg Met
            20                  25                  30

Arg Gln Leu Ile Asp Ile Val Asp Gln Leu Lys Asn Tyr Val Asn Asp
        35                  40                  45

Leu Val Pro Glu Phe Leu Pro Ala Pro Glu Asp Val Glu Thr Asn Cys
    50                  55                  60

Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
        115                 120                 125

Phe Leu Glu Arg Phe Lys Ser Leu Leu Gln Lys Met Ile His Gln His
    130                 135                 140

Leu Ser Ser Arg Thr His Gly Ser Glu Asp Ser
145                 150                 155


<210> SEQ ID NO 4
<211> LENGTH: 759
<212> TYPE: DNA
<213> ORGANISM: Homo sapiens

<400> SEQUENCE: 4

atgtggcccc ctgggtcagc ctcccagcca ccgccctcac ctgccgcggc cacaggtctg      60

catccagcgg ctcgccctgt gtccctgcag tgccggctca gcatgtgtcc agcgcgcagc     120

ctcctccttg tggctaccct ggtcctcctg gaccacctca gtttggccag aaacctcccc     180

gtggccactc cagacccagg aatgttccca tgccttcacc actcccaaaa cctgctgagg     240

gccgtcagca acatgctcca gaaggccaga caaactctgg aattttaccc ttgcacttct     300

gaagagattg atcatgaaga tatcacaaaa gataaaacga gcacagtgga ggcctgttta     360

ccattggaat taaccaagaa tgagagttgc ctaaattcca gagagacctc tttcataact     420

aatgggagtt gcctggcctc cagaaagacc tcttttatga tggccctgtg ccttagtagt     480

atttatgaag acttgaagat gtaccaggtg gagttcaaga ccatgaatgc aaagcttctg     540

atggatccta agaggcagat ctttctggat caaaacatgc tggcagttat tgatgagctg     600

atgcaggccc tgaatttcaa cagtgagact gtgccacaaa aatcctccct tgaagaaccg     660

gatttttata aaactaaaat caagctctgc atacttcttc atgctttcag gattcgggca     720
```

gtgactattg atagagtgat gagctatctg aatgcttcc 759

<210> SEQ ID NO 5
<211> LENGTH: 987
<212> TYPE: DNA
<213> ORGANISM: Homo sapiens

<400> SEQUENCE: 5
atgtgccacc agcagctggt catcagctgg ttctccctgg tctttctggc ttctcctctg 60
gtggcaattt gggagctgaa gaaagacgtg tacgtggtcg aactggactg gtatccagat 120
gcccccggag agatggtggt cctgacctgc gacacaccag aggaagatgg catcacttgg 180
accctggacc agagctccga ggtcctggga agcggcaaga cactgactat tcaggtgaaa 240
gaattcgggg atgctggaca gtacacatgt cataagggcg gggaggtgct gtcccactct 300
ctgctgctgc tgcataagaa agaagatggc atctggtcta ctgacattct gaaggatcag 360
aaagagccca agaacaaaac cttcctgaga tgcgaagcca agaattatag cgggaggttt 420
acctgttggt ggctgaccac aatctctact gacctgacct ttagtgtgaa gtctagtagg 480
gggtcaagcg atcctcaggg agtgacctgc ggagcagcta cactgagcgc agagcgggtc 540
agaggagaca acaaggagta cgaatattcc gtggagtgcc aggaagattc tgcatgtccc 600
gcagccgagg aatccctgcc tatcgaagtg atggtggacg ccgtgcacaa gctgaaatac 660
gaaaactaca catcctcttt ctttatccgg gacatcatta agccagatcc ccctaaaaac 720
ctgcagctga agcccctgaa aaattcacga caggtggagg tcagctggga ataccctgat 780
acatggagca ctccacattc ttatttcagt ctgacttttt gcgtgcaggt ccagggcaag 840
agtaaacgag agaagaaaga ccgggtcttc accgataaga catccgctac tgtgatctgt 900
cggaaaaacg ccagtatttc agtgagggct caggaccgct actatagttc aagctggtca 960
gagtgggcaa gcgtgccctg ttcctag 987

<210> SEQ ID NO 6
<211> LENGTH: 579
<212> TYPE: DNA
<213> ORGANISM: Artificial Sequence
<220> FEATURE:
<223> OTHER INFORMATION: ECMV IRES

<400> SEQUENCE: 6
cccctctccc tcccccccc ctaacgttac tggccgaagc cgcttggaat aaggccggtg 60
tgcgtttgtc tatatgttat tttccaccat attgccgtct tttggcaatg tgagggcccg 120
gaaacctggc cctgtcttct tgacgagcat tcctaggggt ctttcccctc tcgccaaagg 180
aatgcaaggt ctgttgaatg tcgtgaagga agcagttcct ctggaagctt cttgaagaca 240
aacaacgtct gtagcgaccc tttgcaggca gcggaacccc ccacctggcg acaggtgcct 300
ctgcggccaa aagccacgtg tataagatac acctgcaaag gcggcacaac cccagtgcca 360
cgttgtgagt tggatagttg tggaaagagt caaatggctc tcctcaagcg tattcaacaa 420
ggggctgaag gatgcccaga aggtacccca ttgtatggga tctgatctgg ggcctcggtg 480
cacatgcttt acatgtgttt agtcgaggtt aaaaaaacgt ctaggccccc cgaaccacgg 540
ggacgtggtt ttcctttgaa aaacacgatg ataatatgg 579

<210> SEQ ID NO 7
<211> LENGTH: 527
<212> TYPE: DNA

<213> ORGANISM: Artificial Sequence
<220> FEATURE:
<223> OTHER INFORMATION: RSV promoter

<400> SEQUENCE: 7

```
ctgctccctg cttgtgtgtt ggaggtcgct gagtagtgcg cgagcaaaat ttaagctaca     60

acaaggcaag gcttgaccga caattgcatg aagaatctgc ttagggttag gcgttttgcg    120

ctgcttcgcg atgtacgggc cagatatacg cgtatctgag gggactaggg tgtgtttagg    180

cgaaaagcgg ggcttcggtt gtacgcggtt aggagtcccc tcaggatata gtagtttcgc    240

ttttgcatag ggagggggaa atgtagtctt atgcaatact cttgtagtct tgcaacatgg    300

taacgatgag ttagcaacat gccttacaag gagagaaaaa gcaccgtgca tgccgattgg    360

tggaagtaag gtggtacgat cgtgccttat taggaaggca acagacgggt ctgacatgga    420

ttggacgaac cactgaattc cgcattgcag agatattgta tttaagtgcc tagctcgata    480

caataaacgc catttgacca ttcaccacat tggtgtgcac ctccaag                  527
```

<210> SEQ ID NO 8
<211> LENGTH: 468
<212> TYPE: DNA
<213> ORGANISM: Homo sapiens

<400> SEQUENCE: 8

```
atggaacgga ttgtcatttg cctgatggtc atttttctgg gaaccctggt ccacaagtca     60

agcagtcagg gccaggatag gcacatgatt aggatgcgcc agctgatcga cattgtggat    120

cagctgaaga actacgtgaa tgacctggtc cctgagtttc tgcctgcacc agaggatgtc    180

gaaacaaact gcgaatggag cgccttctcc tgttttcaga aggcccagct gaaatccgct    240

aacaccggca acaatgagcg aatcatcaac gtgagcatca agaagctgaa gcggaaaccc    300

cctagcacta atgctgggcg gagacagaaa catagactga cctgcccctc ttgtgacagt    360

tatgaaaaga aaccacccaa ggagttcctg gaacgcttta aaagtctgct gcagaaaatg    420

attcaccagc acctgtcctc cagaactcac gggtccgaag attcctaa                 468
```

<210> SEQ ID NO 9
<211> LENGTH: 1189
<212> TYPE: DNA
<213> ORGANISM: Artificial Sequence
<220> FEATURE:
<223> OTHER INFORMATION: hEF-1alpha promoter

<400> SEQUENCE: 9

```
cgtgaggctc cggtgcccgt cagtgggcag agcgcacatc gcccacagtc cccgagaagt     60

tggggggagg ggtcggcaat tgaaccggtg cctagagaag gtggcgcggg gtaaactggg    120

aaagtgatgt cgtgtactgg ctccgccttt ttcccgaggg tgggggagaa ccgtatataa    180

gtgcagtagt cgccgtgaac gttctttttc gcaacgggtt tgccgccaga acacaggtaa    240

gtgccgtgtg tggttcccgc gggcctggcc tctttacggg ttatggccct tgcgtgcctt    300

gaattacttc cacgcccctg gctgcagtac gtgattcttg atcccgagct tcgggttgga    360

agtgggtggg agagttcgag gccttgcgct taaggagccc cttcgcctcg tgcttgagtt    420

gaggcctggc ctgggcgctg gggccgccgc gtgcgaatct ggtggcacct tcgcgcctgt    480

ctcgctgctt tcgataagtc tctagccatt taaaattttt gatgacctgc tgcgacgctt    540

tttttctggc aagatagtct tgtaaatgcg ggccaagatc tgcacactgg tatttcggtt    600

tttggggccg cgggcggcga cggggcccgt gcgtcccagc gcacatgttc ggcgaggcgg    660
```

```
ggcctgcgag cgcggccacc gagaatcgga cgggggtagt ctcaagctgg ccggcctgct     720

ctggtgcctg gcctcgcgcc gccgtgtatc gccccgccct gggcggcaag gctggcccgg     780

tcggcaccag ttgcgtgagc ggaaagatgg ccgcttcccg gccctgctgc agggagctca     840

aaatggagga cgcggcgctc gggagagcgg gcgggtgagt cacccacaca aaggaaaagg     900

gcctttccgt cctcagccgt cgcttcatgt gactccacgg agtaccgggc gccgtccagg     960

cacctcgatt agttctcgag cttttggagt acgtcgtctt taggttgggg ggaggggttt    1020

tatgcgatgg agtttcccca cactgagtgg gtggagactg aagttaggcc agcttggcac    1080

ttgatgtaat tctccttgga atttgccctt tttgagtttg gatcttggtt cattctcaag    1140

cctcagacag tggttcaaag ttttttctt ccatttcagg tgtcgtgaa                1189
```

<210> SEQ ID NO 10
<211> LENGTH: 92
<212> TYPE: PRT
<213> ORGANISM: Homo sapiens

<400> SEQUENCE: 10

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

<210> SEQ ID NO 11
<211> LENGTH: 279
<212> TYPE: DNA
<213> ORGANISM: Homo sapiens

<400> SEQUENCE: 11

```
atgcaggtgt caaccgccgc cctggctgtc ctgctgtgca ctatggctct gtgcaatcag      60

ttttccgcaa gtctggccgc tgatactccc accgcctgct gtttctctta cacaagtagg     120

cagatccctc agaacttcat tgctgactat tttgagacta gctcccagtg cagcaagccc     180

ggcgtgatct ttctgaccaa gcggagccgg caggtctgtg ccgatccctc cgaagaatgg     240

gtgcagaagt atgtctccga cctggaactg tcagcataa                           279
```

<210> SEQ ID NO 12
<211> LENGTH: 215
<212> TYPE: PRT
<213> ORGANISM: Mus musculus

<400> SEQUENCE: 12

```
Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45
```

```
Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215


<210> SEQ ID NO 13
<211> LENGTH: 335
<212> TYPE: PRT
<213> ORGANISM: Mus musculus

<400> SEQUENCE: 13

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
```

```
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335
```

<210> SEQ ID NO 14
<211> LENGTH: 648
<212> TYPE: DNA
<213> ORGANISM: Mus musculus

<400> SEQUENCE: 14

```
atgtgccaga gcagatacct gctgttcctg gccaccctgg ccctgctgaa ccacctgagc      60

ctggccagag tgatccccgt gagcggcccc gccagatgcc tgagccagag cagaaacctg     120

ctgaagacaa ccgacgacat ggtgaagacc gccagagaga agctgaagca ctacagctgc     180

accgccgagg acatcgacca cgaggacatc accagagacc agaccagcac cctgaagacc     240

tgcctgcccc tggagctgca caagaacgag agctgcctgg ccacaagaga gaccagcagc     300

accacaagag gcagctgcct gcctccccag aagaccagcc tgatgatgac cctgtgcctg     360

ggcagcatct acgaggacct gaagatgtac cagaccgagt tccaggccat caacgctgcc     420

ctgcagaacc acaatcacca gcagatcatc ctggacaagg gcatgctggt ggccatcgac     480

gagctgatgc agagcctgaa ccacaacggc gagaccctga gacagaagcc ccctgtgggc     540

gaggccgatc cctacagagt gaagatgaag ctgtgcatcc tgctgcacgc cttcagcacc     600

agagtggtga ccatcaacag agtgatgggc tacctgagca gcgcctga                  648
```

<210> SEQ ID NO 15
<211> LENGTH: 1008
<212> TYPE: DNA
<213> ORGANISM: Mus musculus

<400> SEQUENCE: 15

```
atgtgccccc agaagctgac catcagctgg ttcgccatcg tgctgctggt gagccccctg      60

atggccatgt gggagctgga gaaggacgtg tacgtggtgg aggtggactg gacccccgac     120

gcccccggcg agaccgtgaa cctgacctgc gacacccccg aggaggacga catcacctgg     180

accagcgacc agaggcacgg cgtgatcggc agcggcaaga ccctgaccat caccgtgaag     240

gagttcctgg acgccggcca gtacacctgc cacaagggcg gcgagaccct gagccacagc     300

cacctgctgc tgcacaagaa ggagaacggc atctggagca ccgagatcct gaagaacttc     360

aagaacaaga ccttcctgaa gtgcgaggcc cccaactaca gcggcaggtt cacctgcagc     420

tggctggtgc agaggaacat ggacctgaag ttcaacatca agagcagcag cagcagcccc     480
```

```
gacagcaggg ccgtgacctg cggcatggcc agcctgagcg ccgagaaggt gaccctggac    540

cagagggact acgagaagta cagcgtgagc tgccaggagg acgtgacctg ccccaccgcc    600

gaggagaccc tgcccatcga gctggccctg gaggccaggc agcagaacaa gtacgagaac    660

tacagcacca gcttcttcat cagggacatc atcaagcccg acccccccaa gaacctgcag    720

atgaagcccc tgaagaacag ccaggtggag gtgagctggg agtaccccga cagctggagc    780

accccccaca gctacttcag cctgaagttc ttcgtgagaa tccagaggaa gaaggagaag    840

atgaaggaga ccgaggaggg ctgcaaccag aagggcgcct tcctggtgga gaagaccagc    900

accgaggtgc agtgcaaggg cggcaacgtg tgcgtgcagg cccaggacag gtactacaac    960

agcagctgca gcaagtgggc ctgcgtgccc tgcagggtga ggagctaa               1008
```

```
<210> SEQ ID NO 16
<211> LENGTH: 146
<212> TYPE: PRT
<213> ORGANISM: Mus musculus

<400> SEQUENCE: 16

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145
```

```
<210> SEQ ID NO 17
<211> LENGTH: 441
<212> TYPE: DNA
<213> ORGANISM: Mus musculus

<400> SEQUENCE: 17

atggagagaa cactggtctg cctcgtggtc atcttcctgg gtactgtggc tcataaatcc     60

tcacctcagg gtcccgatag actgctgatc aggctgcggc acctcatcga cattgtggag    120

cagctcaaaa tctacgaaaa cgacctggac cccgagctgc tctctgcccc ccaggatgtc    180

aaggggcact gcgaacatgc cgctttcgca tgttttcaga aggccaaact gaagcccagc    240

aatcctggca acaataagac cttcatcatt gacctggtgg ctcagctcag gagacggctg    300

ccagcacgac gaggaggaaa gaaacagaaa catatcgcta agtgccctag ctgtgattcc    360

tatgagaaaa gaacaccaaa ggagttcctc gaaaggctca aatggctcct ccagaagatg    420
```

attcaccagc acctctccta a 441

<210> SEQ ID NO 18
<211> LENGTH: 92
<212> TYPE: PRT
<213> ORGANISM: Mus musculus

<400> SEQUENCE: 18

Met Lys Val Ser Thr Thr Ala Leu Ala Val Leu Leu Cys Thr Met Thr
1 5 10 15

Leu Cys Asn Gln Val Phe Ser Ala Pro Tyr Gly Ala Asp Thr Pro Thr
20 25 30

Ala Cys Cys Phe Ser Tyr Ser Arg Lys Ile Pro Arg Gln Phe Ile Val
35 40 45

Asp Tyr Phe Glu Thr Ser Ser Leu Cys Ser Gln Pro Gly Val Ile Phe
50 55 60

Leu Thr Lys Arg Asn Arg Gln Ile Cys Ala Asp Ser Lys Glu Thr Trp
65 70 75 80

Val Gln Glu Tyr Ile Thr Asp Leu Glu Leu Asn Ala
85 90

<210> SEQ ID NO 19
<211> LENGTH: 279
<212> TYPE: DNA
<213> ORGANISM: Mus musculus

<400> SEQUENCE: 19
atgaaggtga gcaccaccgc tctggctgtg ctgctctgca ccatgaccct ctgcaaccag 60
gtgttctcag ctccctacgg cgctgatacc cccaccgcct gctgcttcag ctacagccgg 120
aagatccccc ggcagttcat cgtggactac ttcgaaacca gcagcctgtg cagccagccc 180
ggcgtgatct tcctgaccaa acggaaccgg cagatctgcg ctgacagcaa agagacctgg 240
gtgcaggaat acatcaccga cctggaactg aacgcctaa 279

<210> SEQ ID NO 20
<211> LENGTH: 10
<212> TYPE: PRT
<213> ORGANISM: Artificial Sequence
<220> FEATURE:
<223> OTHER INFORMATION: (GS)5 linker

<400> SEQUENCE: 20

Gly Ser Gly Ser Gly Ser Gly Ser Gly Ser
1 5 10

<210> SEQ ID NO 21
<211> LENGTH: 30
<212> TYPE: DNA
<213> ORGANISM: Artificial Sequence
<220> FEATURE:
<223> OTHER INFORMATION: polynucleotide encoding (GS)5 linker

<400> SEQUENCE: 21
ggatcaggca gtggttcagg atcaggtagt 30

<210> SEQ ID NO 22
<211> LENGTH: 25
<212> TYPE: PRT
<213> ORGANISM: Artificial Sequence
<220> FEATURE:
<223> OTHER INFORMATION: tPA signal sequence

```
<400> SEQUENCE: 22

Met Asp Ala Met Lys Arg Gly Leu Cys Cys Val Leu Leu Leu Cys Gly
1               5                   10                  15

Ala Val Phe Val Ser Pro Ser His Ala
            20                  25


<210> SEQ ID NO 23
<211> LENGTH: 75
<212> TYPE: DNA
<213> ORGANISM: Artificial Sequence
<220> FEATURE:
<223> OTHER INFORMATION: polynucleotide encoding tPA signal sequence

<400> SEQUENCE: 23

atggacgcca tgaagagagg cctgtgctgc gtgctgctgc tgtgcggcgc cgtgttcgtg      60

agccccagcc acgcc                                                       75


<210> SEQ ID NO 24
<211> LENGTH: 156
<212> TYPE: PRT
<213> ORGANISM: Artificial Sequence
<220> FEATURE:
<223> OTHER INFORMATION: Flt3L_27-182

<400> SEQUENCE: 24

Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
    50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro
145                 150                 155


<210> SEQ ID NO 25
<211> LENGTH: 468
<212> TYPE: DNA
<213> ORGANISM: Artificial Sequence
<220> FEATURE:
<223> OTHER INFORMATION: polynucleotide encoding Flt3L_27-182

<400> SEQUENCE: 25

acccaggact gcagcttcca gcacagcccc atcagcagcg acttcgccgt gaagatcaga      60

gagctgagcg actacctgct gcaggactac cccgtgaccg tggccagcaa cctgcaggac     120

gaggagctgt gcggcggcct gtggagactg gtgctggccc agagatggat ggagagactg     180

aagaccgtgg ccggcagcaa gatgcagggc ctgctggaga gagtgaacac cgagatccac     240
```

```
ttcgtgacca agtgcgcctt ccagcctccc cccagctgcc tgaggttcgt gcagaccaac    300

atcagcagac tgctgcagga gaccagcgag cagctggtgg ccctgaagcc ctggatcacc    360

agacagaact tcagcagatg cctggagctg cagtgccagc ccgacagcag caccctgccc    420

cctccctgga gccccagacc cctggaggcc accgctccca cagcccct                 468


<210> SEQ ID NO 26
<211> LENGTH: 1957
<212> TYPE: PRT
<213> ORGANISM: Artificial Sequence
<220> FEATURE:
<223> OTHER INFORMATION: BD-14A polypeptide

<400> SEQUENCE: 26

Asp Ala Met Lys Arg Gly Leu Cys Cys Val Leu Leu Leu Cys Gly Ala
1               5                   10                  15

Val Phe Val Ser Pro Ser His Ala Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Ser Gly Ser Gly Ser Gly Ser Gly Ser Met Asp
            180                 185                 190

Ala Met Lys Arg Gly Leu Cys Cys Val Leu Leu Leu Cys Gly Ala Val
        195                 200                 205

Phe Val Ser Pro Ser His Ala Thr Gln Asp Cys Ser Phe Gln His Ser
    210                 215                 220

Pro Ile Ser Ser Asp Phe Ala Val Lys Ile Arg Glu Leu Ser Asp Tyr
225                 230                 235                 240

Leu Leu Gln Asp Tyr Pro Val Thr Val Ala Ser Asn Leu Gln Asp Glu
                245                 250                 255

Glu Leu Cys Gly Gly Leu Trp Arg Leu Val Leu Ala Gln Arg Trp Met
            260                 265                 270

Glu Arg Leu Lys Thr Val Ala Gly Ser Lys Met Gln Gly Leu Leu Glu
        275                 280                 285

Arg Val Asn Thr Glu Ile His Phe Val Thr Lys Cys Ala Phe Gln Pro
    290                 295                 300

Pro Pro Ser Cys Leu Arg Phe Val Gln Thr Asn Ile Ser Arg Leu Leu
305                 310                 315                 320
```

-continued

```
Gln Glu Thr Ser Glu Gln Leu Val Ala Leu Lys Pro Trp Ile Thr Arg
                325                 330                 335

Gln Asn Phe Ser Arg Cys Leu Glu Leu Gln Cys Gln Pro Asp Ser Ser
            340                 345                 350

Thr Leu Pro Pro Pro Trp Ser Pro Arg Pro Leu Glu Ala Thr Ala Pro
        355                 360                 365

Thr Ala Pro Gly Ser Gly Ser Gly Ser Gly Ser Gly Ser Met His Gln
    370                 375                 380

Lys Arg Thr Ala Met Phe Gln Asp Pro Gln Glu Arg Pro Arg Lys Leu
385                 390                 395                 400

Pro Gln Leu Cys Thr Glu Leu Gln Thr Thr Ile His Asp Ile Ile Leu
                405                 410                 415

Glu Cys Val Tyr Cys Lys Gln Gln Leu Leu Arg Arg Glu Val Tyr Asp
            420                 425                 430

Phe Ala Phe Arg Asp Leu Cys Ile Val Tyr Arg Asp Gly Asn Pro Tyr
        435                 440                 445

Ala Val Cys Asp Lys Cys Leu Lys Phe Tyr Ser Lys Ile Ser Glu Tyr
    450                 455                 460

Arg His Pro Ala Gly Gln Ala Glu Pro Asp Arg Ala His Tyr Asn Ile
465                 470                 475                 480

Val Thr Phe Cys Cys Lys Cys Asp Ser Thr Leu Arg Leu Cys Val Gln
                485                 490                 495

Ser Thr His Val Asp Ile Arg Thr Leu Glu Asp Leu Leu Met Gly Thr
            500                 505                 510

Leu Gly Ile Val Cys Pro Ile Cys Ser Gln Lys Pro Gly Ser Gly Ser
        515                 520                 525

Gly Ser Gly Ser Gly Ser Met His Gly Asp Thr Pro Thr Leu His Glu
    530                 535                 540

Tyr Met Leu Asp Leu Gln Pro Glu Thr Thr Asp Leu Tyr Cys Tyr Glu
545                 550                 555                 560

Gln Leu Asn Asp Ser Ser Glu Glu Glu Asp Glu Ile Asp Gly Pro Ala
                565                 570                 575

Gly Gln Ala Glu Pro Asp Arg Ala His Tyr Asn Ile Val Thr Phe Cys
            580                 585                 590

Cys Lys Pro Tyr Ala Val Cys Asp Lys Cys Leu Lys Phe Tyr Ser Lys
        595                 600                 605

Ile Ser Glu Tyr Arg His Tyr Cys Tyr Ser Val Tyr Gly Thr Thr Leu
    610                 615                 620

Glu Gln Gln Tyr Asn Lys Pro Leu Cys Asp Leu Leu Ile Arg Cys Ile
625                 630                 635                 640

Asn Cys Gln Lys Pro Leu Cys Pro Glu Glu Lys Gln Arg His Leu Asp
                645                 650                 655

Lys Lys Gln Arg Phe His Asn Ile Arg Gly Arg Trp Thr Gly Arg Cys
            660                 665                 670

Met Ser Cys Cys Arg Ser Ser Arg Thr Arg Arg Glu Thr Gln Leu Gly
        675                 680                 685

Ser Gly Ser Gly Ser Gly Ser Gly Ser Met Ala Arg Phe Glu Asp Pro
    690                 695                 700

Thr Arg Arg Pro Tyr Lys Leu Pro Asp Leu Cys Thr Glu Leu Asn Thr
705                 710                 715                 720

Ser Leu Gln Asp Ile Glu Ile Thr Cys Val Tyr Cys Lys Thr Val Leu
                725                 730                 735

Glu Leu Thr Glu Val Phe Glu Phe Ala Phe Lys Asp Leu Phe Val Val
```

```
            740                 745                 750

Tyr Arg Asp Ser Ile Pro His Ala Ala Cys His Lys Cys Ile Asp Phe
        755                 760                 765

Tyr Ser Arg Ile Arg Glu Leu Arg His Tyr Ser Asp Ser Val Ile Asp
    770                 775                 780

Gly Val Asn His Gln His Leu Pro Ala Arg Arg Ala Glu Pro Gln Arg
785                 790                 795                 800

His Thr Met Leu Cys Met Cys Cys Lys Cys Glu Ala Arg Ile Glu Leu
                805                 810                 815

Val Val Glu Ser Ser Ala Asp Asp Leu Arg Ala Phe Gln Gln Leu Phe
            820                 825                 830

Leu Ser Thr Leu Ser Phe Val Cys Pro Trp Cys Ala Ser Gln Gln Gly
        835                 840                 845

Ser Gly Ser Gly Ser Gly Ser Gly Ser Met Tyr Gly Pro Lys Ala Thr
    850                 855                 860

Leu Gln Asp Ile Val Leu His Leu Glu Pro Gln Asn Glu Ile Pro Val
865                 870                 875                 880

Asp Leu Leu Cys His Glu Gln Leu Ser Asp Ser Glu Glu Glu Asn Asp
                885                 890                 895

Glu Ile Asp Gly Val Asn His Gln His Leu Pro Ala Arg Arg Ala Glu
            900                 905                 910

Pro Gln Arg His Thr His Lys Cys Ile Asp Phe Tyr Ser Arg Ile Arg
        915                 920                 925

Glu Leu Arg His Tyr Ser Asp Ser Val Tyr Gly Asp Thr Leu Glu Lys
    930                 935                 940

Leu Thr Asn Thr Gly Leu Tyr Asn Leu Leu Ile Arg Cys Leu Arg Cys
945                 950                 955                 960

Gln Lys Pro Leu Asn Pro Ala Glu Lys Leu Arg His Leu Asn Glu Lys
                965                 970                 975

Arg Arg Phe His Asn Ile Ala Gly His Tyr Arg Gly Gln Cys His Ser
            980                 985                 990

Cys Cys Asn Arg Ala Arg Gln Glu Arg Leu Gln Arg Arg Arg Glu Thr
        995                 1000                1005

Gln Val Gly Ser Gly Ser Gly Ser Gly Ser Gly Ser Leu Glu Met Phe
    1010                1015                1020

Gln Asp Pro Ala Glu Arg Pro Tyr Lys Leu His Asp Leu Cys Asn Glu
1025                1030                1035                1040

Val Glu Glu Ser Ile His Glu Ile Cys Leu Asn Cys Val Tyr Cys Lys
                1045                1050                1055

Gln Glu Leu Gln Arg Ser Glu Val Tyr Asp Phe Ala Cys Tyr Asp Leu
            1060                1065                1070

Cys Ile Val Tyr Arg Glu Gly Gln Pro Tyr Gly Val Cys Met Lys Cys
        1075                1080                1085

Leu Lys Phe Tyr Ser Lys Ile Ser Glu Tyr Arg Trp Pro Ala Gly Gln
    1090                1095                1100

Ala Lys Pro Asp Thr Ser Asn Tyr Asn Ile Val Thr Ser Cys Cys Lys
1105                1110                1115                1120

Cys Glu Ala Thr Leu Arg Leu Cys Val Gln Ser Thr His Ile Asp Ile
                1125                1130                1135

Arg Lys Leu Glu Asp Leu Leu Met Gly Thr Phe Gly Ile Val Cys Pro
            1140                1145                1150

Gly Cys Ser Gln Arg Ala Gly Ser Gly Ser Gly Ser Gly Ser Gly Ser
        1155                1160                1165
```

```
Met His Gly Glu Ile Thr Thr Leu Gln Asp Tyr Val Leu Asp Leu Glu
    1170                1175                1180

Pro Glu Ala Thr Asp Leu Tyr Cys Tyr Glu Gln Leu Cys Asp Ser Ser
1185                1190                1195                1200

Glu Glu Glu Glu Asp Thr Ile Asp Gly Pro Ala Gly Gln Ala Lys Pro
                1205                1210                1215

Asp Thr Ser Asn Tyr Asn Ile Val Thr Ser Cys Cys Lys Pro Tyr Gly
            1220                1225                1230

Val Cys Met Lys Cys Leu Lys Phe Tyr Ser Lys Ile Ser Glu Tyr Arg
        1235                1240                1245

Trp Tyr Arg Tyr Ser Val Tyr Gly Glu Thr Leu Glu Lys Gln Cys Asn
    1250                1255                1260

Lys Gln Leu Cys His Leu Leu Ile Arg Cys Ile Thr Cys Gln Lys Pro
1265                1270                1275                1280

Leu Cys Pro Val Glu Lys Gln Arg His Leu Glu Glu Lys Lys Arg Phe
                1285                1290                1295

His Asn Ile Gly Gly Arg Trp Thr Gly Arg Cys Met Ser Cys Trp Lys
            1300                1305                1310

Pro Thr Arg Arg Glu Thr Glu Val Gly Ser Gly Ser Gly Ser Gly Ser
        1315                1320                1325

Gly Ser Val Glu Gly Ser Met Ala Arg Phe Asp Asp Pro Lys Gln Arg
    1330                1335                1340

Pro Tyr Lys Leu Pro Asp Leu Cys Thr Glu Leu Asn Thr Ser Leu Gln
1345                1350                1355                1360

Asp Val Ser Ile Ala Cys Val Tyr Cys Lys Ala Thr Leu Glu Arg Thr
                1365                1370                1375

Glu Val Tyr Gln Phe Ala Phe Lys Asp Leu Cys Ile Val Tyr Arg Asp
            1380                1385                1390

Cys Ile Ala Tyr Ala Ala Cys His Lys Cys Ile Asp Phe Tyr Ser Arg
        1395                1400                1405

Ile Arg Glu Leu Arg Tyr Tyr Ser Asn Ser Val Glu Ala Asp Gly Val
    1410                1415                1420

Ser His Ala Gln Leu Pro Ala Arg Arg Ala Glu Pro Gln Arg His Lys
1425                1430                1435                1440

Ile Leu Cys Val Cys Cys Lys Cys Asp Gly Arg Ile Asp Leu Thr Val
                1445                1450                1455

Glu Ser Ser Ala Asp Asp Leu Arg Thr Leu Gln Gln Leu Phe Leu Ser
            1460                1465                1470

Thr Leu Ser Phe Val Cys Pro Trp Cys Ala Thr Asn Gln Gly Ser Gly
        1475                1480                1485

Ser Gly Ser Gly Ser Gly Ser Met His Gly Pro Arg Ala Thr Leu Gln
    1490                1495                1500

Glu Ile Val Leu His Leu Glu Pro Gln Asn Glu Leu Asp Pro Val Asp
1505                1510                1515                1520

Leu Leu Cys Tyr Glu Gln Leu Ser Glu Ser Glu Glu Glu Asn Asp Glu
                1525                1530                1535

Ala Asp Gly Val Ser His Ala Gln Leu Pro Ala Arg Arg Ala Glu Pro
            1540                1545                1550

Gln Arg His His Lys Cys Ile Asp Phe Tyr Ser Arg Ile Arg Glu Leu
        1555                1560                1565

Arg Tyr Tyr Ser Asn Ser Val Tyr Gly Glu Thr Leu Glu Lys Ile Thr
    1570                1575                1580
```

```
Asn Thr Glu Leu Tyr Asn Leu Leu Ile Arg Cys Leu Arg Cys Gln Lys
1585                1590                1595                1600

Pro Leu Asn Pro Ala Glu Lys Arg Arg His Leu Lys Asp Lys Arg Arg
                1605                1610                1615

Phe His Ser Ile Ala Gly Gln Tyr Arg Gly Gln Cys Asn Thr Cys Cys
            1620                1625                1630

Asp Gln Ala Arg Gln Glu Arg Leu Arg Arg Arg Arg Glu Thr Gln Val
        1635                1640                1645

Gly Ser Gly Ser Gly Ser Gly Ser Gly Ser Met Phe Gln Asp Ala Glu
    1650                1655                1660

Glu Lys Pro Arg Thr Leu His Asp Leu Cys Gln Ala Leu Glu Thr Ser
1665                1670                1675                1680

Val His Glu Ile Glu Leu Lys Cys Val Glu Cys Lys Lys Thr Leu Gln
                1685                1690                1695

Arg Ser Glu Val Tyr Asp Phe Val Phe Ala Asp Leu Arg Ile Val Tyr
            1700                1705                1710

Arg Asp Gly Asn Pro Phe Ala Val Cys Lys Val Cys Leu Arg Leu Leu
        1715                1720                1725

Ser Lys Ile Ser Glu Tyr Arg His Tyr Asn Tyr Ser Leu Tyr Gly Arg
    1730                1735                1740

Pro Asp Gly Gln Ala Gln Pro Ala Thr Ala Asn Tyr Tyr Ile Val Thr
1745                1750                1755                1760

Cys Cys Tyr Thr Cys Asp Thr Thr Val Arg Leu Cys Ile Asn Ser Thr
                1765                1770                1775

Thr Thr Asp Val Arg Thr Leu Gln Gln Leu Leu Met Gly Thr Cys Thr
            1780                1785                1790

Ile Val Cys Pro Ser Cys Ala Gln Gln Gly Ser Gly Ser Gly Ser Gly
        1795                1800                1805

Ser Gly Ser Met Arg Gly Asn Asn Pro Thr Leu Arg Glu Tyr Ile Leu
    1810                1815                1820

Asp Leu His Pro Glu Pro Thr Asp Leu Phe Cys Tyr Glu Gln Leu Cys
1825                1830                1835                1840

Asp Ser Ser Asp Glu Asp Glu Ile Gly Leu Asp Arg Pro Asp Gly Gln
                1845                1850                1855

Ala Gln Pro Ala Thr Ala Asn Tyr Tyr Ile Val Thr Cys Cys Tyr Cys
            1860                1865                1870

Leu Arg Leu Leu Ser Lys Ile Ser Glu Tyr Arg His Tyr Asn Tyr Ser
        1875                1880                1885

Leu Tyr Gly Asp Thr Leu Glu Gln Thr Leu Lys Lys Cys Leu Asn Glu
    1890                1895                1900

Ile Leu Ile Arg Cys Ile Ile Cys Gln Arg Pro Leu Cys Pro Gln Glu
1905                1910                1915                1920

Lys Lys Arg His Val Asp Leu Asn Lys Arg Phe His Asn Ile Ser Gly
                1925                1930                1935

Arg Trp Thr Gly Arg Cys Ala Val Cys Trp Arg Pro Arg Arg Arg Gln
            1940                1945                1950

Thr Gln Val Gly Ser
        1955
```

<210> SEQ ID NO 27
<211> LENGTH: 5304
<212> TYPE: DNA
<213> ORGANISM: Artificial Sequence
<220> FEATURE:
<223> OTHER INFORMATION: polynucleotide encoding BD-14A polypeptide

<400> SEQUENCE: 27

```
atggacgcca tgaagagagg cctgtgctgc gtgctgctgc tgtgcggcgc cgtgttcgtg     60
agccccagcc acgccaccca ggactgcagc ttccagcaca gccccatcag cagcgacttc    120
gccgtgaaga tcagagagct gagcgactac ctgctgcagg actaccccgt gaccgtggcc    180
agcaacctgc aggacgagga gctgtgcggc ggcctgtgga gactggtgct ggcccagaga    240
tggatggaga gactgaagac cgtggccggc agcaagatgc agggcctgct ggagagagtg    300
aacaccgaga tccacttcgt gaccaagtgc gccttccagc ctccccccag ctgcctgagg    360
ttcgtgcaga ccaacatcag cagactgctg caggagacca gcgagcagct ggtggccctg    420
aagccctgga tcaccagaca gaacttcagc agatgcctgg agctgcagtg ccagcccgac    480
agcagcaccc tgcccccctcc ctggagcccc agacccctgg aggccaccgc tcccacagcc    540
cctggcagcg ggtccggaag tgggtctgga tctatgcacc agaagagaac cgccatgttc    600
caggaccccc aggagagacc cagaaagctg ccccagctgt gcaccgagct gcagaccaca    660
atccacgaca tcatcctgga gtgcgtgtac tgcaagcagc agctgctgag aagagaggtg    720
tacgacttcg ccttcagaga cctgtgcatc gtgtacagag atggcaaccc ttatgctgtc    780
tgtgataaat gtctcaaatt ttattccaaa attagtgaat ataggcatcc agcaggacag    840
gctgaaccag atagggctca ttataatatt gtcacatttt gttgtaaatg cgacagcacc    900
ctgagactgt gcgtgcagag cacccacgtg gacatcagaa ccctggagga cctgctgatg    960
ggcaccctgg gcatcgtgtg ccccatctgc agccagaagc ctggcagcgg ctctggctcc   1020
ggcagtggct caatgcacgg cgacacaccc accctgcacg agtacatgct ggacctgcag   1080
cccgagacta ccgacctgta ctgctacgag cagctgaacg acagcagcga ggaagaggac   1140
gagatcgacg gccctgctgg ccaggccgag cccgacagag cccactacaa catcgtgacc   1200
ttctgctgca agccctacgc cgtgtgcgac aagtgcctga agttctacag caagatcagc   1260
gagtacagac actactgcta cagcgtgtac ggcaccaccc tggagcagca gtacaacaag   1320
cccctgtgcg acctgctgat cagatgcatc aactgccaga agcccctgtg ccccgaggag   1380
aagcagagac acctggacaa gaagcagaga ttccacaaca tcagaggcag atggaccggc   1440
agatgcatga gctgctgcag aagcagcaga accagaagag agacccagct gggatctggc   1500
agtggatctg gaagcggctc tatggccaga ttcgaagatc ccaccagaag accctacaag   1560
ctgcccgacc tgtgcaccga gctgaacacc agcctgcagg acatcgagat cacctgcgtg   1620
tactgcaaga ccgtgctgga gctgaccgag gtgttcgagt tcgccttcaa ggacctgttc   1680
gtggtgtaca gagacagcat cccccacgct gcctgccata aatgtattga tttttattcc   1740
aggattaggg aactcaggca ttatagtgat tctgtcattg atggtgtcaa tcatcagcat   1800
ctcccagcta ggagggctga acctcagagg cataccatgc tgtgcatgtg ctgcaagtgc   1860
gaggccagaa tcgagctggt ggtggagagc agcgccgacg acctgagagc cttccagcag   1920
ctgttcctga gcaccctgag cttcgtgtgc ccctggtgcg ccagccagca gggctcagga   1980
tctggcagcg gaagtggatc tatgtacggc cccaaggcta ccctgcagga catcgtgctg   2040
cacctggagc cccagaacga gatccccgtg gacctgctgt gccacgagca gctgagcgac   2100
agcgaggaag aaaacgacga gatcgacggc gtgaaccacc agcacctgcc tgccagaaga   2160
gccgagcccc agagacacac ccacaagtgc atcgacttct acagcagaat cagagagctg   2220
agacactaca gcgacagcgt gtacggcgac accctggaga agctgaccaa caccggcctg   2280
```

```
tacaacctgc tgatcagatg cctgagatgc cagaagcccc tgaaccctgc cgagaagctg   2340
agacacctga acgagaagag aagattccac aacatcgccg gccactacag aggccagtgc   2400
cacagctgct gcaacagagc cagacaggag agactgcaga gaagaagaga gacccaggtg   2460
ggatctggca gcggctctgg ctccggctca ctcgagatgt tccaggaccc tgccgaaaga   2520
ccctacaagc tgcatgatct gtgcaatgaa gtcgaagaga gtatccatga aatctgtctg   2580
aattgcgtgt actgtaagca ggagctgcag cgcagtgaag tctacgactt cgcctgctat   2640
gacctgtgca tcgtgtaccg agagggacag ccatatggcg tctgcatgaa gtgtctgaag   2700
ttctactcta agatcagtga atataggtgg ccagccggcc aggctaaacc cgacacttcc   2760
aactataata ttgtgacctc ttgctgtaaa tgcgaggcta ccctgagact gtgcgtgcag   2820
agcacacaca tcgacattag gaagctggag gacctgctga tggggacctt cggaatcgtg   2880
tgcccaggat gttcccagcg agctggatct ggcagtgggt caggaagcgg ctccatgcat   2940
ggagagatta ccacactgca ggactacgtc ctggatctgg agcctgaagc aactgacctg   3000
tactgctatg aacagctgtg cgatagctcc gaggaagagg aagacaccat cgatggccct   3060
gcagggcagg ccaagccaga tacaagtaac tacaacatcg tgacttcatg ctgtaaaccc   3120
tacggcgtct gcatgaaatg tctgaaattc tactcaaaga tcagcgagta tcggtggtac   3180
agatatagcg tgtacgggga gacactggaa aagcagtgca acaaacagct gtgccacctg   3240
ctgatccggt gcattacttg tcagaagccc ctgtgccctg tggagaaaca gcgacacctg   3300
gaggaaaaga aacggtttca taatattggc gggaggtgga caggccgctg catgagctgt   3360
tggaagccta ccagacggga gaccgaagtg ggcagcggca gtgggagcgg aagcgggagt   3420
gtcgagggat ctatggccag attcgacgac cccaagcaga gaccctacaa gctgcccgac   3480
ctgtgcaccg agctgaacac cagcctgcag gacgtgagca tcgcctgcgt gtactgcaag   3540
gccaccctgg agagaaccga ggtgtaccag ttcgccttca aggacctgtg catcgtgtac   3600
agagactgca tcgcctacgc cgcctgccat aaatgtattg atttttattc caggattcgg   3660
gagctccgct attattctaa tagtgtcgaa gctgatggag tcagtcatgc tcagctccct   3720
gctcggaggg cagaacctca gaggcataag atcctgtgcg tgtgctgcaa gtgcgacggc   3780
agaatcgacc tgaccgtgga gagcagcgcc gacgacctga gaaccctgca gcagctgttc   3840
ctgagcaccc tgagcttcgt gtgcccctgg tgcgccacca accagggcag cggaagcgga   3900
agcggcagcg gcagcatgca cggccccaga gccaccctgc aggagatcgt gctgcacctg   3960
gagccccaga acgagctgga ccccgtggac ctgttgtgct acgagcagct gagcgaaagc   4020
gaggaagaga acgacgaggc cgacggcgtg agccacgccc agctgcccgc cagaagagcc   4080
gagccccaga gacaccacaa gtgcatcgac ttctacagca gaatcagaga gctgagatac   4140
tacagcaaca gcgtgtacgg cgagaccctg gagaagatca ccaacaccga gctgtacaac   4200
ctgttgatca gatgcctgag atgccagaag cccctgaacc ccgccgagaa gagaagacac   4260
ctgaaggaca agagaagatt ccacagcatc gccggccagt acagaggcca gtgcaacacc   4320
tgctgcgacc aggccagaca ggagagactg agaaggagga gagagaccca ggtgggatca   4380
ggaagtggat ctgggtccgg cagcatgttc caggacgccg aggagaagcc cagaaccctg   4440
cacgacctgt gccaggccct ggagaccagc gtgcacgaga tcgagctgaa gtgcgtggag   4500
tgcaagaaga ccctgcagag aagcgaggtg tatgacttcg tgttcgccga cctgagaatc   4560
gtgtatagag acggcaaccc cttcgccgtg tgcaaggtgt gtttgaggct cctctccaaa   4620
atttctgaat atcggcatta taactattcc ctctatggaa ggcctgatgg acaggctcag   4680
```

```
ccagctacag caaattatta tattgtcaca tgttgctata cctgcgacac caccgtgaga   4740

ctgtgcatca acagcaccac aaccgacgtg agaaccctgc agcagctgct gatgggcacc   4800

tgcaccatcg tgtgccccag ctgcgcccag cagggctcag gcagcggctc cggcagcgga   4860

tctatgagag gcaacaaccc caccctgaga gagtacatcc tggacctgca ccccgagccc   4920

accgacctgt tctgctacga gcagctgtgc gacagcagcg acgaggacga gatcggcctg   4980

gacagacccg acggccaggc ccagcccgcc accgccaact actacatcgt gacctgctgc   5040

tactgcctga gactgctgag caagatcagc gagtacagac actacaacta cagcctgtac   5100

ggcgacaccc tggagcagac cctgaagaag tgcctgaacg agatcctgat cagatgcatc   5160

atctgccaga gacccctgtg cccccaggag aagaagagac acgtggacct gaacaagaga   5220

ttccacaaca tcagcggcag atggaccggc agatgcgccg tgtgctggag acccagaagg   5280

agacagaccc aggtgggatc ctaa                                          5304
```

<210> SEQ ID NO 28
<211> LENGTH: 1909
<212> TYPE: PRT
<213> ORGANISM: Artificial Sequence
<220> FEATURE:
<223> OTHER INFORMATION: BD-14B polypeptide

<400> SEQUENCE: 28

```
Asp Ala Met Lys Arg Gly Leu Cys Cys Val Leu Leu Leu Cys Gly Ala
1               5                   10                  15

Val Phe Val Ser Pro Ser His Ala Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Ser Gly Ser Gly Ser Gly Ser Gly Ser Met Asp
            180                 185                 190

Ala Met Lys Arg Gly Leu Cys Cys Val Leu Leu Leu Cys Gly Ala Val
        195                 200                 205

Phe Val Ser Pro Ser His Ala Thr Gln Asp Cys Ser Phe Gln His Ser
    210                 215                 220

Pro Ile Ser Ser Asp Phe Ala Val Lys Ile Arg Glu Leu Ser Asp Tyr
225                 230                 235                 240

Leu Leu Gln Asp Tyr Pro Val Thr Val Ala Ser Asn Leu Gln Asp Glu
```

```
                245                 250                 255

Glu Leu Cys Gly Gly Leu Trp Arg Leu Val Leu Ala Gln Arg Trp Met
            260                 265                 270

Glu Arg Leu Lys Thr Val Ala Gly Ser Lys Met Gln Gly Leu Leu Glu
        275                 280                 285

Arg Val Asn Thr Glu Ile His Phe Val Thr Lys Cys Ala Phe Gln Pro
    290                 295                 300

Pro Pro Ser Cys Leu Arg Phe Val Gln Thr Asn Ile Ser Arg Leu Leu
305                 310                 315                 320

Gln Glu Thr Ser Glu Gln Leu Val Ala Leu Lys Pro Trp Ile Thr Arg
                325                 330                 335

Gln Asn Phe Ser Arg Cys Leu Glu Leu Gln Cys Gln Pro Asp Ser Ser
            340                 345                 350

Thr Leu Pro Pro Pro Trp Ser Pro Arg Pro Leu Glu Ala Thr Ala Pro
        355                 360                 365

Thr Ala Pro Gly Ser Gly Ser Gly Ser Gly Ser Gly Ser Met Phe Lys
    370                 375                 380

Asn Pro Ala Glu Arg Pro Arg Lys Leu His Glu Leu Ser Ser Ala Leu
385                 390                 395                 400

Glu Ile Pro Tyr Asp Glu Leu Arg Leu Asn Cys Val Tyr Cys Lys Gly
                405                 410                 415

Gln Leu Thr Glu Thr Glu Val Leu Asp Phe Ala Phe Thr Asp Leu Thr
            420                 425                 430

Ile Val Tyr Arg Asp Asp Thr Pro Tyr Gly Val Cys Thr Lys Cys Leu
        435                 440                 445

Arg Phe Tyr Ser Lys Val Ser Glu Phe Arg Trp Tyr Arg Tyr Ser Val
    450                 455                 460

Tyr Gly Pro Ala Gly Gln Ala Lys Pro Asp Thr Ser Asn Tyr Asn Ile
465                 470                 475                 480

Val Thr Phe Cys Cys Gln Cys Glu Ser Thr Leu Arg Leu Cys Val Gln
                485                 490                 495

Ser Thr Gln Val Asp Ile Arg Ile Leu Gln Glu Leu Leu Met Gly Ser
            500                 505                 510

Phe Gly Ile Val Cys Pro Asn Cys Ser Thr Arg Leu Gly Ser Gly Ser
        515                 520                 525

Gly Ser Gly Ser Gly Ser Met Arg Gly Glu Thr Pro Thr Leu Gln Asp
    530                 535                 540

Tyr Val Leu Asp Leu Gln Pro Glu Ala Thr Asp Leu His Cys Tyr Glu
545                 550                 555                 560

Gln Leu Pro Asp Ser Ser Asp Glu Glu Asp Val Ile Asp Ser Pro Ala
                565                 570                 575

Gly Gln Ala Lys Pro Asp Thr Ser Asn Tyr Asn Ile Val Thr Phe Cys
            580                 585                 590

Cys Gln Cys Leu Arg Phe Tyr Ser Lys Val Ser Glu Phe Arg Trp Tyr
        595                 600                 605

Arg Tyr Ser Val Tyr Gly Thr Thr Leu Glu Lys Leu Thr Asn Lys Gly
    610                 615                 620

Ile Cys Asp Leu Leu Ile Arg Cys Ile Thr Cys Gln Arg Pro Leu Cys
625                 630                 635                 640

Pro Glu Glu Lys Gln Arg His Leu Asp Lys Lys Lys Arg Phe His Asn
                645                 650                 655

Ile Gly Gly Arg Trp Thr Gly Arg Cys Ile Val Cys Trp Arg Arg Pro
            660                 665                 670
```

```
Arg Thr Glu Thr Gln Val Gly Ser Gly Ser Gly Ser Gly Ser Gly Ser
        675                 680                 685

Met Phe Gln Asp Thr Glu Glu Lys Pro Arg Thr Leu His Asp Leu Cys
    690                 695                 700

Gln Ala Leu Glu Thr Thr Ile His Asn Ile Glu Leu Gln Cys Val Glu
705                 710                 715                 720

Cys Lys Asn Pro Leu Gln Arg Ser Glu Val Tyr Asp Phe Ala Phe Ala
            725                 730                 735

Asp Leu Thr Val Val Tyr Arg Glu Gly Asn Pro Phe Gly Ile Cys Lys
            740                 745                 750

Leu Cys Leu Arg Phe Leu Ser Lys Ile Ser Glu Tyr Arg His Tyr Asn
        755                 760                 765

Tyr Ser Val Tyr Gly Pro Asp Gly Gln Ala Gln Pro Ala Thr Ala Asp
    770                 775                 780

Tyr Tyr Ile Val Thr Cys Cys His Thr Cys Asn Thr Thr Val Arg Leu
785                 790                 795                 800

Cys Val Asn Ser Thr Ala Ser Asp Leu Arg Thr Ile Gln Gln Leu Leu
            805                 810                 815

Met Gly Thr Val Asn Ile Val Cys Pro Thr Cys Ala Gln Leu Gly Ser
            820                 825                 830

Gly Ser Gly Ser Gly Ser Gly Ser Met Arg Gly His Lys Pro Thr Leu
        835                 840                 845

Lys Glu Tyr Val Leu Asp Leu Tyr Pro Glu Pro Thr Asp Leu Tyr Cys
    850                 855                 860

Tyr Glu Gln Leu Ser Asp Ser Ser Asp Glu Asp Glu Gly Leu Asp Arg
865                 870                 875                 880

Pro Asp Gly Gln Ala Gln Pro Ala Thr Ala Asp Tyr Tyr Ile Val Thr
            885                 890                 895

Cys Cys His Thr Cys Leu Arg Phe Leu Ser Lys Ile Ser Glu Tyr Arg
            900                 905                 910

His Tyr Asn Tyr Ser Val Tyr Gly His Thr Leu Glu Gln Thr Val Lys
        915                 920                 925

Lys Pro Leu Asn Glu Ile Leu Ile Arg Cys Ile Ile Cys Gln Arg Pro
    930                 935                 940

Leu Cys Pro Gln Glu Lys Lys Arg His Val Asp Leu Asn Lys Arg Phe
945                 950                 955                 960

His Asn Ile Ser Gly Arg Trp Ala Gly Arg Cys Ala Ala Cys Trp Arg
            965                 970                 975

Ser Arg Arg Arg Glu Thr Ala Leu Gly Ser Gly Ser Gly Ser Gly Ser
            980                 985                 990

Gly Ser Met Glu Ser Ala Asn Ala Ser Thr Ser Ala Thr Thr Ile Asp
        995                1000                1005

Gln Leu Cys Lys Thr Phe Asn Leu Ser Met His Thr Leu Gln Ile Asn
    1010                1015                1020

Cys Val Phe Cys Lys Asn Ala Leu Thr Thr Ala Glu Ile Tyr Ser Tyr
1025               1030                1035                1040

Ala Tyr Lys His Leu Lys Val Leu Phe Arg Gly Gly Tyr Pro Tyr Ala
            1045                1050                1055

Ala Cys Ala Cys Cys Leu Glu Phe His Gly Lys Ile Asn Gln Tyr Arg
            1060                1065                1070

His Phe Asp Tyr Ala Gly Tyr Asp Gly Gln Asp Ser Gln Pro Leu Lys
        1075                1080                1085
```

```
Gln His Tyr Gln Ile Val Thr Cys Cys Cys Gly Cys Asp Ser Asn Val
    1090                1095                1100

Arg Leu Val Val Gln Cys Thr Glu Thr Asp Ile Arg Glu Val Gln Gln
1105                1110                1115                1120

Leu Leu Leu Gly Thr Leu Asn Ile Val Cys Pro Ile Cys Ala Pro Lys
                1125                1130                1135

Thr Gly Ser Gly Ser Gly Ser Gly Ser Gly Ser Met His Gly Arg His
            1140                1145                1150

Val Thr Leu Lys Asp Ile Val Leu Asp Leu Gln Pro Pro Asp Pro Val
        1155                1160                1165

Gly Leu His Cys Tyr Glu Gln Leu Val Asp Ser Ser Glu Asp Glu Val
    1170                1175                1180

Asp Glu Val Asp Gly Gln Asp Ser Gln Pro Leu Lys Gln His Tyr Gln
1185                1190                1195                1200

Ile Val Thr Cys Cys Cys Gly Cys Cys Leu Glu Phe His Gly Lys Ile
                1205                1210                1215

Asn Gln Tyr Arg His Phe Asp Tyr Ala Gly Tyr Ala Thr Thr Val Glu
            1220                1225                1230

Glu Glu Thr Lys Gln Asp Ile Leu Asp Val Leu Ile Arg Cys Tyr Leu
        1235                1240                1245

Cys His Lys Pro Leu Cys Glu Val Glu Lys Val Lys His Ile Leu Thr
    1250                1255                1260

Lys Ala Arg Phe Ile Lys Leu Asn Cys Thr Trp Lys Gly Arg Cys Leu
1265                1270                1275                1280

His Cys Trp Thr Thr Cys Met Glu Asp Met Leu Pro Gly Ser Gly Ser
                1285                1290                1295

Gly Ser Gly Ser Gly Ser Met Glu Ser Lys Asp Ala Ser Thr Ser Ala
            1300                1305                1310

Thr Ser Ile Asp Gln Leu Cys Lys Thr Phe Asn Leu Ser Leu His Thr
        1315                1320                1325

Leu Gln Ile Gln Cys Val Phe Cys Arg Asn Ala Leu Thr Thr Ala Glu
    1330                1335                1340

Ile Tyr Ala Tyr Ala Tyr Lys Asn Leu Lys Val Val Trp Arg Asp Asn
1345                1350                1355                1360

Phe Pro Phe Ala Ala Cys Ala Cys Cys Leu Glu Leu Gln Gly Lys Ile
                1365                1370                1375

Asn Gln Tyr Arg His Phe Asn Tyr Ala Ala Tyr Asp Lys Gln Asp Ser
            1380                1385                1390

Gln Pro Leu Thr Gln His Tyr Gln Ile Leu Thr Cys Cys Cys Gly Cys
        1395                1400                1405

Asp Ser Asn Val Arg Leu Val Val Glu Cys Thr Asp Gly Asp Ile Arg
    1410                1415                1420

Gln Leu Gln Asp Leu Leu Leu Gly Thr Leu Asn Ile Val Cys Pro Ile
1425                1430                1435                1440

Cys Ala Pro Lys Pro Gly Ser Gly Ser Gly Ser Gly Ser Gly Ser Met
                1445                1450                1455

His Gly Arg Leu Val Thr Leu Lys Asp Ile Val Leu Asp Leu Gln Pro
            1460                1465                1470

Pro Asp Pro Val Gly Leu His Cys Tyr Glu Gln Leu Glu Asp Ser Ser
        1475                1480                1485

Glu Asp Glu Val Asp Lys Val Asp Lys Gln Asp Ser Gln Pro Leu Thr
    1490                1495                1500

Gln His Tyr Gln Ile Leu Thr Cys Cys Cys Gly Cys Cys Leu Glu Leu
```

```
1505                1510                1515                1520

Gln Gly Lys Ile Asn Gln Tyr Arg His Phe Asn Tyr Ala Ala Tyr Ala
                1525                1530                1535

Pro Thr Val Glu Glu Glu Thr Asn Glu Asp Ile Leu Lys Val Leu Ile
            1540                1545                1550

Arg Cys Tyr Leu Cys His Lys Pro Leu Cys Glu Ile Glu Lys Leu Lys
        1555                1560                1565

His Ile Leu Gly Lys Ala Arg Phe Ile Lys Leu Asn Asn Gln Trp Lys
    1570                1575                1580

Gly Arg Cys Leu His Cys Trp Thr Thr Cys Met Glu Asp Leu Leu Pro
1585                1590                1595                1600

Gly Ser Gly Ser Gly Ser Gly Ser Gly Ser Met Phe Glu Asp Pro Ala
                1605                1610                1615

Thr Arg Pro Arg Thr Leu His Glu Leu Cys Glu Val Leu Glu Glu Ser
            1620                1625                1630

Val His Glu Ile Arg Leu Gln Cys Val Gln Cys Lys Lys Glu Leu Gln
        1635                1640                1645

Arg Arg Glu Val Tyr Lys Phe Leu Phe Thr Asp Leu Arg Ile Val Tyr
    1650                1655                1660

Arg Asp Asn Asn Pro Tyr Gly Val Cys Ile Met Cys Leu Arg Phe Leu
1665                1670                1675                1680

Ser Lys Ile Ser Glu Tyr Arg His Tyr Gln Tyr Ser Leu Tyr Gly Asp
                1685                1690                1695

Arg Pro Asp Gly Gln Ala Glu Gln Ala Thr Ser Asn Tyr Tyr Ile Val
            1700                1705                1710

Thr Tyr Cys His Ser Cys Asp Ser Thr Leu Arg Leu Cys Ile His Ser
        1715                1720                1725

Thr Ala Thr Asp Leu Arg Thr Leu Gln Gln Met Leu Leu Gly Thr Leu
    1730                1735                1740

Gln Val Val Cys Pro Gly Cys Ala Arg Leu Gly Ser Gly Ser Gly Ser
1745                1750                1755                1760

Gly Ser Gly Ser Met Arg Gly Asp Lys Ala Thr Ile Lys Asp Tyr Ile
                1765                1770                1775

Leu Asp Leu Gln Pro Glu Thr Thr Asp Leu His Cys Tyr Glu Gln Leu
            1780                1785                1790

Gly Asp Ser Ser Asp Glu Glu Asp Thr Asp Gly Val Asp Arg Pro Asp
        1795                1800                1805

Gly Gln Ala Glu Gln Ala Thr Ser Asn Tyr Tyr Ile Val Thr Tyr Cys
    1810                1815                1820

Cys Leu Arg Phe Leu Ser Lys Ile Ser Glu Tyr Arg His Tyr Gln Tyr
1825                1830                1835                1840

Ser Leu Tyr Gly Lys Thr Leu Glu Glu Arg Val Lys Lys Pro Leu Ser
                1845                1850                1855

Glu Ile Thr Ile Arg Cys Ile Ile Cys Gln Thr Pro Leu Cys Pro Glu
            1860                1865                1870

Glu Lys Glu Arg His Val Asn Ala Asn Lys Arg Phe His Asn Ile Met
        1875                1880                1885

Gly Arg Trp Thr Gly Arg Cys Ser Glu Cys Trp Arg Pro Arg Pro Val
    1890                1895                1900

Thr Gln Val Gly Ser
1905
```

<210> SEQ ID NO 29

<211> LENGTH: 5160
<212> TYPE: DNA
<213> ORGANISM: Artificial Sequence
<220> FEATURE:
<223> OTHER INFORMATION: polynucleotide encoding BD-14B polypeptide

<400> SEQUENCE: 29
atggacgcca tgaagagagg cctgtgctgc gtgctgctgc tgtgcggcgc cgtgttcgtg 60
agccccagcc acgccaccca ggactgcagc ttccagcaca gccccatcag cagcgacttc 120
gccgtgaaga tcagagagct gagcgactac ctgctgcagg actaccccgt gaccgtggcc 180
agcaacctgc aggacgagga gctgtgcggc ggcctgtgga gactggtgct ggcccagaga 240
tggatggaga gactgaagac cgtggccggc agcaagatgc agggcctgct ggagagagtg 300
aacaccgaga tccacttcgt gaccaagtgc gccttccagc ctccccccag ctgcctgagg 360
ttcgtgcaga ccaacatcag cagactgctg caggagacca gcgagcagct ggtggccctg 420
aagccctgga tcaccagaca gaacttcagc agatgcctgg agctgcagtg ccagcccgac 480
agcagcaccc tgcccccctcc ctggagcccc agacccctgg aggccaccgc tcccacagcc 540
cctggcagcg ggtccggaag tgggtctgga tctatgttca agaaccccgc cgagagaccc 600
agaaagctgc acgagctgag cagcgccctg gagatcccct acgacgagct gagactgaac 660
tgcgtgtact gcaagggcca gctgaccgag accgaggtgc tggacttcgc cttcaccgac 720
ctgaccatcg tgtacagaga cgacaccccc tacggcgtgt gcaccaagtg tctcaggttt 780
tatagtaaag tctctgaatt taggtggtat aggtattccg tctatggtcc tgcaggacag 840
gctaaacctg atacaagtaa ttataatatt gtcacatttt gttgtcagtg tgagagcacc 900
ctgagactgt gcgtgcagag cacccaggtg gacatcagaa tcctgcagga gctgctgatg 960
ggcagcttcg gcatcgtgtg ccccaactgc agcaccagac tgggcagtgg aagcggctca 1020
ggaagcggca gcatgagagg cgagaccccc accctgcagg actacgtgct ggacctgcag 1080
cccgaggcca ccgacctgca ctgctacgag cagctgcccg acagcagcga cgaggaggat 1140
gtgatcgaca gccccgccgg ccaggccaag cccgacacca gcaactacaa catcgtgacc 1200
ttctgctgcc agtgcctgag attctacagc aaggtgagcg agttcagatg gtacagatac 1260
agcgtgtacg gcaccaccct ggagaagctg accaacaagg gcatctgcga cctgctgatc 1320
agatgcatca cctgccagag accccctgtgc cccgaggaga agcagagaca cctggacaag 1380
aagaaaagat tccacaacat cggcggcaga tggaccggca gatgcatcgt gtgctggaga 1440
agacccagaa ccgagaccca ggtgggcagc ggctccggat caggcagcgg aagtatgttc 1500
caggacaccg aggagaagcc cagaaccctg cacgacctgt gccaggccct ggagaccacc 1560
atccacaaca tcgagctgca gtgcgtggag tgcaagaacc ccctgcagag aagcgaggtg 1620
tacgacttcg ccttcgccga cctgaccgtg gtgtacagag agggcaaccc cttcggcatc 1680
tgcaagctgt gtctcaggtt tctcagtaaa atttctgaat ataggcatta taattattcc 1740
gtctatggac ctgatggaca ggctcagcct gctacagcag attattatat tgtcacatgt 1800
tgtcatacat gtaacaccac cgtgagactg tgcgtgaaca gcaccgccag cgatctgaga 1860
accatccagc agctgctgat gggcaccgtg aacatcgtgt gccccacctg cgcccagctg 1920
ggctcaggaa gtggaagcgg ctctggatct atgagaggcc acaagcccac cctgaaggag 1980
tacgtgctgg acctgtaccc cgagcccacc gacctgtact gctacgagca gctgagcgat 2040
agcagcgacg aggacgaggg cctggacaga cccgatggcc aggcccagcc cgccaccgcc 2100
gactactaca tcgtgacctg ctgccacacc tgcctgagat tcctgagcaa gatcagcgag 2160

```
tacagacact acaactacag cgtgtacggc cacaccctgg agcagaccgt gaagaagccc   2220
ctgaacgaga tcctgatcag atgcatcatc tgccagagac ccctgtgccc ccaggagaag   2280
aagagacacg tggacctgaa caagagattc cacaacatca gcggcagatg ggccggcaga   2340
tgcgccgcct gctggagaag cagaagaaga gagaccgccc tgggcagcgg ctctggctcc   2400
ggctcaggat ctatggagtc tgctaacgct tccacatccg ctacaactat cgaccagctg   2460
tgcaagactt tcaacctcag catgcacacc ttgcagatca actgtgtgtt ttgcaaaaac   2520
gccctgacca cagcagaaat ttacagttac gcctacaaac atctgaaggt gctctttcgg   2580
gggggctatc cctacgccgc atgcgcttgt tgcttggaat ttcatggaaa aatcaaccag   2640
tatcggcatt tcgattatgc cggatacgat gggcaggata gtcagcctct gaaacagcac   2700
tatcagattg tgacctgttg ctgtggatgt gacagcaacg tgaggctggt cgtgcagtgt   2760
acagaaacag acatcagaga ggtgcagcag cttcttctgg gcactctcaa catcgtgtgt   2820
cccatctgcg ctccaaaaac cgggtccggc agcggatctg gaagcggctc catgcacggg   2880
cggcacgtga cacttaaaga catcgtcctg gaccttcagc cccctgatcc tgtcggcttg   2940
cactgttacg agcagctggt ggactcatct gaggatgagg tggacgaagt ggacggacag   3000
gattcacagc ctctgaaaca gcattaccag attgtgacct gctgctgcgg ctgttgtctt   3060
gagttccatg gaaaaatcaa ccagtacaga catttcgatt atgccggata cgcaacaacc   3120
gtcgaagagg agactaaaca ggacatcctc gacgtcctga ttcgctgcta cctgtgtcac   3180
aaaccactgt gtgaggtcga aaaggtgaaa cacattctta ccaaggcaag attcatcaaa   3240
ctcaattgta cctggaaggg acggtgcctg cactgttgga ctacatgcat ggaagatatg   3300
cttccaggaa gtgggagcgg ctcaggaagc gggagcatgg aaagtaaaga cgcttccaca   3360
agtgccactt caatcgacca gctctgtaag acattcaact tgagtctgca caccctgcag   3420
atccagtgcg tgttttgcag aaacgcactc acaaccgctg agatttacgc ctatgcttac   3480
aagaacctca aggtcgtgtg gagggataat ttccccttcg ctgcctgcgc ctgttgcctg   3540
gaactgcagg ggaaaatcaa tcagtatcgg catttcaact atgctgctta cgacaaacag   3600
gattctcagc ctctgaccca gcactaccag attctcacct gctgctgcgg ctgcgatagt   3660
aatgtgaggc tcgtggtcga gtgtaccgac ggcgacatta ggcagctcca ggatcttctc   3720
cttggcacac tgaatatcgt gtgtcctatt tgtgccccaa aacccgggtc tggaagtggc   3780
tccggatctg ggagtatgca tggacgcctc gtgacactga aggatattgt gctcgatctg   3840
cagccacctg atcccgtggg cctccactgt tatgagcagc tggaggattc ctcagaagat   3900
gaggtggata aagtggacaa acaggactcc cagcctctta cccagcatta tcagatcctg   3960
acctgctgct gcggatgttg tctggaattg cagggcaaaa tcaaccagta tagacatttc   4020
aattatgctg catacgcccc tacagtcgag gaggaaacca atgaagacat cctcaaggtg   4080
ctgatcagat gttacctctg tcacaagcct ctttgcgaaa tcgagaaact gaagcatatc   4140
ctgggaaagg ctcgctttat caagcttaac aatcagtgga aggcaggtg cctgcactgc   4200
tggaccacct gtatggaaga cctgctgccc gggtccggct caggaagcgg ctccggctct   4260
atgtttgaag acccagccac caggccaaga acattgcacg agctttgcga agtcctcgaa   4320
gagagtgtgc atgagattag gctccagtgt gtgcagtgca agaaggaact tcagcgcaga   4380
gaggtctaca agttcttgtt tacagacctg cggatcgtgt acagggataa taatccctat   4440
ggcgtctgca ttatgtgtct taggttcctg tccaagattt cagagtacag acattaccag   4500
```

```
tattcactgt atggggacag gccagatggc caggccgagc aggctactag taactactac   4560

attgtgacct actgtcactc ctgcgactca accctccggc tgtgcattca cagcaccgcc   4620

accgaccttc gcactctgca gcagatgctg ctcggcacct tgcaggtggt gtgtcccgga   4680

tgcgccaggt tgggcagcgg gagtgggtcc ggaagcggca gtatgagagg cgataaggca   4740

accatcaagg actacatcct ggacctgcag cctgagacca ctgatttgca ttgctacgaa   4800

cagctgggag actcaagcga tgaagaagac actgatggcg tggacaggcc cgacggacag   4860

gccgaacagg ccaccagtaa ctattatatc gtcacctatt gctgcctgag gtttctcagt   4920

aaaatttctg agtacagaca ctatcagtac tcactttacg gcaagacatt ggaggagagg   4980

gtgaagaagc ctctgtccga gatcactatt aggtgcatca tctgtcagac tcccctgtgt   5040

cctgaggaaa aggagcggca tgtcaatgct aacaagagat tccacaacat catgggacgg   5100

tggacaggcc gctgctctga atgctggcgc cccaggccag tgactcaggt gggatcctaa   5160
```

```
<210> SEQ ID NO 30
<211> LENGTH: 1467
<212> TYPE: PRT
<213> ORGANISM: Artificial Sequence
<220> FEATURE:
<223> OTHER INFORMATION: BD-14C polypeptide

<400> SEQUENCE: 30

Asp Ala Met Lys Arg Gly Leu Cys Cys Val Leu Leu Leu Cys Gly Ala
1               5                   10                  15

Val Phe Val Ser Pro Ser His Ala Thr Gln Asp Cys Ser Phe Gln His
            20                  25                  30

Ser Pro Ile Ser Ser Asp Phe Ala Val Lys Ile Arg Glu Leu Ser Asp
        35                  40                  45

Tyr Leu Leu Gln Asp Tyr Pro Val Thr Val Ala Ser Asn Leu Gln Asp
    50                  55                  60

Glu Glu Leu Cys Gly Gly Leu Trp Arg Leu Val Leu Ala Gln Arg Trp
65                  70                  75                  80

Met Glu Arg Leu Lys Thr Val Ala Gly Ser Lys Met Gln Gly Leu Leu
                85                  90                  95

Glu Arg Val Asn Thr Glu Ile His Phe Val Thr Lys Cys Ala Phe Gln
            100                 105                 110

Pro Pro Pro Ser Cys Leu Arg Phe Val Gln Thr Asn Ile Ser Arg Leu
        115                 120                 125

Leu Gln Glu Thr Ser Glu Gln Leu Val Ala Leu Lys Pro Trp Ile Thr
    130                 135                 140

Arg Gln Asn Phe Ser Arg Cys Leu Glu Leu Gln Cys Gln Pro Asp Ser
145                 150                 155                 160

Ser Thr Leu Pro Pro Pro Trp Ser Pro Arg Pro Leu Glu Ala Thr Ala
                165                 170                 175

Pro Thr Ala Pro Gly Ser Gly Ser Gly Ser Gly Ser Gly Ser Met Ala
            180                 185                 190

Arg Phe His Asn Pro Ala Glu Arg Pro Tyr Lys Leu Pro Asp Leu Cys
        195                 200                 205

Thr Thr Leu Asp Thr Thr Leu Gln Asp Ile Thr Ile Ala Cys Val Tyr
    210                 215                 220

Cys Arg Arg Pro Leu Gln Gln Thr Glu Val Tyr Glu Phe Ala Phe Ser
225                 230                 235                 240

Asp Leu Tyr Val Val Tyr Arg Asp Gly Glu Pro Leu Ala Ala Cys Gln
                245                 250                 255
```

```
Ser Cys Ile Lys Phe Tyr Ala Lys Ile Arg Glu Leu Arg Tyr Tyr Ser
            260                 265                 270

Asp Ser Val Gln Leu Leu Ala Arg Arg Asp Glu Pro Gln Arg His Thr
        275                 280                 285

Ile Gln Cys Ser Cys Cys Lys Cys Asn Asn Thr Leu Gln Leu Val Val
    290                 295                 300

Glu Ala Ser Arg Asp Thr Leu Arg Gln Leu Gln Gln Leu Phe Met Asp
305                 310                 315                 320

Ser Leu Gly Phe Val Cys Pro Trp Cys Ala Thr Ala Asn Gln Gly Ser
                325                 330                 335

Gly Ser Gly Ser Gly Ser Gly Ser Met Arg Gly Pro Lys Pro Thr Leu
            340                 345                 350

Gln Glu Ile Val Leu Asp Leu Cys Pro Tyr Asn Glu Ile Gln Pro Val
        355                 360                 365

Asp Leu Val Cys His Glu Gln Leu Gly Glu Ser Glu Asp Glu Ile Asp
    370                 375                 380

Glu Pro Asp His Ala Val Asn His Gln His Gln Leu Leu Ala Arg Arg
385                 390                 395                 400

Asp Glu Pro Gln Arg His Thr Ile Gln Cys Ser Cys Cys Lys Gln Ser
                405                 410                 415

Cys Ile Lys Phe Tyr Ala Lys Ile Arg Glu Leu Arg Tyr Tyr Ser Asp
            420                 425                 430

Ser Val Tyr Ala Thr Thr Leu Glu Asn Ile Thr Asn Thr Lys Leu Tyr
        435                 440                 445

Asn Leu Leu Ile Arg Cys Met Cys Cys Leu Lys Pro Leu Cys Pro Ala
    450                 455                 460

Glu Lys Leu Arg His Leu Asn Ser Lys Arg Arg Phe His Lys Ile Ala
465                 470                 475                 480

Gly Ser Tyr Thr Gly Gln Cys Arg Arg Cys Trp Thr Thr Lys Arg Glu
                485                 490                 495

Asp Arg Arg Leu Thr Arg Arg Glu Thr Gln Val Gly Ser Gly Ser Gly
            500                 505                 510

Ser Gly Ser Gly Ser Met Phe Glu Asp Lys Arg Glu Arg Pro Arg Thr
        515                 520                 525

Leu His Glu Leu Cys Glu Ala Leu Asn Val Ser Met His Asn Ile Gln
    530                 535                 540

Val Val Cys Val Tyr Cys Lys Lys Glu Leu Cys Arg Ala Asp Val Tyr
545                 550                 555                 560

Asn Val Ala Phe Thr Glu Ile Lys Ile Val Tyr Arg Asp Asn Asn Pro
                565                 570                 575

Tyr Ala Val Cys Lys Gln Cys Leu Leu Phe Tyr Ser Lys Ile Arg Glu
            580                 585                 590

Tyr Arg Arg Tyr Ser Arg Ser Val Leu Pro Glu Arg Arg Ala Gly Gln
        595                 600                 605

Ala Thr Cys Tyr Arg Ile Glu Ala Pro Cys Cys Arg Cys Ser Ser Val
    610                 615                 620

Val Gln Leu Ala Val Glu Ser Ser Gly Asp Thr Leu Arg Val Val Gln
625                 630                 635                 640

Gln Met Leu Met Gly Glu Leu Ser Leu Val Cys Pro Cys Cys Ala Asn
                645                 650                 655

Asn Gly Ser Gly Ser Gly Ser Gly Ser Gly Ser Met Arg Gly Asn Val
            660                 665                 670
```

```
Pro Gln Leu Lys Asp Val Val Leu His Leu Thr Pro Gln Thr Glu Ile
        675                 680                 685

Asp Leu Gln Cys Tyr Glu Gln Phe Asp Ser Ser Glu Glu Glu Asp Glu
    690                 695                 700

Val Asp Asn Met Arg Asp Gln Leu Pro Glu Arg Arg Ala Gly Gln Ala
705                 710                 715                 720

Thr Cys Tyr Arg Ile Glu Ala Pro Cys Cys Arg Lys Gln Cys Leu Leu
                725                 730                 735

Phe Tyr Ser Lys Ile Arg Glu Tyr Arg Arg Tyr Ser Arg Ser Val Tyr
            740                 745                 750

Gly Thr Thr Leu Glu Ala Ile Thr Lys Lys Ser Leu Tyr Asp Leu Ser
        755                 760                 765

Ile Arg Cys His Arg Cys Gln Arg Pro Leu Gly Pro Glu Glu Lys Gln
    770                 775                 780

Lys Leu Val Asp Glu Lys Lys Arg Phe His Glu Ile Ala Gly Arg Trp
785                 790                 795                 800

Thr Gly Gln Cys Ala Asn Cys Trp Gln Arg Thr Arg Gln Arg Asn Glu
                805                 810                 815

Thr Gln Val Gly Ser Gly Ser Gly Ser Gly Ser Gly Ser Met Glu Pro
            820                 825                 830

Gln Phe Asn Asn Pro Gln Glu Arg Pro Arg Ser Leu His His Leu Ser
        835                 840                 845

Glu Val Leu Glu Ile Pro Leu Ile Asp Leu Arg Leu Ser Cys Val Tyr
    850                 855                 860

Cys Lys Lys Glu Leu Thr Arg Ala Glu Val Tyr Asn Phe Ala Cys Thr
865                 870                 875                 880

Glu Leu Lys Leu Val Tyr Arg Asp Asp Phe Pro Tyr Ala Val Cys Arg
                885                 890                 895

Val Cys Leu Leu Phe Tyr Ser Lys Val Arg Lys Tyr Arg Tyr Tyr Asp
            900                 905                 910

Tyr Ser Val Gln Ala Arg Gln Ala Lys Gln His Thr Cys Tyr Leu Ile
        915                 920                 925

His Val Pro Cys Cys Glu Cys Lys Phe Val Val Gln Leu Asp Ile Gln
    930                 935                 940

Ser Thr Lys Glu Asp Leu Arg Val Val Gln Gln Leu Leu Met Gly Ala
945                 950                 955                 960

Leu Thr Val Thr Cys Pro Leu Cys Ala Ser Ser Asn Gly Ser Gly Ser
                965                 970                 975

Gly Ser Gly Ser Gly Ser Met His Gly Lys Val Pro Thr Leu Gln Asp
            980                 985                 990

Val Val Leu Glu Leu Thr Pro Gln Thr Glu Ile Asp Leu Gln Cys Asn
        995                 1000                1005

Glu Gln Leu Asp Ser Ser Glu Asp Glu Asp Glu Asp Glu Val Asp His
    1010                1015                1020

Leu Gln Glu Arg Pro Gln Gln Ala Arg Gln Ala Lys Gln His Thr Cys
1025                1030                1035                1040

Tyr Leu Ile His Val Pro Cys Cys Glu Arg Val Cys Leu Leu Phe Tyr
                1045                1050                1055

Ser Lys Val Arg Lys Tyr Arg Tyr Tyr Asp Tyr Ser Val Tyr Gly Ala
            1060                1065                1070

Thr Leu Glu Ser Ile Thr Lys Lys Gln Leu Cys Asp Leu Leu Ile Arg
        1075                1080                1085

Cys Tyr Arg Cys Gln Ser Pro Leu Thr Pro Glu Glu Lys Gln Leu His
```

```
    1090                1095                1100

Cys Asp Arg Lys Arg Arg Phe His Leu Ile Ala His Gly Trp Thr Gly
1105                1110                1115                1120

Ser Cys Leu Gly Cys Trp Arg Gln Thr Ser Arg Glu Pro Arg Glu Ser
                1125                1130                1135

Thr Val Gly Ser Gly Ser Gly Ser Gly Ser Gly Ser Met Ala Arg Phe
            1140                1145                1150

Glu Asp Pro Thr Gln Arg Pro Tyr Lys Leu Pro Asp Leu Ser Thr Thr
        1155                1160                1165

Leu Asn Ile Pro Leu His Asp Ile Arg Ile Asn Cys Val Phe Cys Lys
    1170                1175                1180

Gly Glu Leu Gln Glu Arg Glu Val Phe Glu Phe Ala Phe Asn Asp Leu
1185                1190                1195                1200

Phe Ile Val Tyr Arg Asp Cys Thr Pro Tyr Ala Ala Cys Leu Lys Cys
                1205                1210                1215

Ile Ser Phe Tyr Ala Arg Val Arg Glu Leu Arg Tyr Tyr Arg Asp Ser
            1220                1225                1230

Val Leu Leu Leu Ala Arg Arg Ala Glu Pro Gln Arg His Asn Ile Val
        1235                1240                1245

Cys Val Cys Cys Lys Cys Asn Asn Gln Leu Gln Leu Val Val Glu Thr
    1250                1255                1260

Ser Gln Asp Gly Leu Arg Ala Leu Gln Gln Leu Phe Met Asp Thr Leu
1265                1270                1275                1280

Ser Phe Val Cys Pro Leu Cys Ala Ala Asn Gln Gly Ser Gly Ser Gly
                1285                1290                1295

Ser Gly Ser Gly Ser Met His Gly Pro Lys Ala Thr Leu Cys Asp Ile
            1300                1305                1310

Val Leu Asp Leu Glu Pro Gln Asn Tyr Glu Glu Val Asp Leu Val Cys
        1315                1320                1325

Tyr Glu Gln Leu Pro Asp Ser Asp Ser Glu Asn Glu Lys Asp Glu Pro
    1330                1335                1340

Asp Gly Val Asn His Pro Leu Leu Leu Ala Arg Arg Ala Glu Pro Gln
1345                1350                1355                1360

Arg His Asn Ile Val Cys Val Cys Cys Lys Leu Lys Cys Ile Ser Phe
                1365                1370                1375

Tyr Ala Arg Val Arg Glu Leu Arg Tyr Tyr Arg Asp Ser Val Tyr Gly
            1380                1385                1390

Glu Thr Leu Glu Ala Glu Thr Lys Thr Pro Leu His Glu Leu Leu Ile
        1395                1400                1405

Arg Cys Tyr Arg Cys Leu Lys Pro Leu Cys Pro Thr Asp Lys Leu Lys
    1410                1415                1420

His Ile Thr Glu Lys Arg Arg Phe His Asn Ile Ala Gly Ile Tyr Thr
1425                1430                1435                1440

Gly Gln Cys Arg Gly Cys Arg Thr Arg Ala Arg His Leu Arg Gln Gln
                1445                1450                1455

Arg Gln Ala Arg Ser Glu Thr Leu Val Gly Ser
            1460                1465
```

<210> SEQ ID NO 31
<211> LENGTH: 4407
<212> TYPE: DNA
<213> ORGANISM: Artificial Sequence
<220> FEATURE:
<223> OTHER INFORMATION: polynucleotide encoding BD-14C polypeptide

<400> SEQUENCE: 31

```
atggacgcca tgaagagagg cctgtgctgc gtgctgctgc tgtgcggcgc cgtgttcgtg     60
agccccagcc acgccaccca ggactgcagc ttccagcaca gccccatcag cagcgacttc    120
gccgtgaaga tcagagagct gagcgactac ctgctgcagg actaccccgt gaccgtggcc    180
agcaacctgc aggacgagga gctgtgcggc ggcctgtgga gactggtgct ggcccagaga    240
tggatggaga gactgaagac cgtggccggc agcaagatgc agggcctgct ggagagagtg    300
aacaccgaga tccacttcgt gaccaagtgc gccttccagc ctccccccag ctgcctgagg    360
ttcgtgcaga ccaacatcag cagactgctg caggagacca gcgagcagct ggtggccctg    420
aagccctgga tcaccagaca gaacttcagc agatgcctgg agctgcagtg ccagcccgac    480
agcagcaccc tgcccccctcc ctggagcccc agacccctgg aggccaccgc tcccacagcc    540
cctggcagcg ggtccggaag tgggtctgga tctatggcta gatttcataa ccccgccgag    600
cgcccttaca aactgcccga cctgtgcacc actctggata ccactctgca ggacatcact    660
atcgcatgcg tgtactgtcg gagaccactg cagcagaccg aggtctatga gttcgccttt    720
tccgacctgt acgtggtcta tagagatggc gagcccctgg ccgcttgcca gtcttgtatc    780
aagttttacg ctaagatcag ggagctgcgc tactatagcg actccgtgca gctgctggca    840
aggcgcgatg aaccccagag gcacaccatc cagtgctcct gctgtaagtg taacaataca    900
ctgcagctgg tggtcgaggc ctcacgcgac actctgcgac agctgcagca gctgtttatg    960
gatagcctgg ggttcgtgtg cccttggtgt gccactgcta accagggctc tgggagtgga   1020
tcaggcagcg ggtccatgcg aggaccaaag cctaccctgc aggagatcgt gctggacctg   1080
tgcccctaca acgaaattca gcctgtggat ctggtctgtc acgagcagct gggcgaaagc   1140
gaggatgaaa tcgacgagcc agatcatgca gtgaatcacc agcatcagct gctggcccga   1200
cgggacgaac cacagcggca cacaattcag tgcagctgct gtaagcagtc ctgtatcaag   1260
ttctacgcaa aaattcgaga gctgcggtac tattctgata gcgtgtacgc caccacactg   1320
gaaaacatca ctaataccaa actgtataac ctgctgatta gatgcatgtg ctgtctgaag   1380
ccactgtgcc ccgccgagaa actgaggcac ctgaatagca agagaaggtt tcataaaatc   1440
gctgggtcct acaccggaca gtgccgccga tgttggacta ccaagagaga ggaccggaga   1500
ctgaccaggc gcgaaacaca agtgggatca ggcagcgggt ccggatctgg cagtatgttc   1560
gaggataaac gggaaagacc aaggacactg cacgagctgt gcgaagccct gaacgtgtcc   1620
atgcataata ttcaggtggt ctgcgtctac tgtaagaaag aactgtgccg cgcagacgtg   1680
tataatgtcg cctttactga gatcaagatc gtgtaccggg ataacaatcc ctatgccgtc   1740
tgcaagcagt gtctgctgtt ctactctaaa atccgcgaat accgacggta ttcacggagc   1800
gtgctgcctg agagaagggc aggccaggcc acttgctata gaattgaggc cccatgctgt   1860
aggtgtagct ccgtggtcca gctggctgtg gaatctagtg gagacaccct gagagtggtc   1920
cagcagatgc tgatgggaga gctgagcctg gtgtgcccat gctgtgccaa caatgggtcc   1980
ggatctggca gtgggtcagg aagcatgagg ggcaacgtgc cacagctgaa ggacgtggtc   2040
ctgcacctga ctccacagac cgagatcgac ctgcagtgct acgaacagtt tgattcaagc   2100
gaggaagagg acgaagtgga taatatgcga gatcagctgc cagagcgccg agctggacag   2160
gcaacctgct accgcatcga ggcaccttgc tgtcggaaac agtgcctgct gttctattcc   2220
aaaattagag agtaccggcg gtacagccgg agcgtgtacg gcacaactct ggaagctatc   2280
acaaagaaat ctctgtatga cctgagtatt agatgccaca ggtgtcagcg ccctctggga   2340
```

```
ccagaagaga agcagaaact ggtggatgag aagaaacgct ttcatgaaat cgcaggccgg   2400

tggaccggac agtgcgctaa ctgttggcag cgcacacgac agcggaatga gactcaagtg   2460

ggcagtgggt caggaagcgg ctccgggtct atggagcccc agttcaacaa tcctcaggaa   2520

agaccaaggt cactgcacca tctgagcgag gtgctggaaa tccctctgat tgacctgaga   2580

ctgagctgcg tgtactgtaa gaaagagctg acaagggctg aagtctataa ctttgcatgc   2640

actgagctga agctggtgta ccgcgacgat tttccctatg ccgtgtgccg ggtctgtctg   2700

ctgttctact ccaaggtgcg aaaataccgg tactatgatt atagtgtcca ggcccgccag   2760

gctaaacagc acacatgcta tctgatccat gtgccatgct gtgagtgtaa gttcgtggtc   2820

cagctggaca ttcagagcac taaagaggac ctgcgggtgg tccagcagct gctgatggga   2880

gctctgacag tgacttgccc cctgtgcgca tcctctaacg gaagtggctc agggagcggc   2940

agcggctcta tgcacggcaa ggtgcccaca ctgcaggacg tggtcctgga gctgacacct   3000

cagactgaaa tcgacctgca gtgcaatgag cagctggata gttcagagga cgaagatgag   3060

gacgaagtgg atcatctgca ggaaagacct cagcaggcaa ggcaggccaa gcagcacacc   3120

tgctacctga ttcacgtccc atgctgtgag cgcgtctgtc tgctgtttta cagcaaggtg   3180

agaaaatata ggtactatga ctacagtgtc tatggcgcca ctctggagtc aatcaccaag   3240

aaacagctgt gcgatctgct gattcgatgc taccggtgcc agagcccact gacccctgaa   3300

gagaagcagc tgcactgcga cagaaaaagg cgcttccacc tgatcgccca tggatggaca   3360

ggcagctgcc tgggctgttg gaggcagact tcccgggagc ctagagaatc taccgtgggg   3420

agtggatcag gcagcgggtc cggatctatg gctagatttg aggaccccac acagaggcct   3480

tacaagctgc ccgacctgag caccaccctg aacattccac tgcatgacat ccgcattaat   3540

tgcgtcttct gtaaaggcga gctgcaggag cgggaagtgt tcgaatttgc cttcaacgac   3600

ctgtttatcg tgtacaggga ttgcaccccc tatgcagcct gcctgaagtg tatttccttc   3660

tacgctcgcg tgcgagagct gaggtactat cgcgattctg tcctgctgct ggctcgacgg   3720

gcagaacctc agcgccacaa tatcgtgtgc gtctgctgta aatgtaacaa tcagctgcag   3780

ctggtcgtgg agaccagcca ggacggactg cgggccctgc aacaactgtt tatggataca   3840

ctgagcttcg tgtgccctct gtgcgctgca aaccaaggca gtgggtcagg aagcggctcc   3900

gggtctatgc atggaccaaa ggccaccctg tgcgacatcg tgctggatct ggaaccccag   3960

aattacgaag aggtggacct ggtctgttat gagcagctgc ctgatagtga ctcagagaac   4020

gaaaaagacg aaccagatgg cgtgaatcac ccactgctgc tggccagaag ggctgagcca   4080

cagagacata acatcgtgtg cgtctgctgc aagctgaaat gtattagttt ttacgctcgg   4140

gtgagagaac tgcgatacta tcgggactct gtctatgggg agactctgga ggcagaaacc   4200

aagacacccc tgcacgagct gctgatcaga tgctacaggt gtctgaaacc tctgtgcccc   4260

accgataagc tgaaacacat tacagagaaa cgccgattcc ataatatcgc cggaatctac   4320

accggccagt gcagggggtg tagaacacga gcaaggcatc tgaggcagca gcggcaggca   4380

aggtccgaga ctctggtggg atcctaa                                       4407
```

```
<210> SEQ ID NO 32
<211> LENGTH: 115
<212> TYPE: PRT
<213> ORGANISM: Artificial Sequence
<220> FEATURE:
<223> OTHER INFORMATION: HSV-2 UL39-N1 peptide
```

<400> SEQUENCE: 32

```
Met Arg Ser Pro Ser Glu Arg Gln Glu Pro Arg Glu Pro Glu Val Ala
1               5                   10                  15

Pro Pro Gly Gly Asp His Val Phe Cys Arg Lys Val Ser Gly Val Met
            20                  25                  30

Val Leu Ser Ser Asp Pro Pro Gly Pro Ala Ala Tyr Arg Ile Ser Asp
        35                  40                  45

Ser Ser Phe Val Gln Cys Gly Ser Asn Cys Ser Met Ile Ile Asp Gly
    50                  55                  60

Asp Gly Asp Gly Arg Thr Ala Val Val Ala Leu Gly Gly Thr Ser Gly
65                  70                  75                  80

Pro Ser Ala Thr Thr Ser Val Gly Thr Gln Thr Ser Gly Glu Phe Leu
                85                  90                  95

His Gly Asn Pro Arg Thr Pro Glu Pro Gln Gly Pro Gln Ala Val Pro
            100                 105                 110

Pro Pro Pro
        115
```

<210> SEQ ID NO 33
<211> LENGTH: 26
<212> TYPE: PRT
<213> ORGANISM: Artificial Sequence
<220> FEATURE:
<223> OTHER INFORMATION: HSV-2 UL39-C2 peptide

<400> SEQUENCE: 33

```
Tyr Cys Lys Val Arg Lys Ala Thr Asn Ser Gly Val Phe Ala Gly Asp
1               5                   10                  15

Asp Asn Ile Val Cys Thr Ser Cys Ala Leu
            20                  25
```

<210> SEQ ID NO 34
<211> LENGTH: 73
<212> TYPE: PRT
<213> ORGANISM: Artificial Sequence
<220> FEATURE:
<223> OTHER INFORMATION: HSV-2 UL39-N2 peptide

<400> SEQUENCE: 34

```
Pro Pro Pro Phe Pro Trp Gly His Glu Cys Cys Ala Arg Arg Asp Ala
1               5                   10                  15

Arg Gly Gly Ala Glu Lys Asp Val Gly Ala Ala Glu Ser Trp Ser Asp
            20                  25                  30

Gly Pro Ser Ser Asp Ser Glu Thr Glu Asp Ser Asp Ser Ser Asp Glu
        35                  40                  45

Asp Thr Gly Ser Glu Thr Leu Ser Arg Ser Ser Ser Ile Trp Ala Ala
    50                  55                  60

Gly Ala Thr Asp Asp Asp Asp Ser Asp
65                  70
```

<210> SEQ ID NO 35
<211> LENGTH: 718
<212> TYPE: PRT
<213> ORGANISM: Artificial Sequence
<220> FEATURE:
<223> OTHER INFORMATION: HSV-2 UL39-N4-C1 peptide

<400> SEQUENCE: 35

```
Pro Asn Ala Tyr Thr Pro Tyr His Leu Arg Glu Tyr Ala Thr Arg Leu
1               5                   10                  15
```

```
Val Asn Gly Phe Lys Pro Leu Val Arg Arg Ser Ala Arg Leu Tyr Arg
            20                  25                  30

Ile Leu Gly Val Leu Val His Leu Arg Ile Arg Thr Arg Glu Ala Ser
        35                  40                  45

Phe Glu Glu Trp Met Arg Ser Lys Glu Val Asp Leu Asp Phe Gly Leu
    50                  55                  60

Thr Glu Arg Leu Arg Glu His Glu Ala Gln Leu Met Ile Leu Ala Gln
65                  70                  75                  80

Ala Leu Asn Pro Tyr Asp Cys Leu Ile His Ser Thr Pro Asn Thr Leu
                85                  90                  95

Val Glu Arg Gly Leu Gln Ser Ala Leu Lys Tyr Glu Glu Phe Tyr Leu
            100                 105                 110

Lys Arg Phe Gly Gly His Tyr Met Glu Ser Val Phe Gln Met Tyr Thr
        115                 120                 125

Arg Ile Ala Gly Phe Leu Ala Cys Arg Ala Thr Arg Gly Met Arg His
    130                 135                 140

Ile Ala Leu Gly Arg Gln Gly Ser Trp Trp Glu Met Phe Lys Phe Phe
145                 150                 155                 160

Phe His Arg Leu Tyr Asp His Gln Ile Val Pro Ser Thr Pro Ala Met
                165                 170                 175

Leu Asn Leu Gly Thr Arg Asn Tyr Tyr Thr Ser Ser Cys Tyr Leu Val
            180                 185                 190

Asn Pro Gln Ala Thr Thr Asn Gln Ala Thr Leu Arg Ala Ile Thr Gly
        195                 200                 205

Asn Val Ser Ala Ile Leu Ala Arg Asn Gly Gly Ile Gly Leu Cys Met
    210                 215                 220

Gln Ala Phe Asn Asp Ala Ser Pro Gly Thr Ala Ser Ile Met Pro Ala
225                 230                 235                 240

Leu Lys Val Leu Asp Ser Leu Val Ala Ala His Asn Lys Gln Ser Thr
                245                 250                 255

Arg Pro Thr Gly Ala Cys Val Tyr Leu Glu Pro Trp His Ser Asp Val
            260                 265                 270

Arg Ala Val Leu Arg Met Lys Gly Val Leu Ala Gly Glu Glu Ala Gln
        275                 280                 285

Arg Cys Asp Asn Ile Phe Ser Ala Leu Trp Met Pro Asp Leu Phe Phe
    290                 295                 300

Lys Arg Leu Ile Arg His Leu Asp Gly Glu Lys Asn Val Thr Trp Ser
305                 310                 315                 320

Leu Phe Asp Arg Asp Thr Ser Met Ser Leu Ala Asp Phe His Gly Glu
                325                 330                 335

Glu Phe Glu Lys Leu Tyr Glu His Leu Glu Ala Met Gly Phe Gly Glu
            340                 345                 350

Thr Ile Pro Ile Gln Asp Leu Ala Tyr Ala Ile Val Arg Ser Ala Ala
        355                 360                 365

Thr Thr Gly Ser Pro Phe Ile Met Phe Lys Asp Ala Val Asn Arg His
    370                 375                 380

Tyr Ile Tyr Asp Thr Gln Gly Ala Ala Ile Ala Gly Ser Asn Leu Cys
385                 390                 395                 400

Thr Glu Ile Val His Pro Ala Ser Lys Arg Ser Ser Gly Val Cys Asn
                405                 410                 415

Leu Gly Ser Val Asn Leu Ala Arg Cys Val Ser Arg Gln Thr Phe Asp
            420                 425                 430
```

```
Phe Gly Arg Leu Arg Asp Ala Val Gln Ala Cys Val Leu Met Val Asn
        435                 440                 445

Ile Met Ile Asp Ser Thr Leu Gln Pro Thr Pro Gln Cys Thr Arg Gly
    450                 455                 460

Asn Asp Asn Leu Arg Ser Met Gly Ile Gly Met Gln Gly Leu His Thr
465                 470                 475                 480

Ala Cys Leu Lys Met Gly Leu Asp Leu Glu Ser Ala Glu Phe Arg Asp
                485                 490                 495

Leu Asn Thr His Ile Ala Glu Val Met Leu Leu Ala Ala Met Lys Thr
            500                 505                 510

Ser Asn Ala Leu Cys Val Arg Gly Ala Arg Pro Phe Ser His Phe Lys
        515                 520                 525

Arg Ser Met Tyr Arg Ala Gly Arg Phe His Trp Glu Arg Phe Ser Asn
    530                 535                 540

Ala Ser Pro Arg Tyr Glu Gly Glu Trp Glu Met Leu Arg Gln Ser Met
545                 550                 555                 560

Met Lys His Gly Leu Arg Asn Ser Gln Phe Ile Ala Leu Met Pro Thr
                565                 570                 575

Ala Ala Ser Ala Gln Ile Ser Asp Val Ser Glu Gly Phe Ala Pro Leu
            580                 585                 590

Phe Thr Asn Leu Phe Ser Lys Val Thr Arg Asp Gly Glu Thr Leu Arg
        595                 600                 605

Pro Asn Thr Leu Leu Leu Lys Glu Leu Glu Arg Thr Phe Gly Gly Lys
    610                 615                 620

Arg Leu Leu Asp Ala Met Asp Gly Leu Glu Ala Lys Gln Trp Ser Val
625                 630                 635                 640

Ala Gln Ala Leu Pro Cys Leu Asp Pro Ala His Pro Leu Arg Arg Phe
                645                 650                 655

Lys Thr Ala Phe Asp Tyr Asp Gln Glu Leu Leu Ile Asp Leu Cys Ala
            660                 665                 670

Asp Arg Ala Pro Tyr Val Asp His Ser Gln Ser Met Thr Leu Tyr Val
        675                 680                 685

Thr Glu Lys Ala Asp Gly Thr Leu Pro Ala Ser Thr Leu Val Arg Leu
    690                 695                 700

Leu Val His Ala Tyr Lys Arg Gly Leu Lys Thr Gly Met Tyr
705                 710                 715
```

<210> SEQ ID NO 36
<211> LENGTH: 191
<212> TYPE: PRT
<213> ORGANISM: Artificial Sequence
<220> FEATURE:
<223> OTHER INFORMATION: HSV-2 UL39-N3 peptide

<400> SEQUENCE: 36

```
Thr Leu Ser Arg Ser Ser Ser Ile Trp Ala Ala Gly Ala Thr Asp Asp
1               5                   10                  15

Asp Asp Ser Asp Ser Asp Ser Arg Ser Asp Asp Ser Val Gln Pro Asp
            20                  25                  30

Val Val Val Arg Arg Arg Trp Ser Asp Gly Pro Ala Pro Val Ala Phe
        35                  40                  45

Pro Lys Pro Arg Arg Pro Gly Asp Ser Pro Gly Asn Pro Gly Leu Gly
    50                  55                  60

Ala Gly Thr Gly Pro Gly Ser Ala Thr Asp Pro Arg Ala Ser Ala Asp
65                  70                  75                  80
```

```
Ser Asp Ser Ala Ala His Ala Ala Ala Pro Gln Ala Asp Val Ala Pro
                85                  90                  95

Val Leu Asp Ser Gln Pro Thr Val Gly Thr Asp Pro Gly Tyr Pro Val
            100                 105                 110

Pro Leu Glu Leu Thr Pro Glu Asn Ala Glu Ala Val Ala Arg Phe Leu
        115                 120                 125

Gly Asp Ala Val Asp Arg Glu Pro Ala Leu Met Leu Glu Tyr Phe Cys
    130                 135                 140

Arg Cys Ala Arg Glu Glu Ser Lys Arg Val Pro Pro Arg Thr Phe Gly
145                 150                 155                 160

Ser Ala Pro Arg Leu Thr Glu Asp Asp Phe Gly Leu Leu Asn Tyr Ala
                165                 170                 175

Leu Ala Glu Met Arg Arg Leu Cys Leu Asp Leu Pro Pro Val Pro
            180                 185                 190


<210> SEQ ID NO 37
<211> LENGTH: 1123
<212> TYPE: PRT
<213> ORGANISM: Artificial Sequence
<220> FEATURE:
<223> OTHER INFORMATION: shuffled UL39 polypeptide

<400> SEQUENCE: 37

Met Arg Ser Pro Ser Glu Arg Gln Glu Pro Arg Glu Pro Glu Val Ala
1               5                   10                  15

Pro Pro Gly Gly Asp His Val Phe Cys Arg Lys Val Ser Gly Val Met
            20                  25                  30

Val Leu Ser Ser Asp Pro Pro Gly Pro Ala Ala Tyr Arg Ile Ser Asp
        35                  40                  45

Ser Ser Phe Val Gln Cys Gly Ser Asn Cys Ser Met Ile Ile Asp Gly
    50                  55                  60

Asp Gly Asp Gly Arg Thr Ala Val Val Ala Leu Gly Gly Thr Ser Gly
65                  70                  75                  80

Pro Ser Ala Thr Thr Ser Val Gly Thr Gln Thr Ser Gly Glu Phe Leu
                85                  90                  95

His Gly Asn Pro Arg Thr Pro Glu Pro Gln Gly Pro Gln Ala Val Pro
            100                 105                 110

Pro Pro Pro Tyr Cys Lys Val Arg Lys Ala Thr Asn Ser Gly Val Phe
        115                 120                 125

Ala Gly Asp Asp Asn Ile Val Cys Thr Ser Cys Ala Leu Pro Pro Pro
    130                 135                 140

Phe Pro Trp Gly His Glu Cys Cys Ala Arg Arg Asp Ala Arg Gly Gly
145                 150                 155                 160

Ala Glu Lys Asp Val Gly Ala Ala Glu Ser Trp Ser Asp Gly Pro Ser
                165                 170                 175

Ser Asp Ser Glu Thr Glu Asp Ser Asp Ser Ser Asp Glu Asp Thr Gly
            180                 185                 190

Ser Glu Thr Leu Ser Arg Ser Ser Ser Ile Trp Ala Ala Gly Ala Thr
        195                 200                 205

Asp Asp Asp Asp Ser Asp Pro Asn Ala Tyr Thr Pro Tyr His Leu Arg
    210                 215                 220

Glu Tyr Ala Thr Arg Leu Val Asn Gly Phe Lys Pro Leu Val Arg Arg
225                 230                 235                 240

Ser Ala Arg Leu Tyr Arg Ile Leu Gly Val Leu Val His Leu Arg Ile
                245                 250                 255
```

```
Arg Thr Arg Glu Ala Ser Phe Glu Glu Trp Met Arg Ser Lys Glu Val
            260                 265                 270

Asp Leu Asp Phe Gly Leu Thr Glu Arg Leu Arg Glu His Glu Ala Gln
        275                 280                 285

Leu Met Ile Leu Ala Gln Ala Leu Asn Pro Tyr Asp Cys Leu Ile His
    290                 295                 300

Ser Thr Pro Asn Thr Leu Val Glu Arg Gly Leu Gln Ser Ala Leu Lys
305                 310                 315                 320

Tyr Glu Glu Phe Tyr Leu Lys Arg Phe Gly Gly His Tyr Met Glu Ser
                325                 330                 335

Val Phe Gln Met Tyr Thr Arg Ile Ala Gly Phe Leu Ala Cys Arg Ala
            340                 345                 350

Thr Arg Gly Met Arg His Ile Ala Leu Gly Arg Gln Gly Ser Trp Trp
        355                 360                 365

Glu Met Phe Lys Phe Phe Phe His Arg Leu Tyr Asp His Gln Ile Val
    370                 375                 380

Pro Ser Thr Pro Ala Met Leu Asn Leu Gly Thr Arg Asn Tyr Tyr Thr
385                 390                 395                 400

Ser Ser Cys Tyr Leu Val Asn Pro Gln Ala Thr Thr Asn Gln Ala Thr
                405                 410                 415

Leu Arg Ala Ile Thr Gly Asn Val Ser Ala Ile Leu Ala Arg Asn Gly
            420                 425                 430

Gly Ile Gly Leu Cys Met Gln Ala Phe Asn Asp Ala Ser Pro Gly Thr
        435                 440                 445

Ala Ser Ile Met Pro Ala Leu Lys Val Leu Asp Ser Leu Val Ala Ala
    450                 455                 460

His Asn Lys Gln Ser Thr Arg Pro Thr Gly Ala Cys Val Tyr Leu Glu
465                 470                 475                 480

Pro Trp His Ser Asp Val Arg Ala Val Leu Arg Met Lys Gly Val Leu
                485                 490                 495

Ala Gly Glu Glu Ala Gln Arg Cys Asp Asn Ile Phe Ser Ala Leu Trp
            500                 505                 510

Met Pro Asp Leu Phe Phe Lys Arg Leu Ile Arg His Leu Asp Gly Glu
        515                 520                 525

Lys Asn Val Thr Trp Ser Leu Phe Asp Arg Asp Thr Ser Met Ser Leu
    530                 535                 540

Ala Asp Phe His Gly Glu Glu Phe Glu Lys Leu Tyr Glu His Leu Glu
545                 550                 555                 560

Ala Met Gly Phe Gly Glu Thr Ile Pro Ile Gln Asp Leu Ala Tyr Ala
                565                 570                 575

Ile Val Arg Ser Ala Ala Thr Thr Gly Ser Pro Phe Ile Met Phe Lys
            580                 585                 590

Asp Ala Val Asn Arg His Tyr Ile Tyr Asp Thr Gln Gly Ala Ala Ile
        595                 600                 605

Ala Gly Ser Asn Leu Cys Thr Glu Ile Val His Pro Ala Ser Lys Arg
    610                 615                 620

Ser Ser Gly Val Cys Asn Leu Gly Ser Val Asn Leu Ala Arg Cys Val
625                 630                 635                 640

Ser Arg Gln Thr Phe Asp Phe Gly Arg Leu Arg Asp Ala Val Gln Ala
                645                 650                 655

Cys Val Leu Met Val Asn Ile Met Ile Asp Ser Thr Leu Gln Pro Thr
            660                 665                 670

Pro Gln Cys Thr Arg Gly Asn Asp Asn Leu Arg Ser Met Gly Ile Gly
```

```
        675                 680                 685

Met Gln Gly Leu His Thr Ala Cys Leu Lys Met Gly Leu Asp Leu Glu
    690                 695                 700

Ser Ala Glu Phe Arg Asp Leu Asn Thr His Ile Ala Glu Val Met Leu
705                 710                 715                 720

Leu Ala Ala Met Lys Thr Ser Asn Ala Leu Cys Val Arg Gly Ala Arg
                725                 730                 735

Pro Phe Ser His Phe Lys Arg Ser Met Tyr Arg Ala Gly Arg Phe His
            740                 745                 750

Trp Glu Arg Phe Ser Asn Ala Ser Pro Arg Tyr Glu Gly Glu Trp Glu
        755                 760                 765

Met Leu Arg Gln Ser Met Met Lys His Gly Leu Arg Asn Ser Gln Phe
    770                 775                 780

Ile Ala Leu Met Pro Thr Ala Ala Ser Ala Gln Ile Ser Asp Val Ser
785                 790                 795                 800

Glu Gly Phe Ala Pro Leu Phe Thr Asn Leu Phe Ser Lys Val Thr Arg
                805                 810                 815

Asp Gly Glu Thr Leu Arg Pro Asn Thr Leu Leu Leu Lys Glu Leu Glu
            820                 825                 830

Arg Thr Phe Gly Gly Lys Arg Leu Leu Asp Ala Met Asp Gly Leu Glu
        835                 840                 845

Ala Lys Gln Trp Ser Val Ala Gln Ala Leu Pro Cys Leu Asp Pro Ala
    850                 855                 860

His Pro Leu Arg Arg Phe Lys Thr Ala Phe Asp Tyr Asp Gln Glu Leu
865                 870                 875                 880

Leu Ile Asp Leu Cys Ala Asp Arg Ala Pro Tyr Val Asp His Ser Gln
                885                 890                 895

Ser Met Thr Leu Tyr Val Thr Glu Lys Ala Asp Gly Thr Leu Pro Ala
            900                 905                 910

Ser Thr Leu Val Arg Leu Leu Val His Ala Tyr Lys Arg Gly Leu Lys
        915                 920                 925

Thr Gly Met Tyr Thr Leu Ser Arg Ser Ser Ser Ile Trp Ala Ala Gly
    930                 935                 940

Ala Thr Asp Asp Asp Asp Ser Asp Ser Asp Ser Arg Ser Asp Asp Ser
945                 950                 955                 960

Val Gln Pro Asp Val Val Val Arg Arg Arg Trp Ser Asp Gly Pro Ala
                965                 970                 975

Pro Val Ala Phe Pro Lys Pro Arg Arg Pro Gly Asp Ser Pro Gly Asn
            980                 985                 990

Pro Gly Leu Gly Ala Gly Thr Gly Pro Gly Ser Ala Thr Asp Pro Arg
        995                 1000                1005

Ala Ser Ala Asp Ser Asp Ser Ala Ala His Ala Ala Ala Pro Gln Ala
    1010                1015                1020

Asp Val Ala Pro Val Leu Asp Ser Gln Pro Thr Val Gly Thr Asp Pro
1025               1030                1035                1040

Gly Tyr Pro Val Pro Leu Glu Leu Thr Pro Glu Asn Ala Glu Ala Val
                1045                1050                1055

Ala Arg Phe Leu Gly Asp Ala Val Asp Arg Glu Pro Ala Leu Met Leu
            1060                1065                1070

Glu Tyr Phe Cys Arg Cys Ala Arg Glu Glu Ser Lys Arg Val Pro Pro
        1075                1080                1085

Arg Thr Phe Gly Ser Ala Pro Arg Leu Thr Glu Asp Asp Phe Gly Leu
    1090                1095                1100
```

```
Leu Asn Tyr Ala Leu Ala Glu Met Arg Arg Leu Cys Leu Asp Leu Pro
1105                1110                1115                1120

Pro Val Pro


<210> SEQ ID NO 38
<211> LENGTH: 3372
<212> TYPE: DNA
<213> ORGANISM: Artificial Sequence
<220> FEATURE:
<223> OTHER INFORMATION: polynucleotide encoding shuffled UL39
      polypeptide

<400> SEQUENCE: 38

atgagaagtc caagcgaaag gcaggaacct agagagccag aagtggcacc acctggaggg     60

gaccacgtct tctgcaggaa ggtgtctggg gtcatggtgc tgagctccga tccaccagga    120

cctgcagctt accggatcag tgactctagt tttgtgcagt gcgggagcaa ctgttccatg    180

atcattgacg gcgatgggga cggaagaaca gctgtggtcg cactgggagg cacttctgga    240

cccagtgcca ccacatccgt gggcacccag acatctgggg aatttctgca cggaaatccc    300

cgaacccctg agccacaggg acctcaggcc gtgcctccac cccttattg taaggtcaga    360

aaagctacca acagtggagt gttcgcaggc gacgataata ttgtctgcac atcatgtgcc    420

ctgccacccc cttttccatg ggccatgag tgctgtgccc ggagagatgc taggggggga    480

gcagaaaaag acgtgggggc agccgagagt tggtcagatg gaccctcaag cgacagcgag    540

accgaagatt ccgactcctc tgatgaagac actggcagtg agaccctgtc acgcagttca    600

agcatctggg ctgcaggggc cacagacgat gacgattccg acccaaacgc ttacacaccc    660

tatcacctga gggaatacgc aactcgcctg gtgaatgggt tcaagcctct ggtcaggcgc    720

agcgcccgcc tgtatagaat cctgggagtc ctggtgcatc tgagaatcag gacacgcgag    780

gctagcttcg aggaatggat gaggtccaaa gaagtggatc tggactttgg cctgactgag    840

cgactgcggg agcacgaagc ccagctgatg attctggcac aggccctgaa cccatacgat    900

tgcctgatcc attcaactcc caatacccctg gtggaacgag gactgcagag cgccctgaag    960

tacgaggagt tctacctgaa acggtttggc gggcactaca tggagagcgt gttccagatg   1020

tataccagaa ttgccggctt tctggcctgt cgggctacaa gagggatgag gcatatcgct   1080

ctgggccgcc aggggagctg gtgggagatg tttaagttct tttccaccg gctgtacgac   1140

catcagatcg tgccatccac ccccgccatg ctgaacctgg gcactcggaa ttactatacc   1200

tcctcttgct atctggtgaa cccccaggcc actaccaatc aggccacact gcgcgctatc   1260

actgggaacg tgagcgcaat tctggcccga aatggaggca tcggactgtg catgcaggca   1320

ttcaacgatg cctctcctgg caccgccagt atcatgccag ctctgaaggt cctggactcc   1380

ctggtggccg ctcacaacaa gcagtctaca aggcctactg gcgcctgcgt gtacctggag   1440

ccatggcatt ctgatgtcag agctgtgctg aggatgaagg gggtgctggc tggagaggaa   1500

gcacagcggt gcgataacat tttcagcgcc ctgtggatgc ctgacctgtt tttcaagcgc   1560

ctgatccgac acctggatgg agagaaaaat gtgacctgga gcctgtttga tcgggacaca   1620

agcatgtccc tggccgactt ccacggcgag gaatttgaaa aactgtacga acatctggag   1680

gctatgggct tcggggagac catcccaatt caggacctgg cttatgcaat tgtgaggagt   1740

gcagccacaa ctggctcacc ctttatcatg ttcaaggatg ccgtcaaccg ccactacatc   1800

tacgacactc agggcgctgc aatcgctggg tctaatctgt gcaccgagat cgtgcatcca   1860
```

```
gcaagtaaaa gaagttcagg agtctgcaac ctgggctcag tgaatctggc acgatgcgtg   1920

agccggcaga ccttcgactt cggaagactg agggacgctg tgcaggcatg cgtcctgatg   1980

gtgaacatca tgattgatag cacactgcag cccactcctc agtgtacccg aggcaacgac   2040

aatctgcggt ccatgggaat tggcatgcag ggactgcaca cagcctgcct gaagatgggc   2100

ctggatctgg aatctgccga gttccgggac ctgaacacac atatcgctga agtgatgctg   2160

ctggccgcta tgaagactag caatgcactg tgcgtgcggg gagccagacc tttttcacac   2220

ttcaaaagaa gcatgtacag ggcaggccgc ttccattggg agcggttttc aaacgccagc   2280

ccaagatatg agggggaatg ggagatgctg agacagagta tgatgaagca cggactgcgg   2340

aacagccagt ttattgcact gatgcccact gcagcctctg cccagatcag cgacgtgagc   2400

gaaggctttg cccctctgtt caccaacctg tttagcaaag tcaccagaga cggggagaca   2460

ctgaggccta atactctgct gctgaaggaa ctggagcgca ctttcggggg aaaacgactg   2520

ctggatgcta tggacggcct ggaggcaaag cagtggtccg tggcacaggc tctgccatgc   2580

ctggaccctg ctcatccact gcgacggttc aaaacagcat ttgattacga ccaggaactg   2640

ctgatcgacc tgtgcgccga cagagctccc tacgtggatc actctcagag tatgacactg   2700

tatgtcactg agaaggccga cggcaccctg cctgctagca cactggtcag gctgctggtg   2760

catgcctaca agcgcggcct gaaaaccggg atgtatacac tgtccaggag ctcctctatc   2820

tgggccgccg gggccaccga cgatgacgat tcagatagcg actcccgctc tgacgattcc   2880

gtgcagccag atgtggtcgt gagaaggcgc tggtctgacg gaccagcacc agtggcattc   2940

cctaaaccac gacggcccgg agatagccca ggcaaccctg gactgggagc aggcactggg   3000

cctggatctg ctaccgaccc aagggcaagt gccgatagtg actcagccgc tcacgcagcc   3060

gctccacagg ctgatgtcgc acctgtgctg gactcccagc caaccgtggg gacagacccc   3120

ggataccccg tccctctgga gctgacccct gaaaatgctg aggcagtggc ccgattcctg   3180

ggcgatgcag tggaccggga accagccctg atgctggagt atttttgccg atgtgcccgg   3240

gaggaaagca agcgggtgcc accaagaact ttcggctccg ctccacgact gaccgaggac   3300

gattttgggc tgctgaacta tgccctggcc gaaatgcgga gactgtgcct ggacctgccc   3360

cccgtgccct aa                                                        3372
```

```
<210> SEQ ID NO 39
<211> LENGTH: 344
<212> TYPE: PRT
<213> ORGANISM: Artificial Sequence
<220> FEATURE:
<223> OTHER INFORMATION: HSV-2 gD_26-349 polypeptide

<400> SEQUENCE: 39

Lys Tyr Ala Leu Ala Asp Pro Ser Leu Lys Met Ala Asp Pro Asn Arg
1               5                   10                  15

Phe Arg Gly Lys Asn Leu Pro Val Leu Asp Gln Leu Thr Asp Pro Pro
            20                  25                  30

Gly Val Lys Arg Val Tyr His Ile Gln Pro Ser Leu Glu Asp Pro Phe
        35                  40                  45

Gln Pro Pro Ser Ile Pro Ile Thr Val Tyr Tyr Ala Val Leu Glu Arg
    50                  55                  60

Ala Cys Arg Ser Val Leu Leu His Ala Pro Ser Glu Ala Pro Gln Ile
65                  70                  75                  80

Val Arg Gly Ala Ser Asp Glu Ala Arg Lys His Thr Tyr Asn Leu Thr
                85                  90                  95
```

```
Ile Ala Trp Tyr Arg Met Gly Asp Asn Cys Ala Ile Pro Ile Thr Val
            100                 105                 110

Met Glu Tyr Thr Glu Cys Pro Tyr Asn Lys Ser Leu Gly Val Cys Pro
        115                 120                 125

Ile Arg Thr Gln Pro Arg Trp Ser Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
                245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Pro Ala Gly Thr Val Ser Ser
        275                 280                 285

Gln Ile Pro Pro Asn Trp His Ile Pro Ser Ile Gln Asp Val Ala Pro
    290                 295                 300

His His Ala Pro Ala Ala Pro Ser Asn Pro Arg Arg Arg Ala Gln Met
305                 310                 315                 320

Ala Pro Lys Arg Leu Arg Leu Pro His Ile Arg Asp Asp Asp Ala Pro
                325                 330                 335

Pro Ser His Gln Pro Leu Phe Tyr
            340


<210> SEQ ID NO 40
<211> LENGTH: 818
<212> TYPE: PRT
<213> ORGANISM: Artificial Sequence
<220> FEATURE:
<223> OTHER INFORMATION: HSV-2 ICP0 polypeptide w/o NLS sequence (a.a.
      510-516)

<400> SEQUENCE: 40

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95

Ser Pro Thr Pro Ala Asp Ala Gln Gly Ser Cys Gly Gly Gly Pro Val
```

```
            100                 105                 110

Gly Glu Glu Glu Ala Glu Ala Gly Gly Gly Gly Asp Val Cys Ala Val
        115                 120                 125

Cys Thr Asp Glu Ile Ala Pro Pro Leu Arg Cys Gln Ser Phe Pro Cys
    130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Ala Val Arg Ala Gly Thr Ala Val
        195                 200                 205

Asp Phe Ile Trp Thr Gly Asn Pro Arg Thr Ala Pro Arg Ser Leu Ser
    210                 215                 220

Leu Gly Gly His Thr Val Arg Ala Leu Ser Pro Thr Pro Pro Trp Pro
225                 230                 235                 240

Gly Thr Asp Asp Glu Asp Asp Asp Leu Ala Asp Val Asp Tyr Val Pro
                245                 250                 255

Pro Ala Pro Arg Arg Ala Pro Arg Arg Gly Gly Gly Gly Ala Gly Ala
            260                 265                 270

Thr Arg Gly Thr Ser Gln Pro Ala Ala Thr Arg Pro Ala Pro Pro Gly
        275                 280                 285

Ala Pro Arg Ser Ser Ser Ser Gly Gly Ala Pro Leu Arg Ala Gly Val
    290                 295                 300

Gly Ser Gly Ser Gly Gly Gly Pro Ala Val Ala Ala Val Val Pro Arg
305                 310                 315                 320

Val Ala Ser Leu Pro Pro Ala Ala Gly Gly Gly Arg Ala Gln Ala Arg
                325                 330                 335

Arg Val Gly Glu Asp Ala Ala Ala Ala Glu Gly Arg Thr Pro Pro Ala
            340                 345                 350

Arg Gln Pro Arg Ala Ala Gln Glu Pro Pro Ile Val Ile Ser Asp Ser
        355                 360                 365

Pro Pro Pro Ser Pro Arg Arg Pro Ala Gly Pro Gly Pro Leu Ser Phe
    370                 375                 380

Val Ser Ser Ser Ser Ala Gln Val Ser Ser Gly Pro Gly Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Ala Pro Val Val Ser
            420                 425                 430

Ala Ser Ala Asp Ala Ala Gly Pro Ala Pro Pro Ala Val Pro Val Asp
        435                 440                 445

Ala His Arg Ala Pro Arg Ser Arg Met Thr Gln Ala Gln Thr Asp Thr
    450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
                485                 490                 495

Thr Pro Gly Ala Ala Pro His Ala Ala Glu Gly Ala Ala Gly Ser Asp
            500                 505                 510

Ser Gly Pro Ala Ala Ser Ser Ser Ala Ser Ser Ser Ala Ala Pro Arg
        515                 520                 525
```

```
Ser Pro Leu Ala Pro Gln Gly Val Gly Ala Lys Arg Ala Ala Pro Arg
    530                 535                 540

Arg Ala Pro Asp Ser Asp Ser Gly Asp Arg Gly His Gly Pro Leu Ala
545                 550                 555                 560

Pro Ala Ser Ala Gly Ala Ala Pro Pro Ser Ala Ser Pro Ser Ser Gln
                565                 570                 575

Ala Ala Val Ala Ala Ala Ser Ser Ser Ser Ala Ser Ser Ser Ser Ala
            580                 585                 590

Ser Ser Ser Ser Ala Ser Ser Ser Ser Ala Ser Ser Ser Ser Ala Ser
        595                 600                 605

Ser Ser Ser Ala Ser Ser Ser Ser Ala Ser Ser Ser Ala Gly Gly Ala
    610                 615                 620

Gly Gly Ser Val Ala Ser Ala Ser Gly Ala Gly Glu Arg Arg Glu Thr
625                 630                 635                 640

Ser Leu Gly Pro Arg Ala Ala Ala Pro Arg Gly Pro Arg Lys Cys Ala
                645                 650                 655

Arg Lys Thr Arg His Ala Glu Gly Gly Pro Glu Pro Gly Ala Arg Asp
            660                 665                 670

Pro Ala Pro Gly Leu Thr Arg Tyr Leu Pro Ile Ala Gly Val Ser Ser
        675                 680                 685

Val Val Ala Leu Ala Pro Tyr Val Asn Lys Thr Val Thr Gly Asp Cys
    690                 695                 700

Leu Pro Val Leu Asp Met Glu Thr Gly His Ile Gly Ala Tyr Val Val
705                 710                 715                 720

Leu Val Asp Gln Thr Gly Asn Val Ala Asp Leu Leu Arg Ala Ala Ala
                725                 730                 735

Pro Ala Trp Ser Arg Arg Thr Leu Leu Pro Glu His Ala Arg Asn Cys
            740                 745                 750

Val Arg Pro Pro Asp Tyr Pro Thr Pro Pro Ala Ser Glu Trp Asn Ser
        755                 760                 765

Leu Trp Met Thr Pro Val Gly Asn Met Leu Phe Asp Gln Gly Thr Leu
    770                 775                 780

Val Gly Ala Leu Asp Phe His Gly Leu Arg Ser Arg His Pro Trp Ser
785                 790                 795                 800

Arg Glu Gln Gly Ala Pro Ala Pro Ala Gly Asp Ala Pro Ala Gly His
                805                 810                 815

Gly Glu


<210> SEQ ID NO 41
<211> LENGTH: 766
<212> TYPE: PRT
<213> ORGANISM: Artificial Sequence
<220> FEATURE:
<223> OTHER INFORMATION: HSV-2 ICP4 polypeptide w/o RS1.3 region (a.a.
      767-1318)

<400> SEQUENCE: 41

Met Ser Ala Glu Gln Arg Lys Lys Lys Lys Thr Thr Thr Thr Thr Gln
1               5                   10                  15

Gly Arg Gly Ala Glu Val Ala Met Ala Asp Glu Asp Gly Gly Arg Leu
            20                  25                  30

Arg Ala Ala Ala Glu Thr Thr Gly Gly Pro Gly Ser Pro Asp Pro Ala
        35                  40                  45

Asp Gly Pro Pro Pro Thr Pro Asn Pro Asp Arg Arg Pro Ala Ala Arg
    50                  55                  60
```

```
Pro Gly Phe Gly Trp His Gly Gly Pro Glu Glu Asn Glu Asp Glu Ala
65                  70                  75                  80

Asp Asp Ala Ala Ala Asp Ala Asp Ala Asp Glu Ala Ala Pro Ala Ser
                85                  90                  95

Gly Glu Ala Val Asp Glu Pro Ala Ala Asp Gly Val Val Ser Pro Arg
            100                 105                 110

Gln Leu Ala Leu Leu Ala Ser Met Val Asp Glu Ala Val Arg Thr Ile
        115                 120                 125

Pro Ser Pro Pro Pro Glu Arg Asp Gly Ala Gln Glu Glu Ala Ala Arg
    130                 135                 140

Ser Pro Ser Pro Pro Arg Thr Pro Ser Met Arg Ala Asp Tyr Gly Glu
145                 150                 155                 160

Glu Asn Asp Asp Asp Asp Asp Asp Asp Asp Asp Asp Asp Arg Asp Ala
                165                 170                 175

Gly Arg Trp Val Arg Gly Pro Glu Thr Thr Ser Ala Val Arg Gly Ala
            180                 185                 190

Tyr Pro Asp Pro Met Ala Ser Leu Ser Pro Arg Pro Pro Ala Pro Arg
        195                 200                 205

Arg His His His His His His His Arg Arg Arg Arg Ala Pro Arg Arg
    210                 215                 220

Arg Ser Ala Ala Ser Asp Ser Ser Lys Ser Gly Ser Ser Ser Ser Ala
225                 230                 235                 240

Ser Ser Ala Ser Ser Ser Ala Ser Ser Ser Ser Ser Ala Ser Ala Ser
                245                 250                 255

Ser Ser Asp Asp Asp Asp Asp Asp Asp Ala Ala Arg Ala Pro Ala Ser
            260                 265                 270

Ala Ala Asp His Ala Ala Gly Gly Thr Leu Gly Ala Asp Asp Glu Glu
        275                 280                 285

Ala Gly Val Pro Ala Arg Ala Pro Gly Ala Ala Pro Arg Pro Ser Pro
    290                 295                 300

Pro Arg Ala Glu Pro Ala Pro Ala Arg Thr Pro Ala Ala Thr Ala Gly
305                 310                 315                 320

Arg Leu Glu Arg Arg Arg Ala Arg Ala Ala Val Ala Gly Arg Asp Ala
                325                 330                 335

Thr Gly Arg Phe Thr Ala Gly Arg Pro Arg Arg Val Glu Leu Asp Ala
            340                 345                 350

Asp Ala Ala Ser Gly Ala Phe Tyr Ala Arg Tyr Arg Asp Gly Tyr Val
        355                 360                 365

Ser Gly Glu Pro Trp Pro Gly Ala Gly Pro Pro Pro Pro Gly Arg Val
    370                 375                 380

Leu Tyr Gly Gly Leu Gly Asp Ser Arg Pro Gly Leu Trp Gly Ala Pro
385                 390                 395                 400

Glu Ala Glu Glu Ala Arg Ala Arg Phe Glu Ala Ser Gly Ala Pro Ala
                405                 410                 415

Pro Val Trp Ala Pro Glu Leu Gly Asp Ala Ala Gln Gln Tyr Ala Leu
            420                 425                 430

Ile Thr Arg Leu Leu Tyr Thr Pro Asp Ala Glu Ala Met Gly Trp Leu
        435                 440                 445

Gln Asn Pro Arg Val Ala Pro Gly Asp Val Ala Leu Asp Gln Ala Cys
    450                 455                 460

Phe Arg Ile Ser Gly Ala Ala Arg Asn Ser Ser Ser Phe Ile Ser Gly
465                 470                 475                 480
```

```
Ser Val Ala Arg Ala Val Pro His Leu Gly Tyr Ala Met Ala Ala Gly
                485                 490                 495

Arg Phe Gly Trp Gly Leu Ala His Val Ala Ala Ala Val Ala Met Ser
            500                 505                 510

Arg Arg Tyr Asp Arg Ala Gln Lys Gly Phe Leu Leu Thr Ser Leu Arg
        515                 520                 525

Arg Ala Tyr Ala Pro Leu Leu Ala Arg Glu Asn Ala Ala Leu Thr Gly
    530                 535                 540

Ala Arg Thr Pro Asp Asp Gly Gly Asp Ala Asn Arg His Asp Gly Asp
545                 550                 555                 560

Asp Ala Arg Gly Lys Pro Ala Ala Ala Ala Ala Pro Leu Pro Ser Ala
                565                 570                 575

Ala Ala Ser Pro Ala Asp Glu Arg Ala Val Pro Ala Gly Tyr Gly Ala
            580                 585                 590

Ala Gly Val Leu Ala Ala Leu Gly Arg Leu Ser Ala Ala Pro Ala Ser
        595                 600                 605

Ala Pro Ala Gly Ala Asp Asp Asp Asp Asp Asp Asp Gly Ala Gly Gly
    610                 615                 620

Gly Gly Gly Gly Arg Arg Ala Glu Ala Gly Arg Val Ala Val Glu Cys
625                 630                 635                 640

Leu Ala Ala Cys Arg Gly Ile Leu Glu Ala Leu Ala Glu Gly Phe Asp
                645                 650                 655

Gly Asp Leu Ala Ala Val Pro Gly Leu Ala Gly Ala Arg Pro Ala Ala
            660                 665                 670

Pro Pro Arg Pro Gly Pro Ala Gly Ala Ala Ala Pro Pro His Ala Asp
        675                 680                 685

Ala Pro Arg Leu Arg Ala Trp Leu Arg Glu Leu Arg Phe Val Arg Asp
    690                 695                 700

Ala Leu Val Leu Met Arg Leu Arg Gly Asp Leu Arg Val Ala Gly Gly
705                 710                 715                 720

Ser Glu Ala Ala Val Ala Ala Val Arg Ala Val Ser Leu Val Ala Gly
                725                 730                 735

Ala Leu Gly Pro Ala Leu Pro Arg Ser Pro Arg Leu Leu Ser Ser Ala
            740                 745                 750

Ala Ala Ala Ala Ala Asp Leu Leu Phe Gln Asn Gln Ser Leu
        755                 760                 765
```

<210> SEQ ID NO 42
<211> LENGTH: 2172
<212> TYPE: PRT
<213> ORGANISM: Artificial Sequence
<220> FEATURE:
<223> OTHER INFORMATION: tPA-Flt3L-gD-IPC0-ICP4 fusion protein

<400> SEQUENCE: 42

```
Met Asp Ala Met Lys Arg Gly Leu Cys Cys Val Leu Leu Leu Cys Gly
1               5                   10                  15

Ala Val Phe Val Ser Pro Ser His Ala Thr Gln Asp Cys Ser Phe Gln
            20                  25                  30

His Ser Pro Ile Ser Ser Asp Phe Ala Val Lys Ile Arg Glu Leu Ser
        35                  40                  45

Asp Tyr Leu Leu Gln Asp Tyr Pro Val Thr Val Ala Ser Asn Leu Gln
    50                  55                  60

Asp Glu Glu Leu Cys Gly Gly Leu Trp Arg Leu Val Leu Ala Gln Arg
65                  70                  75                  80
```

```
Trp Met Glu Arg Leu Lys Thr Val Ala Gly Ser Lys Met Gln Gly Leu
                85                  90                  95

Leu Glu Arg Val Asn Thr Glu Ile His Phe Val Thr Lys Cys Ala Phe
            100                 105                 110

Gln Pro Pro Pro Ser Cys Leu Arg Phe Val Gln Thr Asn Ile Ser Arg
        115                 120                 125

Leu Leu Gln Glu Thr Ser Glu Gln Leu Val Ala Leu Lys Pro Trp Ile
    130                 135                 140

Thr Arg Gln Asn Phe Ser Arg Cys Leu Glu Leu Gln Cys Gln Pro Asp
145                 150                 155                 160

Ser Ser Thr Leu Pro Pro Pro Trp Ser Pro Arg Pro Leu Glu Ala Thr
                165                 170                 175

Ala Pro Thr Ala Pro Gly Ser Gly Ser Gly Ser Gly Ser Gly Ser Gly
            180                 185                 190

Arg Ala Lys Tyr Ala Leu Ala Asp Pro Ser Leu Lys Met Ala Asp Pro
        195                 200                 205

Asn Arg Phe Arg Gly Lys Asn Leu Pro Val Leu Asp Gln Leu Thr Asp
    210                 215                 220

Pro Pro Gly Val Lys Arg Val Tyr His Ile Gln Pro Ser Leu Glu Asp
225                 230                 235                 240

Pro Phe Gln Pro Pro Ser Ile Pro Ile Thr Val Tyr Tyr Ala Val Leu
                245                 250                 255

Glu Arg Ala Cys Arg Ser Val Leu Leu His Ala Pro Ser Glu Ala Pro
            260                 265                 270

Gln Ile Val Arg Gly Ala Ser Asp Glu Ala Arg Lys His Thr Tyr Asn
        275                 280                 285

Leu Thr Ile Ala Trp Tyr Arg Met Gly Asp Asn Cys Ala Ile Pro Ile
    290                 295                 300

Thr Val Met Glu Tyr Thr Glu Cys Pro Tyr Asn Lys Ser Leu Gly Val
305                 310                 315                 320

Cys Pro Ile Arg Thr Gln Pro Arg Trp Ser Tyr Tyr Asp Ser Phe Ser
                325                 330                 335

Ala Val Ser Glu Asp Asn Leu Gly Phe Leu Met His Ala Pro Ala Phe
            340                 345                 350

Glu Thr Ala Gly Thr Tyr Leu Arg Leu Val Lys Ile Asn Asp Trp Thr
        355                 360                 365

Glu Ile Thr Gln Phe Ile Leu Glu His Arg Ala Arg Ala Ser Cys Lys
    370                 375                 380

Tyr Ala Leu Pro Leu Arg Ile Pro Pro Ala Ala Cys Leu Thr Ser Lys
385                 390                 395                 400

Ala Tyr Gln Gln Gly Val Thr Val Asp Ser Ile Gly Met Leu Pro Arg
                405                 410                 415

Phe Ile Pro Glu Asn Gln Arg Thr Val Ala Leu Tyr Ser Leu Lys Ile
            420                 425                 430

Ala Gly Trp His Gly Pro Lys Pro Pro Tyr Thr Ser Thr Leu Leu Pro
        435                 440                 445

Pro Glu Leu Ser Asp Thr Thr Asn Ala Thr Gln Pro Glu Leu Val Pro
    450                 455                 460

Glu Asp Pro Glu Asp Ser Ala Leu Leu Glu Asp Pro Ala Gly Thr Val
465                 470                 475                 480

Ser Ser Gln Ile Pro Pro Asn Trp His Ile Pro Ser Ile Gln Asp Val
                485                 490                 495

Ala Pro His His Ala Pro Ala Ala Pro Ser Asn Pro Arg Arg Arg Ala
```

```
            500                 505                 510

Gln Met Ala Pro Lys Arg Leu Arg Leu Pro His Ile Arg Asp Asp Asp
        515                 520                 525

Ala Pro Pro Ser His Gln Pro Leu Phe Tyr Gly Gly Gly Gly Ser Gly
    530                 535                 540

Gly Gly Gly Ser Gly Gly Gly Gly Ser Gly Gly Gly Gly Ser Gly Gly
545                 550                 555                 560

Gly Gly Ser Met Glu Pro Arg Pro Gly Thr Ser Ser Arg Ala Asp Pro
                565                 570                 575

Gly Pro Glu Arg Pro Pro Arg Gln Thr Pro Gly Thr Gln Pro Ala Ala
            580                 585                 590

Pro His Ala Trp Gly Met Leu Asn Asp Met Gln Trp Leu Ala Ser Ser
        595                 600                 605

Asp Ser Glu Glu Glu Thr Glu Val Gly Ile Ser Asp Asp Asp Leu His
    610                 615                 620

Arg Asp Ser Thr Ser Glu Ala Gly Ser Thr Asp Thr Glu Met Phe Glu
625                 630                 635                 640

Ala Gly Leu Met Asp Ala Ala Thr Pro Pro Ala Arg Pro Pro Ala Glu
                645                 650                 655

Arg Gln Gly Ser Pro Thr Pro Ala Asp Ala Gln Gly Ser Cys Gly Gly
            660                 665                 670

Gly Pro Val Gly Glu Glu Glu Ala Glu Ala Gly Gly Gly Gly Asp Val
        675                 680                 685

Cys Ala Val Cys Thr Asp Glu Ile Ala Pro Pro Leu Arg Cys Gln Ser
    690                 695                 700

Phe Pro Cys Leu His Pro Phe Cys Ile Pro Cys Met Lys Thr Trp Ile
705                 710                 715                 720

Pro Leu Arg Asn Thr Cys Pro Leu Cys Asn Thr Pro Val Ala Tyr Leu
                725                 730                 735

Ile Val Gly Val Thr Ala Ser Gly Ser Phe Ser Thr Ile Pro Ile Val
            740                 745                 750

Asn Asp Pro Arg Thr Arg Val Glu Ala Glu Ala Ala Val Arg Ala Gly
        755                 760                 765

Thr Ala Val Asp Phe Ile Trp Thr Gly Asn Pro Arg Thr Ala Pro Arg
    770                 775                 780

Ser Leu Ser Leu Gly Gly His Thr Val Arg Ala Leu Ser Pro Thr Pro
785                 790                 795                 800

Pro Trp Pro Gly Thr Asp Asp Glu Asp Asp Asp Leu Ala Asp Val Asp
                805                 810                 815

Tyr Val Pro Pro Ala Pro Arg Arg Ala Pro Arg Arg Gly Gly Gly Gly
            820                 825                 830

Ala Gly Ala Thr Arg Gly Thr Ser Gln Pro Ala Ala Thr Arg Pro Ala
        835                 840                 845

Pro Pro Gly Ala Pro Arg Ser Ser Ser Ser Gly Gly Ala Pro Leu Arg
    850                 855                 860

Ala Gly Val Gly Ser Gly Ser Gly Gly Gly Pro Ala Val Ala Ala Val
865                 870                 875                 880

Val Pro Arg Val Ala Ser Leu Pro Pro Ala Ala Gly Gly Gly Arg Ala
                885                 890                 895

Gln Ala Arg Arg Val Gly Glu Asp Ala Ala Ala Ala Glu Gly Arg Thr
            900                 905                 910

Pro Pro Ala Arg Gln Pro Arg Ala Ala Gln Glu Pro Pro Ile Val Ile
        915                 920                 925
```

```
Ser Asp Ser Pro Pro Pro Ser Pro Arg Arg Pro Ala Gly Pro Gly Pro
    930                 935                 940

Leu Ser Phe Val Ser Ser Ser Ser Ala Gln Val Ser Ser Gly Pro Gly
945                 950                 955                 960

Gly Gly Gly Leu Pro Gln Ser Ser Gly Arg Ala Ala Arg Pro Arg Ala
                965                 970                 975

Ala Val Ala Pro Arg Val Arg Ser Pro Pro Arg Ala Ala Ala Ala Pro
            980                 985                 990

Val Val Ser Ala Ser Ala Asp Ala Ala Gly Pro Ala Pro Pro Ala Val
        995                 1000                1005

Pro Val Asp Ala His Arg Ala Pro Arg Ser Arg Met Thr Gln Ala Gln
    1010                1015                1020

Thr Asp Thr Gln Ala Gln Ser Leu Gly Arg Ala Gly Ala Thr Asp Ala
1025                1030                1035                1040

Arg Gly Ser Gly Gly Pro Gly Ala Glu Gly Gly Pro Gly Val Pro Arg
                1045                1050                1055

Gly Thr Asn Thr Pro Gly Ala Ala Pro His Ala Ala Glu Gly Ala Ala
            1060                1065                1070

Gly Ser Asp Ser Gly Pro Ala Ala Ser Ser Ser Ala Ser Ser Ser Ala
        1075                1080                1085

Ala Pro Arg Ser Pro Leu Ala Pro Gln Gly Val Gly Ala Lys Arg Ala
    1090                1095                1100

Ala Pro Arg Arg Ala Pro Asp Ser Asp Ser Gly Asp Arg Gly His Gly
1105                1110                1115                1120

Pro Leu Ala Pro Ala Ser Ala Gly Ala Ala Pro Pro Ser Ala Ser Pro
                1125                1130                1135

Ser Ser Gln Ala Ala Val Ala Ala Ala Ser Ser Ser Ser Ala Ser Ser
            1140                1145                1150

Ser Ser Ala Ser Ser Ser Ser Ala Ser Ser Ser Ser Ala Ser Ser Ser
        1155                1160                1165

Ser Ala Ser Ser Ser Ser Ala Ser Ser Ser Ser Ala Ser Ser Ser Ala
    1170                1175                1180

Gly Gly Ala Gly Gly Ser Val Ala Ser Ala Ser Gly Ala Gly Glu Arg
1185                1190                1195                1200

Arg Glu Thr Ser Leu Gly Pro Arg Ala Ala Ala Pro Arg Gly Pro Arg
                1205                1210                1215

Lys Cys Ala Arg Lys Thr Arg His Ala Glu Gly Gly Pro Glu Pro Gly
            1220                1225                1230

Ala Arg Asp Pro Ala Pro Gly Leu Thr Arg Tyr Leu Pro Ile Ala Gly
        1235                1240                1245

Val Ser Ser Val Val Ala Leu Ala Pro Tyr Val Asn Lys Thr Val Thr
    1250                1255                1260

Gly Asp Cys Leu Pro Val Leu Asp Met Glu Thr Gly His Ile Gly Ala
1265                1270                1275                1280

Tyr Val Val Leu Val Asp Gln Thr Gly Asn Val Ala Asp Leu Leu Arg
                1285                1290                1295

Ala Ala Ala Pro Ala Trp Ser Arg Arg Thr Leu Leu Pro Glu His Ala
            1300                1305                1310

Arg Asn Cys Val Arg Pro Pro Asp Tyr Pro Thr Pro Pro Ala Ser Glu
        1315                1320                1325

Trp Asn Ser Leu Trp Met Thr Pro Val Gly Asn Met Leu Phe Asp Gln
    1330                1335                1340
```

```
Gly Thr Leu Val Gly Ala Leu Asp Phe His Gly Leu Arg Ser Arg His
1345                1350                1355                1360

Pro Trp Ser Arg Glu Gln Gly Ala Pro Ala Pro Ala Gly Asp Ala Pro
                1365                1370                1375

Ala Gly His Gly Glu Gly Gly Gly Gly Ser Gly Gly Gly Gly Ser Gly
            1380                1385                1390

Gly Gly Gly Ser Gly Gly Gly Gly Ser Gly Gly Gly Gly Ser Met Ser
        1395                1400                1405

Ala Glu Gln Arg Lys Lys Lys Lys Thr Thr Thr Thr Thr Gln Gly Arg
    1410                1415                1420

Gly Ala Glu Val Ala Met Ala Asp Glu Asp Gly Gly Arg Leu Arg Ala
1425                1430                1435                1440

Ala Ala Glu Thr Thr Gly Gly Pro Gly Ser Pro Asp Pro Ala Asp Gly
                1445                1450                1455

Pro Pro Pro Thr Pro Asn Pro Asp Arg Arg Pro Ala Ala Arg Pro Gly
            1460                1465                1470

Phe Gly Trp His Gly Gly Pro Glu Glu Asn Glu Asp Glu Ala Asp Asp
        1475                1480                1485

Ala Ala Ala Asp Ala Asp Ala Asp Glu Ala Ala Pro Ala Ser Gly Glu
    1490                1495                1500

Ala Val Asp Glu Pro Ala Ala Asp Gly Val Val Ser Pro Arg Gln Leu
1505                1510                1515                1520

Ala Leu Leu Ala Ser Met Val Asp Glu Ala Val Arg Thr Ile Pro Ser
                1525                1530                1535

Pro Pro Pro Glu Arg Asp Gly Ala Gln Glu Glu Ala Ala Arg Ser Pro
            1540                1545                1550

Ser Pro Pro Arg Thr Pro Ser Met Arg Ala Asp Tyr Gly Glu Glu Asn
        1555                1560                1565

Asp Asp Asp Asp Asp Asp Asp Asp Asp Asp Asp Arg Asp Ala Gly Arg
    1570                1575                1580

Trp Val Arg Gly Pro Glu Thr Thr Ser Ala Val Arg Gly Ala Tyr Pro
1585                1590                1595                1600

Asp Pro Met Ala Ser Leu Ser Pro Arg Pro Pro Ala Pro Arg Arg His
                1605                1610                1615

His His His His His His Arg Arg Arg Arg Ala Pro Arg Arg Arg Ser
            1620                1625                1630

Ala Ala Ser Asp Ser Ser Lys Ser Gly Ser Ser Ser Ser Ala Ser Ser
        1635                1640                1645

Ala Ser Ser Ser Ala Ser Ser Ser Ser Ser Ala Ser Ala Ser Ser Ser
    1650                1655                1660

Asp Asp Asp Asp Asp Asp Asp Ala Ala Arg Ala Pro Ala Ser Ala Ala
1665                1670                1675                1680

Asp His Ala Ala Gly Gly Thr Leu Gly Ala Asp Asp Glu Glu Ala Gly
                1685                1690                1695

Val Pro Ala Arg Ala Pro Gly Ala Ala Pro Arg Pro Ser Pro Pro Arg
            1700                1705                1710

Ala Glu Pro Ala Pro Ala Arg Thr Pro Ala Ala Thr Ala Gly Arg Leu
        1715                1720                1725

Glu Arg Arg Arg Ala Arg Ala Ala Val Ala Gly Arg Asp Ala Thr Gly
    1730                1735                1740

Arg Phe Thr Ala Gly Arg Pro Arg Arg Val Glu Leu Asp Ala Asp Ala
1745                1750                1755                1760

Ala Ser Gly Ala Phe Tyr Ala Arg Tyr Arg Asp Gly Tyr Val Ser Gly
```

```
                1765                1770                1775

Glu Pro Trp Pro Gly Ala Gly Pro Pro Pro Pro Gly Arg Val Leu Tyr
            1780                1785                1790

Gly Gly Leu Gly Asp Ser Arg Pro Gly Leu Trp Gly Ala Pro Glu Ala
        1795                1800                1805

Glu Glu Ala Arg Ala Arg Phe Glu Ala Ser Gly Ala Pro Ala Pro Val
    1810                1815                1820

Trp Ala Pro Glu Leu Gly Asp Ala Ala Gln Gln Tyr Ala Leu Ile Thr
1825                1830                1835                1840

Arg Leu Leu Tyr Thr Pro Asp Ala Glu Ala Met Gly Trp Leu Gln Asn
                1845                1850                1855

Pro Arg Val Ala Pro Gly Asp Val Ala Leu Asp Gln Ala Cys Phe Arg
            1860                1865                1870

Ile Ser Gly Ala Ala Arg Asn Ser Ser Ser Phe Ile Ser Gly Ser Val
        1875                1880                1885

Ala Arg Ala Val Pro His Leu Gly Tyr Ala Met Ala Ala Gly Arg Phe
    1890                1895                1900

Gly Trp Gly Leu Ala His Val Ala Ala Ala Val Ala Met Ser Arg Arg
1905                1910                1915                1920

Tyr Asp Arg Ala Gln Lys Gly Phe Leu Leu Thr Ser Leu Arg Arg Ala
                1925                1930                1935

Tyr Ala Pro Leu Leu Ala Arg Glu Asn Ala Ala Leu Thr Gly Ala Arg
            1940                1945                1950

Thr Pro Asp Asp Gly Gly Asp Ala Asn Arg His Asp Gly Asp Asp Ala
        1955                1960                1965

Arg Gly Lys Pro Ala Ala Ala Ala Ala Pro Leu Pro Ser Ala Ala Ala
    1970                1975                1980

Ser Pro Ala Asp Glu Arg Ala Val Pro Ala Gly Tyr Gly Ala Ala Gly
1985                1990                1995                2000

Val Leu Ala Ala Leu Gly Arg Leu Ser Ala Ala Pro Ala Ser Ala Pro
                2005                2010                2015

Ala Gly Ala Asp Asp Asp Asp Asp Asp Asp Gly Ala Gly Gly Gly Gly
            2020                2025                2030

Gly Gly Arg Arg Ala Glu Ala Gly Arg Val Ala Val Glu Cys Leu Ala
        2035                2040                2045

Ala Cys Arg Gly Ile Leu Glu Ala Leu Ala Glu Gly Phe Asp Gly Asp
    2050                2055                2060

Leu Ala Ala Val Pro Gly Leu Ala Gly Ala Arg Pro Ala Ala Pro Pro
2065                2070                2075                2080

Arg Pro Gly Pro Ala Gly Ala Ala Ala Pro Pro His Ala Asp Ala Pro
                2085                2090                2095

Arg Leu Arg Ala Trp Leu Arg Glu Leu Arg Phe Val Arg Asp Ala Leu
            2100                2105                2110

Val Leu Met Arg Leu Arg Gly Asp Leu Arg Val Ala Gly Gly Ser Glu
        2115                2120                2125

Ala Ala Val Ala Ala Val Arg Ala Val Ser Leu Val Ala Gly Ala Leu
    2130                2135                2140

Gly Pro Ala Leu Pro Arg Ser Pro Arg Leu Leu Ser Ser Ala Ala Ala
2145                2150                2155                2160

Ala Ala Ala Asp Leu Leu Phe Gln Asn Gln Ser Leu
                2165                2170
```

<210> SEQ ID NO 43

```
<211> LENGTH: 6519
<212> TYPE: DNA
<213> ORGANISM: Artificial Sequence
<220> FEATURE:
<223> OTHER INFORMATION: polynucleotide encoding tPA-Flt3L-gD-IPC0-ICP4
      fusion protein

<400> SEQUENCE: 43

atggacgcca tgaagagagg cctgtgctgc gtgctgctgc tgtgcggcgc cgtgttcgtg     60

agccccagcc acgccaccca ggactgcagc ttccagcaca gccccatcag cagcgacttc    120

gccgtgaaga tcagagagct gagcgactac ctgctgcagg actaccccgt gaccgtggcc    180

agcaacctgc aggacgagga gctgtgcggc ggcctgtgga gactggtgct ggcccagaga    240

tggatggaga gactgaagac cgtggccggc agcaagatgc agggcctgct ggagagagtg    300

aacaccgaga tccacttcgt gaccaagtgc gccttccagc ctcccccag ctgcctgagg    360

ttcgtgcaga ccaacatcag cagactgctg caggagacca gcgagcagct ggtggccctg    420

aagccctgga tcaccagaca gaacttcagc agatgcctgg agctgcagtg ccagcccgac    480

agcagcaccc tgcccctcc ctggagcccc agacccctgg aggccaccgc tcccacagcc    540

cctggcagcg ggtccggaag tgggtctgga tccgggcgcg ccaagtatgc tctggccgac    600

ccaagcctga agatggccga ccctaataga ttccggggca agaacctgcc tgtcctggac    660

cagctgaccg atccccctgg cgtgaagcgc gtctaccaca tccagccttc actggaggac    720

ccattccagc cacccagcat ccctattacc gtgtactatg ctgtcctgga acgcgcatgc    780

cgaagtgtgc tgctgcacgc tccctcagag gcacctcaga tcgtcagagg agcctccgat    840

gaagctagga agcatactta caacctgacc attgcctggt atcggatggg cgacaattgt    900

gctatcccca ttacagtgat ggagtacact gaatgccctt ataacaaatc tctgggcgtc    960

tgtcccattc gaacacagcc tcggtggtcc tactatgatt cattcagcgc cgtgtctgag   1020

gacaacctgg gcttcctgat gcacgctcca gcatttgaaa cagccgggac ttatctgaga   1080

ctggtgaaaa tcaatgattg gaccgagatc acacagttta ttctggaaca tagggcccgc   1140

gctagctgca agtacgcact gccactgagg attcctccag cagcttgtct gaccagtaaa   1200

gcttatcagc agggagtgac agtggactca atcggcatgc tgccacgctt cattcccgag   1260

aaccagcgaa ccgtggcact gtacagcctg aagatcgctg ggtggcacgg acccaaaccc   1320

ccttatacta gcaccctgct gccacccgag ctgtccgata ccacaaatgc cacacagccc   1380

gaactggtgc ctgaggaccc agaagacagc gcactgctgg aggaccctgc cggcactgtg   1440

agctcccaga tccctccaaa ctggcatatc cctagcattc aggacgtggc accacaccat   1500

gcaccagcag caccttccaa tccacggaga agggctcaga tggcaccaaa gcgactgcgg   1560

ctgccccaca ttagagacga tgacgccccc ccttcccatc agcctctgtt ttacggagga   1620

ggaggctccg gaggaggagg atctggaggc gggggaagtg gcgggggagg ctcaggggga   1680

ggcggatcta tggaacccag accaggaact tcaagcagag ccgacccagg accagaaaga   1740

cctccccgac agacaccagg cactcagcca gccgcaccac acgcctgggg catgctgaat   1800

gatatgcagt ggctggccag ctccgactct gaggaggaga cagaggtggg catctccgat   1860

gacgatctgc acagggactc cacaagcgag gccggctcca ccgataccga gatgtttgag   1920

gccggcctga tggacgccgc cacccctcca gcccggcccc cagccgagag gcagggctct   1980

ccaacacccg ccgatgccca gggctcctgc ggcggcggcc ctgtgggcga ggaggaggcc   2040

gaggccggcg gcggcggcga cgtgtgcgcc gtgtgcacag acgagatcgc cccacctctg   2100
```

```
agatgccaga gctttccatg tctgcaccca ttctgcatcc catgcatgaa gacctggata   2160
cctctgagga atacctgtcc tctgtgcaat accccagtgg cctacctgat cgtgggcgtg   2220
accgcctctg gctcctttag cacaatcccc atcgtgaacg atcctagaac ccgggtggag   2280
gccgaggccg ccgtgcgggc cggcaccgcc gtggatttca tctggaccgg caacccacgg   2340
acagccccta ggtctctgag cctgggcggc cacaccgtga gagccctgag ccccacaccc   2400
ccttggccag gcacagacga tgaggatgac gacctggccg acgtggatta tgtgccccct   2460
gcccccagaa gagccccccg gagaggcggc ggcggcgccg gcgccacaag aggcacatcc   2520
cagcctgccg ccacaaggcc tgccccacct ggcgccccac ggtcctcctc cagcggcggc   2580
gccccactgc gggccggcgt gggctccggc tccggcggcg gcccagccgt ggccgccgtg   2640
gtgcccagag tggccagcct gcctccagcc gccggcggcg gcagagccca ggccagacgg   2700
gtgggcgagg atgccgccgc cgccgagggc cggacacccc ctgccagaca gccaagagcc   2760
gcccaggagc cccctatcgt gatcagcgac tctccacctc cctccccaag aaggccagcc   2820
ggcccaggcc ctctgtcctt tgtgagctct tcttccgccc aggtgtcttc cggcccaggc   2880
ggcggcggcc tgcctcagtc ctccggcaga gccgccagac cacgggccgc cgtggcccct   2940
agagtgagga gcccccccaag ggccgccgcc gccccagtgg tgtccgcctc cgccgatgcc   3000
gccggcccag ccccacccgc cgtgccagtg gacgcccaca gggccccacg gagcagaatg   3060
acccaggccc agaccgatac ccaggcccag agcctgggca gggccggcgc caccgatgcc   3120
agaggctccg gcggcccagg cgccgagggc ggcccccggcg tgcccagggg cacaaataca   3180
ccaggcgccg ccccccacgc cgccgagggc gccgccggca gcgattccgg ccctgccgcc   3240
tcctcttctg cctccagcag cgccgcccca cgctctcccc tggccccaca gggcgtgggc   3300
gccaagcggg ccgccccaag acgggcccct gactccgatt ccggcgatcg gggccacggc   3360
ccactggccc ctgcctctgc cggcgccgcc cctcctagcg cctccccaag ctctcaggcc   3420
gccgtggccg ccgccagctc cagctccgcc agctcttcct ctgccagctc ctcctctgcc   3480
tcctcctcct ctgcctcttc cagctctgcc agctctagca gcgcctcctc tagctccgcc   3540
tcttctagcg ccggcggcgc cggcggctcc gtggcctctg cctccggcgc cggcgagaga   3600
agagagacct ctctgggccc aagagccgcc gcccccagag gccctagaaa gtgtgccagg   3660
aagaccaggc acgccgaggg cggcccagag ccaggcgccc gcgaccctgc cccaggcctg   3720
acacggtatc tgccaatcgc cggcgtgagc tctgtggtgg ccctggcccc atatgtgaac   3780
aagacagtga caggcgactg tctgccagtg ctggacatgg agacaggcca catcggcgcc   3840
tatgtggtgc tggtggacca gacaggcaat gtggccgatc tgctgagagc cgccgcccct   3900
gcctggtcca gaaggacact gctgccagag cacgccagaa actgcgtgag accacctgac   3960
tatcccacac cacccgcctc tgagtggaat agcctgtgga tgacaccagt gggcaacatg   4020
ctgtttgatc agggcacact ggtgggcgcc ctggatttcc acggcctgag atcccgccac   4080
ccttggtcca gagagcaggg cgcccccgcc ccagccggcg atgccccagc cggccacggc   4140
gagggcggcg gcggctcagg ggggggggc agcggcggag gtggctcagg aggtggaggt   4200
agcggaggtg gcggatctat gtcagcagaa cagaggaaga agaagaaaac aacaacaact   4260
actcagggaa ggggagcaga agtggcaatg gcagacgagg atggaggcag actgagggcc   4320
gccgccgaga caaccggcgg cccaggctct cctgacccag ccgatggccc accaccaaca   4380
cccaacccag accgcagacc agccgccaga cctggctttg gctggcacgg cggcccagag   4440
gagaacgagg atgaggccga cgatgccgcc gccgatgccg acgccgatga ggccgccccc   4500
```

```
gcctccggcg aggccgtgga cgagccagcc gccgacggcg tggtgtctcc tagacagctg   4560
gccctgctgg cctccatggt ggacgaggcc gtgaggacca tcccatctcc tcctccagag   4620
agagatggcg cccaggagga ggccgccagg agcccatccc ccccaagaac ccctagcatg   4680
agagccgact atggcgagga gaacgatgat gacgacgacg atgacgatga tgatgacagg   4740
gacgccggcc gctgggtgcg gggcccagag accacatctg ccgtgagagg cgcctatcct   4800
gacccaatgg cctctctgag cccaagacct cccgccccaa gacggcacca ccaccaccac   4860
caccacagga gacggagggc cccaagaagg cggagcgccg ccagcgactc ctctaagtct   4920
ggctccagca gctctgcctc cagcgccagc tcctctgcca gctcctcctc tagcgccagc   4980
gcctcttcct ccgacgatga tgacgatgat gacgccgcca gggcccctgc ctccgccgcc   5040
gatcacgccg ccggcggcac cctgggcgcc gatgacgagg aggccggcgt gccagccaga   5100
gccccaggcg ccgcccccag gccttctcca ccaagagccg agcccgcccc agccaggacc   5160
ccagccgcca cagccggcag actggagcgg agacgcgcca gagccgccgt ggccggcaga   5220
gatgccacag gcaggtttac cgccggcagg cccagaaggg tggagctgga tgccgatgcc   5280
gcctccggcg ccttttacgc cagatacagg gacggctacg tgagcggcga gccctggcca   5340
ggcgccggcc ctcccccacc tggcagggtg ctgtatggcg gcctgggcga tagcagacct   5400
ggcctgtggg gcgcccctga ggccgaggag gccagagcca gattcgaggc ctctggcgcc   5460
ccagcccccg tgtgggcccc agagctgggc gacgccgccc agcagtacgc cctgatcacc   5520
agactgctgt ataccccaga cgccgaggcc atgggctggc tgcagaaccc tagagtggcc   5580
ccaggcgacg tggccctgga tcaggcctgc ttccggatct ctggcgccgc ccggaacagc   5640
tctagcttta tctccggctc tgtggccaga gccgtgccac acctgggcta cgccatggcc   5700
gccggcaggt tcggctgggg cctggcccac gtagccgccg ccgtggccat gtccagacgg   5760
tatgacagag cccagaaggg ctttctgctg acatctctga ggcgggccta tgcccctctg   5820
ctggccaggg agaatgccgc cctgacaggc gccagaaccc ctgacgacgg cggcgatgcc   5880
aacagacacg atggcgacga tgccagaggc aagccagccg ccgccgccgc ccccctgcca   5940
tccgccgccg cctcccccgc cgatgagaga gccgtgcctg ccggctatgg cgccgccggc   6000
gtgctggccg ccctgggccg gctgtctgcc gccccagcct ccgcccccgc cggcgccgac   6060
gatgatgacg acgatgatgg cgccggcggc ggcggcggcg gcagacgggc cgaggccggc   6120
agggtggccg tggagtgtct ggccgcctgc cgcggcatcc tggaggccct ggccgagggc   6180
tttgatggcg acctggccgc cgtgcccggc ctggccggcg ccagacctgc cgccccacct   6240
agacctggcc ccgccggcgc cgccgccccc cctcacgccg acgccccacg gctgagagcc   6300
tggctgagag agctgagatt cgtgcgggac gccctggtgc tgatgcggct gagaggcgat   6360
ctgcgggtgg ccggcggctc tgaggccgcc gtggccgccg tgagagccgt gtccctggtg   6420
gccggcgccc tgggcccagc cctgcctaga tccccaagac tgctgtcctc cgccgctgcc   6480
gctgccgccg acctgctgtt tcagaaccag agcctgtaa                          6519
```

<210> SEQ ID NO 44
<211> LENGTH: 1073
<212> TYPE: PRT
<213> ORGANISM: Artificial Sequence
<220> FEATURE:
<223> OTHER INFORMATION: SFTS GnGc protein

<400> SEQUENCE: 44

```
Met Met Lys Val Ile Trp Phe Ser Ser Leu Ile Cys Leu Val Ile Gln
1               5                   10                  15

Cys Ser Gly Asp Ser Gly Pro Ile Ile Cys Ala Gly Pro Ile His Ser
            20                  25                  30

Asn Lys Ser Ala Ser Ile Pro His Leu Leu Gly Tyr Ser Glu Lys Ile
        35                  40                  45

Cys Gln Ile Asp Arg Leu Ile His Val Ser Ser Trp Leu Arg Asn His
    50                  55                  60

Ser Gln Phe Gln Gly Tyr Val Gly Gln Arg Gly Gly Arg Ser Gln Val
65                  70                  75                  80

Ser Tyr Tyr Pro Ala Glu Asn Ser Tyr Ser Arg Trp Ser Gly Leu Leu
                85                  90                  95

Ser Pro Cys Asp Ala Asp Trp Leu Gly Met Leu Val Val Lys Lys Ala
            100                 105                 110

Lys Gly Ser Asp Met Ile Val Pro Gly Pro Ser Tyr Lys Gly Lys Val
        115                 120                 125

Phe Phe Glu Arg Pro Thr Phe Asp Gly Tyr Val Gly Trp Gly Cys Gly
    130                 135                 140

Ser Gly Lys Ser Arg Thr Glu Ser Gly Glu Leu Cys Ser Ser Asp Ser
145                 150                 155                 160

Gly Thr Ser Ser Gly Leu Leu Pro Ser Asp Arg Val Leu Trp Ile Gly
                165                 170                 175

Asp Val Ala Cys Gln Pro Met Thr Pro Ile Pro Glu Glu Thr Phe Leu
            180                 185                 190

Glu Leu Lys Ser Phe Ser Gln Ser Glu Phe Pro Asp Ile Cys Lys Ile
        195                 200                 205

Asp Gly Ile Val Phe Asn Gln Cys Glu Gly Glu Ser Leu Pro Gln Pro
    210                 215                 220

Phe Asp Val Ala Trp Met Asp Val Gly His Ser His Lys Ile Ile Met
225                 230                 235                 240

Arg Glu His Lys Thr Lys Trp Val Gln Glu Ser Ser Ser Lys Asp Phe
                245                 250                 255

Val Cys Tyr Lys Glu Gly Thr Gly Pro Cys Ser Glu Ser Glu Glu Lys
            260                 265                 270

Ala Cys Lys Thr Ser Gly Ser Cys Arg Gly Asp Met Gln Phe Cys Lys
        275                 280                 285

Val Ala Gly Cys Glu His Gly Glu Glu Ala Ser Asp Ala Lys Cys Arg
    290                 295                 300

Cys Ser Leu Val His Lys Pro Gly Glu Val Val Val Ser Tyr Gly Gly
305                 310                 315                 320

Met Arg Val Arg Pro Lys Cys Tyr Gly Phe Ser Arg Met Met Ala Thr
                325                 330                 335

Leu Glu Val Asn Pro Pro Glu Gln Arg Ile Gly Gln Cys Thr Gly Cys
            340                 345                 350

His Leu Glu Cys Ile Asn Gly Gly Val Arg Leu Ile Thr Leu Thr Ser
        355                 360                 365

Glu Leu Lys Ser Ala Thr Val Cys Ala Ser His Phe Cys Ser Ser Ala
    370                 375                 380

Thr Ser Gly Lys Lys Ser Thr Glu Ile Gln Phe His Ser Gly Ser Leu
385                 390                 395                 400

Val Gly Lys Thr Ala Ile His Val Lys Gly Ala Leu Val Asp Gly Thr
                405                 410                 415

Glu Phe Thr Phe Glu Gly Ser Cys Met Phe Pro Asp Gly Cys Asp Ala
```

```
            420                 425                 430

Val Asp Cys Thr Phe Cys Arg Glu Phe Leu Lys Asn Pro Gln Cys Tyr
        435                 440                 445

Pro Ala Lys Lys Trp Leu Phe Ile Leu Ile Val Ile Leu Leu Gly Tyr
    450                 455                 460

Ala Gly Leu Met Leu Ile Thr Asn Val Leu Lys Ala Ile Gly Val Trp
465                 470                 475                 480

Gly Ser Trp Val Ile Ala Pro Val Lys Leu Met Phe Ala Ile Ile Lys
                485                 490                 495

Lys Leu Met Arg Thr Val Ser Cys Leu Met Gly Lys Leu Met Asp Arg
            500                 505                 510

Gly Arg Gln Val Ile His Glu Glu Ile Gly Glu Asn Gly Glu Gly Asn
        515                 520                 525

Gln Asp Asp Val Arg Ile Glu Met Ala Arg Pro Arg Arg Val Arg His
    530                 535                 540

Trp Met Tyr Ser Pro Val Ile Leu Thr Ile Leu Ala Ile Gly Leu Ala
545                 550                 555                 560

Glu Gly Cys Asp Glu Met Val His Ala Asp Ser Lys Leu Val Ser Cys
                565                 570                 575

Arg Gln Gly Ser Gly Asn Met Lys Glu Cys Val Thr Thr Gly Arg Ala
            580                 585                 590

Leu Leu Pro Ala Val Asn Pro Gly Gln Glu Ala Cys Leu His Phe Thr
        595                 600                 605

Ala Pro Gly Ser Pro Asp Ser Lys Cys Leu Lys Ile Lys Val Lys Arg
    610                 615                 620

Ile Asn Leu Lys Cys Lys Lys Ser Ser Ser Tyr Phe Val Pro Asp Ala
625                 630                 635                 640

Arg Ser Arg Cys Thr Ser Val Arg Arg Cys Arg Trp Ala Gly Asp Cys
                645                 650                 655

Gln Ser Gly Cys Pro Pro His Phe Thr Ser Asn Ser Phe Ser Asp Asp
            660                 665                 670

Trp Ala Gly Lys Met Asp Arg Ala Gly Leu Gly Phe Ser Gly Cys Ser
        675                 680                 685

Asp Gly Cys Gly Gly Ala Ala Cys Gly Cys Phe Asn Ala Ala Pro Ser
    690                 695                 700

Cys Ile Phe Trp Arg Lys Trp Val Glu Asn Pro His Gly Ile Ile Trp
705                 710                 715                 720

Lys Val Ser Pro Cys Ala Ala Trp Val Pro Ser Ala Val Ile Glu Leu
                725                 730                 735

Thr Met Pro Ser Gly Glu Val Arg Thr Phe His Pro Met Ser Gly Ile
            740                 745                 750

Pro Thr Gln Val Phe Lys Gly Val Ser Val Thr Tyr Leu Gly Ser Asp
        755                 760                 765

Met Glu Val Ser Gly Leu Thr Asp Leu Cys Glu Ile Glu Glu Leu Lys
    770                 775                 780

Ser Lys Lys Leu Ala Leu Ala Pro Cys Asn Gln Ala Gly Met Gly Val
785                 790                 795                 800

Val Gly Lys Val Gly Glu Ile Gln Cys Ser Ser Glu Glu Ser Ala Arg
                805                 810                 815

Thr Ile Lys Lys Asp Gly Cys Ile Trp Asn Ala Asp Leu Val Gly Ile
            820                 825                 830

Glu Leu Arg Val Asp Asp Ala Val Cys Tyr Ser Lys Ile Thr Ser Val
        835                 840                 845
```

```
Glu Ala Val Ala Asn Tyr Ser Ala Ile Pro Thr Thr Ile Gly Gly Leu
    850                 855                 860

Arg Phe Glu Arg Ser His Asp Ser Gln Gly Lys Ile Ser Gly Ser Pro
865                 870                 875                 880

Leu Asp Ile Thr Ala Ile Arg Gly Ser Phe Ser Val Asn Tyr Arg Gly
                885                 890                 895

Leu Arg Leu Ser Leu Ser Glu Ile Thr Ala Thr Cys Thr Gly Glu Val
            900                 905                 910

Thr Asn Val Ser Gly Cys Tyr Ser Cys Met Thr Gly Ala Lys Val Ser
        915                 920                 925

Ile Lys Leu His Ser Ser Lys Asn Ser Thr Ala His Val Arg Cys Lys
    930                 935                 940

Gly Asp Glu Thr Ala Phe Ser Val Leu Glu Gly Val His Ser Tyr Thr
945                 950                 955                 960

Val Ser Leu Ser Phe Asp His Ala Val Val Asp Glu Gln Cys Gln Leu
                965                 970                 975

Asn Cys Gly Gly His Glu Ser Gln Val Thr Leu Lys Gly Asn Leu Ile
            980                 985                 990

Phe Leu Asp Val Pro Lys Phe Val Asp Gly Ser Tyr Met Gln Thr Tyr
        995                 1000                1005

His Ser Thr Val Pro Thr Gly Ala Asn Ile Pro Ser Pro Thr Asp Trp
    1010                1015                1020

Leu Asn Ala Leu Phe Gly Asn Gly Leu Ser Arg Trp Ile Leu Gly Val
1025                1030                1035                1040

Ile Gly Val Leu Leu Gly Gly Leu Ala Leu Phe Phe Leu Ile Met Ser
                1045                1050                1055

Leu Phe Lys Leu Gly Thr Lys Gln Val Phe Arg Ser Arg Thr Lys Leu
            1060                1065                1070

Ala
```

```
<210> SEQ ID NO 45
<211> LENGTH: 245
<212> TYPE: PRT
<213> ORGANISM: Artificial Sequence
<220> FEATURE:
<223> OTHER INFORMATION: SFTS NP protein

<400> SEQUENCE: 45

Met Ser Glu Trp Ser Arg Ile Ala Val Glu Phe Gly Glu Gln Gln Leu
1               5                   10                  15

Asn Leu Ser Glu Leu Glu Asp Phe Ala Arg Glu Leu Ala Tyr Glu Gly
            20                  25                  30

Leu Asp Pro Ala Leu Ile Ile Lys Lys Leu Lys Glu Thr Gly Gly Asp
        35                  40                  45

Asp Trp Val Lys Asp Thr Lys Phe Ile Ile Val Phe Ala Leu Thr Arg
    50                  55                  60

Gly Asn Lys Ile Val Lys Ala Ser Gly Lys Met Ser Asn Ser Gly Ser
65                  70                  75                  80

Lys Arg Leu Met Ala Leu Gln Glu Lys Tyr Gly Leu Val Glu Arg Ala
                85                  90                  95

Glu Thr Arg Leu Ser Ile Thr Pro Val Arg Val Ala Gln Ser Leu Pro
            100                 105                 110

Thr Trp Thr Cys Ala Ala Ala Ala Ala Leu Lys Glu Tyr Leu Pro Val
        115                 120                 125
```

```
Gly Pro Ala Val Met Asn Leu Lys Val Glu Asn Tyr Pro Pro Glu Met
    130                 135                 140

Met Cys Met Ala Phe Gly Ser Leu Ile Pro Thr Ala Gly Val Ser Glu
145                 150                 155                 160

Ala Thr Thr Lys Thr Leu Met Glu Ala Tyr Ser Leu Trp Gln Asp Ala
                165                 170                 175

Phe Thr Lys Thr Ile Asn Val Lys Met Arg Gly Ala Ser Lys Thr Glu
            180                 185                 190

Val Tyr Asn Ser Phe Arg Asp Pro Leu His Ala Ala Val Asn Ser Val
        195                 200                 205

Phe Phe Pro Asn Asp Val Arg Val Lys Trp Leu Lys Ala Lys Gly Ile
    210                 215                 220

Leu Gly Pro Asp Gly Val Pro Ser Arg Ala Ala Glu Val Ala Ala Ala
225                 230                 235                 240

Ala Tyr Arg Asn Leu
                245


<210> SEQ ID NO 46
<211> LENGTH: 293
<212> TYPE: PRT
<213> ORGANISM: Artificial Sequence
<220> FEATURE:
<223> OTHER INFORMATION: SFTS NSs protein

<400> SEQUENCE: 46

Met Ser Leu Ser Lys Ser Ser Asn Val Asp Leu Lys Ser Val Ala Met
1               5                   10                  15

Asn Ala Asn Thr Val Arg Leu Glu Pro Ser Leu Gly Glu Tyr Pro Thr
            20                  25                  30

Leu Arg Arg Asp Leu Val Glu Cys Ser Cys Ser Val Leu Thr Leu Ser
        35                  40                  45

Met Val Lys Arg Met Gly Lys Met Thr Asn Thr Val Trp Leu Phe Gly
    50                  55                  60

Asn Pro Lys Asn Pro Leu His Gln Leu Glu Pro Gly Leu Glu Gln Leu
65                  70                  75                  80

Leu Asp Met Tyr Tyr Lys Asp Met Arg Cys Tyr Ser Gln Arg Glu Leu
                85                  90                  95

Ser Ala Leu Arg Trp Pro Ser Gly Lys Pro Ser Val Trp Phe Leu Gln
            100                 105                 110

Ala Ala His Met Phe Phe Ser Ile Lys Asn Ser Trp Ala Met Glu Thr
        115                 120                 125

Gly Lys Glu Asn Trp Arg Gly Leu Phe His Arg Ile Thr Lys Gly Gln
    130                 135                 140

Lys Tyr Leu Phe Glu Gly Asp Met Ile Leu Asp Ser Leu Glu Ala Ile
145                 150                 155                 160

Glu Lys Arg Arg Leu Arg Leu Gly Leu Pro Glu Ile Leu Ile Thr Gly
                165                 170                 175

Leu Ser Pro Ile Leu Asp Val Ala Leu Leu Gln Ile Glu Ser Leu Ala
            180                 185                 190

Arg Leu Arg Gly Met Ser Leu Asn His His Leu Phe Thr Ser Ser Ser
        195                 200                 205

Leu Arg Lys Pro Leu Leu Asp Cys Trp Asp Phe Phe Ile Pro Val Arg
    210                 215                 220

Lys Lys Lys Thr Asp Gly Ser Tyr Ser Val Leu Asp Glu Asp Asp Glu
225                 230                 235                 240
```

```
Pro Gly Ala Leu Gln Gly Tyr Pro His Leu Met Ala His Tyr Leu Asn
                245                 250                 255

Arg Cys Pro Phe His Asn Leu Ile Arg Phe Asp Glu Glu Leu Arg Thr
            260                 265                 270

Ala Ala Leu Asn Thr Ile Trp Gly Arg Asp Trp Pro Ala Ile Gly Asp
        275                 280                 285

Leu Pro Lys Glu Val
    290


<210> SEQ ID NO 47
<211> LENGTH: 3222
<212> TYPE: DNA
<213> ORGANISM: Artificial Sequence
<220> FEATURE:
<223> OTHER INFORMATION: polynucleotide encoding SFTS GnGc protein

<400> SEQUENCE: 47

atgatgaaag tgatttggtt ctcctctctg atttgtctgg tcattcagtg tagcggggat     60

tctggaccta ttatctgtgc tgggccaatc cacagcaaca agagcgcctc catcccccac    120

ctgctgggct actccgagaa gatctgccag atcgaccgcc tgatccacgt gagctcctgg    180

ctgcggaacc acagccagtt ccagggatac gtgggacaga ggggaggccg cagccaggtg    240

tcctactatc cagccgagaa ttcttatagc agatggtccg gcctgctgtc tccatgtgac    300

gcagattggc tgggcatgct ggtggtgaag aaggccaagg gctctgatat gatcgtgcct    360

ggcccaagct acaagggcaa ggtgttcttt gagcggccca ccttcgacgg atatgtggga    420

tggggatgcg gatctggcaa gagcaggaca gagtccggcg agctgtgcag cagcgattct    480

ggcacctcct ctggcctgct gcctagcgat cgcgtgctgt ggatcggcga cgtggcatgc    540

cagccaatga cacccatccc tgaggagaca ttcctggagc tgaagtcctt ctctcagagc    600

gagtttcctg atatctgcaa gatcgacggc atcgtgttca atcagtgtga gggcgagagc    660

ctgccacagc cctttgatgt ggcctggatg gacgtgggcc actcccacaa gatcatcatg    720

cgggagcaca agaccaagtg ggtgcaggag agctcctcta aggacttcgt gtgctacaag    780

gagggcacag gcccatgttc cgagtctgag gagaaggcct gcaagaccag cggctcctgt    840

agaggcgata tgcagttttg caaggtggca ggatgtgagc acggagagga ggcctctgac    900

gccaagtgca ggtgtagcct ggtgcacaag ccaggagagg tggtggtgtc ttacggagga    960

atgcgggtgc ggcccaagtg ctatggcttc agcagaatga tggccacact ggaggtgaac   1020

ccccctgagc agaggatcgg ccagtgcacc ggctgtcacc tggagtgtat caatggcggc   1080

gtgaggctga tcaccctgac aagcgagctg aagtccgcca cagtgtgcgc cagccacttc   1140

tgtagctccg ccacatctgg caagaagagc accgagatcc agtttcactc tggcagcctg   1200

gtgggcaaga ccgcaatcca cgtgaagggc gccctggtgg atggcacaga gttcaccttt   1260

gagggctcct gcatgttccc agacggctgt gatgccgtgg actgcacctt ctgtagagag   1320

tttctgaaga acccacagtg ctaccccgcc aagaagtggc tgtttatcct gatcgtgatc   1380

ctgctgggct atgccggcct gatgctgatc acaaatgtgc tgaaggccat cggcgtgtgg   1440

ggatcttggg tcatcgcacc cgtgaagctg atgtttgcca tcatcaagaa gctgatgagg   1500

accgtgtcct gcctgatggg caagctgatg gacaggggcc ggcaggtcat ccacgaggag   1560

atcggcgaga acggcgaggg caatcaggac gatgtgcgga tcgagatggc cagacctcgg   1620

agagtgaggc actggatgta cagcccagtg atcctgacaa tcctggcaat cggcctggca   1680

gagggatgcg atgagatggt gcacgccgac tccaagctgg tgtcttgccg ccagggctcc   1740
```

```
ggcaacatga aggagtgcgt gaccacaggc cgggccctgc tgcctgcagt gaatccaggc   1800

caggaggcat gtctgcactt caccgcacca ggctcccctg actctaagtg cctgaagatc   1860

aaggtgaagc gcatcaacct gaagtgtaag aagtctagct cctattttgt gcccgatgcc   1920

cggagcagat gcacatccgt gaggcgctgt agatgggcag gcgactgcca gagcggctgt   1980

ccaccccact tcacctccaa ttcttttagc gacgattggg ccggcaagat ggatagagca   2040

ggcctgggct tcagcggatg ctccgacgga tgtggaggag cagcatgcgg atgtttcaac   2100

gcagcccccct cctgcatctt ttggaggaag tgggtggaga atcctcacgg catcatctgg   2160

aaggtgagcc catgtgcagc atgggtgccc tccgccgtga tcgagctgac aatgccatcc   2220

ggagaggtgc gcaccttcca ccccatgtct ggcatcccta cacaggtgtt taagggcgtg   2280

agcgtgacct acctgggcag cgatatggag gtgtccggcc tgaccgacct gtgcgagatc   2340

gaggagctga agtccaagaa gctggccctg gcaccttgta accaggcagg aatgggagtg   2400

gtgggcaagg tcggcgagat ccagtgctct agcgaggaga gcgcccgcac aatcaagaag   2460

gatggctgta tctggaacgc agacctggtg ggaatcgagc tgagggtgga cgatgccgtg   2520

tgctactcta agatcaccag cgtggaggcc gtggccaatt attccgccat ccctaccaca   2580

atcggcggcc tgcggttcga gagatctcac gatagccagg gcaagatctc cggctctcca   2640

ctggacatca ccgccatccg cggcagcttt tccgtgaact acaggggcct gcgcctgtct   2700

ctgagcgaga tcaccgccac atgcaccggc gaggtgacaa acgtgagcgg ctgctattct   2760

tgtatgaccg gcgccaaggt gtctatcaag ctgcactcct ctaagaacag cacagcccac   2820

gtgcggtgta agggcgatga gacagccttc tccgtgctgg agggcgtgca ctcttataca   2880

gtgtccctgt cttttgatca cgccgtggtg gacgagcagt gccagctgaa ctgtggcggc   2940

cacgagagcc aggtgaccct gaagggcaat ctgatcttcc tggatgtgcc aaagtttgtg   3000

gacggcagct acatgcagac atatcactcc acagtgccca ccggcgccaa tatcccttcc   3060

ccaaccgact ggctgaacgc cctgttcggc aatggcctgt ctaggtggat cctgggcgtg   3120

atcggcgtgc tgctgggagg cctggccctg ttctttctga tcatgtctct gttcaaactg   3180

ggcactaagc aggtctttcg gtcccgcaca aaactggctt aa                      3222
```

```
<210> SEQ ID NO 48
<211> LENGTH: 735
<212> TYPE: DNA
<213> ORGANISM: Artificial Sequence
<220> FEATURE:
<223> OTHER INFORMATION: polynucleotide encoding SFTS NP protein

<400> SEQUENCE: 48

atgtcggagt ggtccaggat tgcagtggag tttggtgagc agcagctcaa tttgtctgag     60

cttgaggatt tcgcgagaga actggcctat gaaggccttg accctgcttt gatcatcaag    120

aagctgaagg agacaggtgg agatgattgg gtgaaggata caaagttcat cattgtcttt    180

gccctgactc gaggcaacaa gatcgtcaag gcatcaggga aaatgtcaaa ctcagggtcc    240

aagaggttga tggcactcca agagaaatat ggactggttg agagggcaga gaccaggctc    300

tcaatcactc ctgtgagggt tgcgcagagc cttcccactt ggacatgtgc tgcagcagca    360

gccttgaagg agtatctccc tgtggggcca gccgtcatga acctgaaggt cgagaattat    420

ccccctgaga tgatgtgcat ggcctttgga tccctgattc caactgcggg ggtatctgaa    480

gccacaacca agaccctgat ggaggcctac tctctgtggc aagatgcctt caccaagact    540
```

```
atcaatgtga agatgcgcgg agccagcaag acagaagttt acaactcctt cagggaccct    600

cttcatgctg ctgtgaactc tgtcttcttt cccaatgatg ttcgggtaaa gtggctgaag    660

gccaagggga tccttggccc agatggggtc cccagcagag ctgctgaggt tgctgctgct    720

gcttacagaa acctg                                                     735
```

<210> SEQ ID NO 49
<211> LENGTH: 882
<212> TYPE: DNA
<213> ORGANISM: Artificial Sequence
<220> FEATURE:
<223> OTHER INFORMATION: polynucleotide encoding SFTS NSs protein

<400> SEQUENCE: 49

```
atgagcctga gtaagagcag caatgtggat ctgaaaagcg tcgcaatgaa tgccaacacc     60

gtccgcctgg aaccatcact gggggaatac cctaccctga ggcgggacct ggtggagtgc    120

agctgttccg tgctgacact gtctatggtg aagaggatgg gcaagatgac caacacagtg    180

tggctgttcg gcaaccccaa gaatcctctg caccagctgg agccaggcct ggagcagctg    240

ctggacatgt actataagga tatgaggtgc tactctcaga gggagctgag cgccctgagg    300

tggccctccg gcaagcccag cgtgtggttt ctccaggccg cccacatgtt ctttagcatc    360

aagaactcct gggctatgga gacaggcaag gagaattggc ggggcctgtt ccacagaatc    420

acaaagggcc agaagtatct gtttgagggc gacatgatcc tggatagcct ggaggcaatc    480

gagaagaggc gcctgaggct gggcctgcca gagatcctga tcaccggcct gtcccctatc    540

ctggacgtgg ccctgctcca gatcgagtcc ctggcccggc tgagaggcat gtctctgaat    600

caccacctgt tcaccagctc ctctctgcgg aagccactgc tggactgctg ggatttcttt    660

atccccgtgc ggaagaagaa gaccgacggc tcttatagcg tgctggatga ggacgatgag    720

cccggcgccc tccagggcta cccacacctg atggcccact atctgaacag gtgtcccttc    780

cacaatctga tcaggtttga tgaggagctg cgcacagccg ccctgaatac catctggggg    840

cgggactggc ctgctatcgg cgacctgcct aaggaagtgt aa                       882
```

<210> SEQ ID NO 50
<211> LENGTH: 5
<212> TYPE: PRT
<213> ORGANISM: Artificial Sequence
<220> FEATURE:
<223> OTHER INFORMATION: (GGGGS)n linker peptide unit

<400> SEQUENCE: 50

```
Gly Gly Gly Gly Ser
1               5
```

<210> SEQ ID NO 51
<211> LENGTH: 6
<212> TYPE: PRT
<213> ORGANISM: Artificial Sequence
<220> FEATURE:
<223> OTHER INFORMATION: (GSSGGS)n linker peptide unit

<400> SEQUENCE: 51

```
Gly Ser Ser Gly Gly Ser
1               5
```

<210> SEQ ID NO 52
<211> LENGTH: 18
<212> TYPE: PRT
<213> ORGANISM: Artificial Sequence

```
<220> FEATURE:
<223> OTHER INFORMATION: linker peptide

<400> SEQUENCE: 52

Lys Glu Ser Gly Ser Val Ser Ser Glu Gln Leu Ala Gln Phe Arg Ser
1               5                   10                  15

Leu Asp


<210> SEQ ID NO 53
<211> LENGTH: 14
<212> TYPE: PRT
<213> ORGANISM: Artificial Sequence
<220> FEATURE:
<223> OTHER INFORMATION: linker peptide

<400> SEQUENCE: 53

Glu Gly Lys Ser Ser Gly Ser Gly Ser Glu Ser Lys Ser Thr
1               5                   10


<210> SEQ ID NO 54
<211> LENGTH: 12
<212> TYPE: PRT
<213> ORGANISM: Artificial Sequence
<220> FEATURE:
<223> OTHER INFORMATION: linker peptide

<400> SEQUENCE: 54

Gly Ser Ala Gly Ser Ala Ala Gly Ser Gly Glu Phe
1               5                   10


<210> SEQ ID NO 55
<211> LENGTH: 5
<212> TYPE: PRT
<213> ORGANISM: Artificial Sequence
<220> FEATURE:
<223> OTHER INFORMATION: (EAAAK)n linker peptide unit

<400> SEQUENCE: 55

Glu Ala Ala Ala Lys
1               5


<210> SEQ ID NO 56
<211> LENGTH: 12
<212> TYPE: PRT
<213> ORGANISM: Artificial Sequence
<220> FEATURE:
<223> OTHER INFORMATION: linker peptide

<400> SEQUENCE: 56

Cys Arg Arg Arg Arg Arg Arg Glu Ala Glu Ala Cys
1               5                   10


<210> SEQ ID NO 57
<211> LENGTH: 46
<212> TYPE: PRT
<213> ORGANISM: Artificial Sequence
<220> FEATURE:
<223> OTHER INFORMATION: linker peptide

<400> SEQUENCE: 57

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
```

```
        35                  40                  45


<210> SEQ ID NO 58
<211> LENGTH: 8
<212> TYPE: PRT
<213> ORGANISM: Artificial Sequence
<220> FEATURE:
<223> OTHER INFORMATION: linker peptide

<400> SEQUENCE: 58

Gly Gly Gly Gly Gly Gly Gly Gly
1               5


<210> SEQ ID NO 59
<211> LENGTH: 6
<212> TYPE: PRT
<213> ORGANISM: Artificial Sequence
<220> FEATURE:
<223> OTHER INFORMATION: linker peptide

<400> SEQUENCE: 59

Gly Gly Gly Gly Gly Gly
1               5


<210> SEQ ID NO 60
<211> LENGTH: 13
<212> TYPE: PRT
<213> ORGANISM: Artificial Sequence
<220> FEATURE:
<223> OTHER INFORMATION: linker peptide

<400> SEQUENCE: 60

Ala Glu Ala Ala Ala Lys Glu Ala Ala Ala Ala Lys Ala
1               5                   10


<210> SEQ ID NO 61
<211> LENGTH: 5
<212> TYPE: PRT
<213> ORGANISM: Artificial Sequence
<220> FEATURE:
<223> OTHER INFORMATION: linker peptide

<400> SEQUENCE: 61

Pro Ala Pro Ala Pro
1               5


<210> SEQ ID NO 62
<211> LENGTH: 17
<212> TYPE: PRT
<213> ORGANISM: Artificial Sequence
<220> FEATURE:
<223> OTHER INFORMATION: linker peptide

<400> SEQUENCE: 62

Val Ser Gln Thr Ser Lys Leu Thr Arg Ala Glu Thr Val Phe Pro Asp
1               5                   10                  15

Val


<210> SEQ ID NO 63
<211> LENGTH: 6
<212> TYPE: PRT
<213> ORGANISM: Artificial Sequence
<220> FEATURE:
<223> OTHER INFORMATION: linker peptide

<400> SEQUENCE: 63
```

Pro Leu Gly Leu Trp Ala
1 5

<210> SEQ ID NO 64
<211> LENGTH: 10
<212> TYPE: PRT
<213> ORGANISM: Artificial Sequence
<220> FEATURE:
<223> OTHER INFORMATION: linker peptide

<400> SEQUENCE: 64

Thr Arg His Arg Gln Pro Arg Gly Trp Glu
1 5 10

<210> SEQ ID NO 65
<211> LENGTH: 10
<212> TYPE: PRT
<213> ORGANISM: Artificial Sequence
<220> FEATURE:
<223> OTHER INFORMATION: linker peptide

<400> SEQUENCE: 65

Ala Gly Asn Arg Val Arg Arg Ser Val Gly
1 5 10

<210> SEQ ID NO 66
<211> LENGTH: 8
<212> TYPE: PRT
<213> ORGANISM: Artificial Sequence
<220> FEATURE:
<223> OTHER INFORMATION: linker peptide

<400> SEQUENCE: 66

Arg Arg Arg Arg Arg Arg Arg Arg
1 5

<210> SEQ ID NO 67
<211> LENGTH: 4
<212> TYPE: PRT
<213> ORGANISM: Artificial Sequence
<220> FEATURE:
<223> OTHER INFORMATION: linker peptide

<400> SEQUENCE: 67

Gly Phe Leu Gly
1

<210> SEQ ID NO 68
<211> LENGTH: 31
<212> TYPE: PRT
<213> ORGANISM: Artificial Sequence
<220> FEATURE:
<223> OTHER INFORMATION: linker peptide

<400> SEQUENCE: 68

Gly Ser Ser Gly Gly Ser Gly Ser Ser Gly Gly Ser Gly Gly Gly Asp
1 5 10 15

Glu Ala Asp Gly Ser Arg Gly Ser Gln Lys Ala Gly Val Asp Glu
20 25 30

VACCINE ADJUVANT

SEQUENCE LISTING

The Sequence Listing submitted in text format (.txt) filed on Jul. 31, 2020, named "SequenceListing.txt", created on Jul. 21, 2020 (171 KB), is incorporated herein by reference.

TECHNICAL FIELD

This application claims priority to Korean Patent Application No. 2018-0013329 filed Feb. 2, 2018. The specification of the above application is incorporated herein by reference in its entirety.

The present invention relates to a vaccine adjuvant, and more specifically, to a novel vaccine adjuvant that can maximize the therapeutic effect of anticancer vaccines, etc. by selectively enhancing a T cell-specific immune response.

BACKGROUND

Vaccines are drugs used to generate an immune response to antigens for the defense against pathogenic infections and recently developed vaccines mainly use recombinant proteins as antigens. Recombinant proteins are safe and less toxic compared to killed vaccines or attenuated live vaccines, but the recombinant proteins have low immunogenicity. Therefore, vaccine adjuvants are used together so as to provide sufficient immunity to defend against infection.

Vaccine adjuvants are classified into three types, i.e., a carrier of an antigen, an immunostimulant, and one which acts as a matrix for an antigen while stimulating an immune response according to the mechanism of action. The effective use of vaccine adjuvants can allow to obtain various effects, such as: (1) increase the immunogenicity of recombinant antigens, (2) reduce the dose of antigens or reduce the number of immunizations, and (3) improve immunogenicity in infants and elderly people with weak immunity. However, despite the usefulness of these vaccine adjuvants, there are still few vaccine adjuvants licensed for use in human vaccines, and this is because there are a number of things to consider in order to be selected as a vaccine adjuvant. The ideal conditions for vaccine adjuvants are that they should be safe, excellent in drug resistance, simple to manufacture, and low in production cost. Additionally, vaccine adjuvants should have a long half-life in vivo and be biodegradable, and should not induce any immune response against the immune adjuvants themselves. In particular, among them, the safety issue of vaccine adjuvant is most important.

The vaccine adjuvants currently approved in Europe and USA for use in vaccines include an aluminum salt, MF59, AS03, AS04, etc. Aluminum salts are mainly used in the form of $Al(OH)_3$ or $AlPO_4$, which are thought to exhibit an immunostimulating effect by adsorbing to and slowly releasing protein antigens. Recently, however, aluminum salts have been shown to activate dendritic cells and promote secretion of cytokines (e.g., IL-1β and IL-18). Aluminum salts are widely used in several vaccines and are thought to be very safe, but it is assumed that aluminum salts may cause allergic reactions and have neurotoxicity. In addition, aluminum salts strongly induce antibody-mediated humoral immune responses, but aluminum salts have disadvantages in that they hardly induce cell-mediated immune responses and cryopreservation is not possible.

The MF59 (Ott et al., *Pharm Biotechnol.* 6: 277-296, 1995) of Novartis and the AS03 (Li et al., *J. Virol.* 80(3): 1414-1426, 2006) of GSK are both immune adjuvants in the form of an oil-in-water (o/w) emulsion with squalene as the basic ingredient. The o/w emulsion immune adjuvant activates antigen-presenting cells to stimulate antigen uptake and cytokine secretion, increases expression of chemokine receptors, thereby increasing migration of antigen-presenting cells. MF59 and AS03 were used for the purpose of increasing the immunogenicity of the antigens in the vaccine against the new type of influenza virus pandemic in 2009 and reducing the amount of antigen used, through clinical trials, MF59 and AS03 were confirmed to have effects of increasing the rate of antibody production and cross-defense effect. In addition to squalene, various emulsion immune adjuvants have been developed using emulsions prepared in nature that can be used in humans, but the commercialization of these emulsion immune adjuvants is difficult due to excessive immune responses and toxicities. Particulate carriers such as liposomes, immunostimulatory complexes, and virus-like particles are also being developed as immune adjuvants, and these are usually developed as vaccine carriers and adjuvants by encapsulating the antigens. Particularly, liposomes have been actively studied. Liposomes are synthetic spheres constituting a lipid layer that can encapsulate antigens and simultaneously act as a vaccine delivery and immune adjuvant, and the activity of liposomes varies depending on the number, charge, composition, and preparation method of the lipid layer. Liposomes enhance humoral immunity and cellular immunity against protein and polysaccharide antigens. However, the use of liposomes is limited due to difficulties in preparation, stability, etc., and it is necessary to add an immunostimulatory component in order to have strong actions of immune activity, especially because the role of the immunostimulatory component is closer to an antigenic carrier than an adjuvant to enhance immune response. Currently, GSK has developed an immune adjuvant, AS01B, in which monophosphoryl lipid A (MPL) is added to liposomes, and is now attempting to develop the immune adjuvant to be applicable as a vaccine adjuvant for patients with tuberculosis and malaria diseases (WO96/33739A).

However, although these vaccine adjuvants enhance the cell-mediated immune response, most of these vaccine adjuvants have been developed to enhance the immune response of the vaccine composition for the prevention of infectious diseases (e.g., viruses, etc.), which require mainly humoral immunity, and thus the effects of vaccines for the prevention and treatment of diseases that require cell-mediated immune responses (e.g., cancer, etc.) have not yet been confirmed.

SUMMARY

As described above, there is still an urgent need for the development of a vaccine adjuvant, by enhancing T-cell specific immune responses, which is effective for the prevention and treatment of diseases that require enhancing cell-mediated immune responses (e.g., cancer, etc.) as well as the prevention and treatment of conventional infectious disease caused by the infection of viruses, etc. In this regard, the present inventors, to solve the various issues including those described above, provides a novel vaccine adjuvant that can enhance the effects of the vaccine via the enhancement of T cell immune response-specific immunity. However, the present invention is not limited by the purpose.

In an aspect of the present invention, there is provided a vaccine adjuvant for stimulating a T lymphocyte-specific immune response, in which the vaccine adjuvant includes a polynucleotide encoding an IL-12 protein and a polynucleotide encoding an IL-21 protein as active ingredients.

In another aspect of the present invention, there is provided a vaccine adjuvant for stimulating a T lymphocyte-specific immune response, in which the vaccine adjuvant includes an IL-12 protein and an IL-21 protein as active ingredients.

According to still another aspect of the present disclosure, there is provided a vaccine composition for stimulating a T lymphocyte-specific immune response, in which the vaccine composition includes the vaccine adjuvant and an antigen for immunization as active ingredients.

According to still another aspect of the present disclosure, there is provided a method for stimulating a T lymphocyte-specific immune response by the vaccine composition, in which the method includes administering, to an individual, the vaccine adjuvant along with a vaccine composition, or before or after the administration of the vaccine composition.

Effect of the Invention

The vaccine adjuvant according to an embodiment of the present invention significantly enhances the T cell-specific immune response by selectively increasing T cells that specifically respond to antigens without affecting antibody production. Thus, the vaccine adjuvant can be usefully used as an immunotherapeutic agent for treating cancer such as cervical cancer as well as for treating infectious diseases by the infection of various infectious viruses through intensifying the cellular immune.

BRIEF DESCRIPTION OF THE DRAWINGS

Exemplary embodiments can be understood in more detail from the following description taken in conjunction with the accompanying drawings, in which:

FIG. 2 is schematic diagrams showing the gene construct of BD-14, which is a 14-valent HPV DNA vaccine prepared in accordance with an exemplary embodiment;

FIG. 3 is a schematic diagram showing the gene construct of a CMV DNA vaccine, which is prepared in accordance with an exemplary embodiment;

FIG. 4*a* is a schematic diagram showing the gene construct of BD-02B, which is included in a HSV-2 DNA vaccine prepared in accordance with an exemplary embodiment; and FIG. 4*b* is a schematic diagram showing the gene construct of BD-02C, which is included in a HSV-2 DNA vaccine prepared in accordance with an exemplary embodiment;

FIG. 5 is a schematic diagram showing the gene construct of an SFTS DNA vaccine, which is prepared in accordance with an exemplary embodiment;

FIG. 6 is a graph showing the results of ELISPOT analysis of antigen-specific T cell immune responses when the conventional 2-valent HPV DNA vaccine is administered alone or in combination with the vaccine adjuvant BD-121 in accordance with an exemplary embodiment;

FIG. 12*a* shows the administration schedule for a HSV-2 DNA vaccine (BD02) prepared in accordance with an exemplary embodiment and BD-121, which is a vaccine adjuvant prepared in accordance with an exemplary embodiment;

FIG. 12*b* is a graph showing the changes in the pathological index of HSV-2 over time, in a group administered with a HSV-2 DNA vaccine (BD02) prepared in accordance with an exemplary embodiment alone (BD-02B+BD-02C) and a group administered in combination with BD-121, which is a vaccine adjuvant prepared in accordance with an exemplary embodiment (BD02 DP);

FIG. 12*c* is graphs showing the changes in the survival rate of experimental animals over time, in a group administered with a HSV-2 DNA vaccine (BD02) prepared in accordance with an exemplary embodiment alone (BD-02B+BD-02C) and a group administered in combination with BD-121, which is a vaccine adjuvant prepared in accordance with an exemplary embodiment (BD02 DP);

DETAILED DESCRIPTION OF THE INVENTION

Figures 1A, 1B:
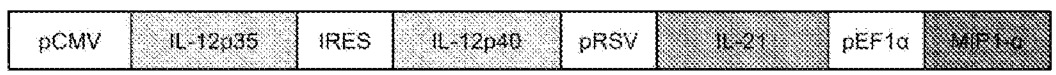
FIG. 1*a* is a schematic diagram showing the gene construct of BD-121, which is a vaccine adjuvant in accordance with an exemplary embodiment.
FIG. 1*b* is a schematic diagram showing the gene construct of BD-121A, which is a vaccine adjuvant in accordance with an exemplary embodiment.

In an aspect of the present invention, a vaccine adjuvant for promoting a T lymphocyte-specific immune response includes a polynucleotide encoding an IL-12 protein and a polynucleotide encoding an IL-21 protein as active ingredients.

In particular, the vaccine adjuvant may include at least one selected from the group consisting of the followings:

one to three vectors, each of which include: polynucleotides that respectively encode a p35 chain (IL-12p35) and a p40 chain (IL-12p40) that constitute the IL-12 protein; and a polynucleotide that encodes the IL-21 protein; and a mRNA molecules, each of which encode the IL-12p35, IL-12p40, and IL-21 proteins.

Furthermore, it is possible that in the above-described vaccine adjuvant, part of the IL-21p35, IL-12p40, and IL-21 may be included as proteins and the rest may be used as a mixture of heterogeneous molecules, such as expression vector and/or mRNA molecules.

In particular, the one to three vectors may include a gene construct in which the polynucleotide is operably linked to a control sequence (e.g., a promoter) so that the IL-21p35, IL-12p40, and IL-21 can be expressed. The vaccine adjuvant may be constituted as one to three vectors such that polynucleotides, each of which encode the IL-21p35, IL-12p40, and IL-21, are inserted into an individual expression vector (a triple vector system), or are inserted into one or two expression vectors (a single vector or dual vector system). A specific exemplary embodiment of such a single vector system to a triple vector system is as follows:

i) a $4^{th}$ expression vector, which includes a $1^{st}$ gene construct to a $3^{rd}$ gene construct in which polynucleotides that encode the IL-21p35, IL-12p40, and IL-21 proteins, respectively, are each operably linked to a promoter;

ii) a $2^{nd}$ expression vector to a $4^{th}$ expression vector, which include the $1^{st}$ gene construct to the $3^{rd}$ gene construct, respectively;

iii) a $5^{th}$ expression vector and a $6^{th}$ expression vector, each of which include two of the Pt gene construct to the $3^{rd}$ gene construct and the remaining one gene construct, respectively;

iv) a fusion protein in which an IL-21 is linked to any one of the IL-12p35 and the IL-12p40; and a peptide between the IL-12p35 and the IL-12p40 which is not included in the fusion protein;

v) a $7^{th}$ expression vector, which includes a $4^{th}$ gene construct in which a polynucleotide encoding the fusion protein of iv) is operably linked to a promoter, and a $5^{th}$ gene construct, in which a polynucleotide encoding the peptide of iv) is operably linked to a promoter;

vi) an $8^{th}$ expression vector and a $9^{th}$ expression vector, which include the $4^{th}$ gene construct and the $5^{th}$ gene construct, respectively;

vii) a $10^{th}$ expression vector which includes: a $6^{th}$ gene construct in which at least two of the polynucleotides that encode the IL-12p35, IL-12p40, and IL-21 proteins, respectively, are linked to an internal ribosome entry site (IRES); and optionally a $7^{th}$ gene construct in which the remaining polynucleotide, among the three polynucleotides, that is not included in the $6^{th}$ gene construct is operably linked to a promoter; and viii) an $11^{th}$ expression vector that includes the $9^{th}$ gene construct; and a $12^{th}$ expression vector, which optionally includes the $7^{th}$ gene construct.

The vaccine adjuvant may promotes a T lymphocyte-specific immune response without inducing a B lymphocyte-specific immune response.

In the vaccine adjuvant, the IL-12p35 protein may consist of an amino acid sequence which has at least 90%, and preferably at least 95% of a sequence homology with the human IL-12p35 that consists of an amino acid sequence of SEQ ID NO: 1, and it is also possible to use the IL-12p35 derived from non-humans (e.g., primates or simians) that have a high level of homology not to induce any immune response in the human body. The IL-12p40 protein may consist of an amino acid sequence which has at least 90%, and preferably at least 95% of a sequence homology with the human IL-12p40 that consists of an amino acid sequence of SEQ ID NO: 2, and it is also possible to use the IL-12p40 derived from non-humans (e.g., primates or simians) that have a high level of homology not to induce any immune response in the human body. It is also possible to use the IL-12p35 and the IL-12p40 as sequences described in KR Patent No. 0399728. The IL-21 protein may consist of an amino acid sequence which has at least 90%, and preferably at least 95% of a sequence homology with the human IL-21 that consists of an amino acid sequence of SEQ ID NO: 3, and it is also possible to use the IL-21 derived from non-humans (e.g., primates or simians) that have a high level of homology not to induce any immune response in the human body.

The vaccine adjuvant may further include at least one selected from the group consisting of:

an MIP-1α gene construct, in which a polynucleotide encoding the MIP-1α protein is operably linked to a promoter;

a complex gene construct, in which a polynucleotide encoding the MIP-1α protein is operably linked to at least one among the polynucleotides encoding each of the IL-12p35, IL-12p40, and IL-21 proteins, by a polynucleotide encoding an IRES or linker peptide; and an mRNA molecule encoding the MIP-1α protein.

In the vaccine adjuvant, the polynucleotide encoding the MIP-1α protein may be operably linked to polynucleotides encoding each of the IL-12p35, IL-12p40, and IL-21 proteins via a polynucleotide or IRES that encodes a peptide linker, or may be provided in the form of a separate gene construct. That is, the MIP-1α gene construct may be included in a separate expression vector, or the MIP-1α gene construct may be included in any one or more vector among the one to three vectors, each of which include: polynucleotides that respectively encode a p35 chain (IL-12p35) and a p40 chain (IL-12p40) that constitute the IL-12 protein; and a polynucleotide that encodes the IL-21 protein. That is, the MIP-1α gene construct may be included in at least one expression vector selected from the group consisting of a $1^{th}$ expression vector to a $12^{th}$ expression vector described in the exemplary embodiment with regard to the vaccine adjuvant.

In the vaccine adjuvant, the MIP-1α protein may consist of an amino acid sequence which has at least 90%, and preferably at least 95% of a sequence homology with the MIP-1α protein that consists of an amino acid sequence of SEQ ID NO: 10, and it is also possible to use the MIP-1α protein derived from non-humans (e.g., primates or simians) that have a high level of homology not to induce any immune response in the human body.

In another aspect of the present invention, there is provided a vaccine adjuvant including an IL-12 protein and an IL-21 protein as active ingredients.

In the vaccine adjuvant, the IL-12 protein may consist of a p35 chain (IL-12p35) and a p40 chain (IL-12p40).

The vaccine adjuvant may further include MIP-1α protein.

The IL-12 protein, IL-21 protein, and MIP-1α are as described above.

As used herein, the term "operably linked to" means that the nucleic acid sequence of interest (e.g., in vitro transcription/translation system or in a host cell) is linked to the control sequence such that the heterologous nucleic acid sequence can be expressed.

The term "control sequence" is a term that includes a promoter, an enhancer, and other control sequences (e.g., a polyadenylated signal). The control sequence includes: one which directs such that the heterologous nucleic acid is constitutively expressed in many host cells, one which directs such that the heterologous nucleic acid is expressed only in cells of a specific tissue (e.g., a tissue-specific control sequence), and one which directs such that expression is induced by a particular signal (e.g., an inducible control sequence). One of ordinary skill in the art will be able to understand that the design of the expression vector may depend on factors, such as the choice of a host cell to be transformed, the level of protein expression desired, etc. The expression vector of the present invention may be introduced into a host cell to express the fusion protein. Control sequences that allow expression in the eukaryotic and prokaryotic cells are well known to those skilled in the art. As described above, these control sequences include those which are normally in charge of the initiation of transcription and a poly-A signal which is in charge of selective termination of transcription of a transcript and stabilization thereof. Additional control sequences may include translation enhancing factors and/or native-combined or heterologous promoter regions, in addition to transcription control factors. For example, possible control sequences that enable expression in a mammalian host cell may include CMV-HSV thymidine kinase promoter, SV40, RSV-promoter (Rous sarcoma virus), human elongation factor 1α-promoter, glucocorticoid-inducible MMTV-promoter (Moloney mouse tumor virus), metallothionein-inducible or tetracycline-inducible promoter, or an amplifying agent such as a CMV amplifying agent or an SV40-amplifying agent. For expression in neurons, the use of neurofilament-promoter, PGDF-promoter, NSE-promoter, PrP-promoter, or thy-1-promoter is being considered. The promoters are well known in the art and are described in the literature (Charron, *J. Biol. Chem.* 270: 25739-25745). For expression in prokaryotic cells, many promoters including lac-promoter, tac-promoter, and trp promoter are disclosed. These control sequences may also include a transcription termination signal (e.g., SV40-poly-A region or TK-poly-A region) in the downstream of the polynucleotide in accordance with an exemplary embodiment of the present disclosure, in addition to those factors which can initiate transcription. In the present disclosure, suitable expression vectors are well known in the art, for example, Okayama-Berg cDNA expression vector pcDV1 (Parmacia), pRc/CMV, pcDNA1, pcDNA3 (In-vitrogene), pSPORT1 (GIBCO BRL), pGX27 (KR Patent No. 1442254), pX(Pagano (1992) Science 255, 1144-1147), yeast two-hybrid vector, for example, pEG202 and dpJG4-5 (Gyuris (1995) *Cell* 75, 791-803) or eukaryotic expression vector, for example, lambda gt11 or pGEX (Amersham-Pharmacia). The vector may further include a polynucleotide encoding a secretion signal peptide, in addition to the nucleic acid molecules of the present disclosure. The secretion signal peptides are well known to those skilled in the art. Additionally, according to the expression system used, a leader sequence which can direct the fusion protein to the cell compartment is combined with the coding sequence of the polynucleotide according to an exemplary embodiment of the present disclosure, and preferably a leader sequence which can directly secrete the translated protein or a protein thereof into the pericytoplasmic or extracellular medium.

In addition, vectors of the present invention can be prepared, for example, by standard recombinant DNA techniques. Examples of the standard recombinant DNA techniques include ligation of blunt ends and sticky ends, restriction enzyme treatment to provide appropriate ends, removal of phosphate groups by alkaline phosphatase treatment to prevent inappropriate bindings, enzymatic linkage by T4 DNA ligase, etc. The vector of the present invention may be prepared by recombination of the DNA encoding the signal peptide obtained by chemical synthesis or genetic recombination technology or the DNA encoding the IL-12 and IL-21 proteins of the present invention to the vector which include an appropriate control sequence. The vector containing the control sequence may be purchased or manufactured commercially, and in an exemplary embodiment of the present disclosure, pGX27, which is a vector for the preparation of DNA vaccines, was used.

The expression vector according to an exemplary embodiment of the present invention may be an expression vector that can express the fusion protein, and the expression vector may represent without limitation any form of a plasmid vector, a viral vector, a cosmid vector, a phagemid vector, an artificial human chromosome, etc.

As used herein, the term "fusion protein" refers to a recombinant protein in which two or more proteins or domains in charge of specific functions in the protein are linked so that each protein or domain can be in charge of the intrinsic function. Conventionally, a linker peptide with a flexible structure may be inserted between the two or more proteins or domains. The linker peptide may include $(G_4S)_n$(unit: SEQ ID NO: 50, n is an integer of 1 to 10), $(GS)_n$ (n is an integer of 1 to 10), $(GSSGGS)_n$ (unit: SEQ ID NO: 51, n is an integer of 1 to 10), KESGSVSSEQLAQFRSLD (SEQ ID NO: 52), EGKSSGSGSESKST (SEQ ID NO: 53), GSAGSAAGSGEF (SEQ ID NO: 54), $(EAAAK)_n$(unit: SEQ ID NO: 55, n is an integer of 1 to 10), CRRRRRRE-AEAC(SEQ ID NO: 56), $A(EAAAK)_4ALEA(EAAAK)_4A$ (SEQ ID NO: 57), GGGGGGGG (SEQ ID NO: 58), GGGGGG (SEQ ID NO: 59), AEAAAKEAAAAKA (SEQ ID NO: 60), PAPAP (SEQ ID NO: 61), $(Ala\text{-}Pro)_n$ (n is an integer of 1 to 10), VSQTSKLTRAETVFPDV (SEQ ID NO: 62), PLGLWA (SEQ ID NO: 63), TRHRQPRGWE (SEQ ID NO: 64), AGNRVRRSVG (SEQ ID NO: 65), RRRRRRRR (SEQ ID NO: 66), GFLG (SEQ ID NO: 67), GSSGGSGSSGGSGGGDEADGSRGSQKAGVDE (SEQ ID NO: 68), etc.

The expression vector may further include a polynucleotide that encodes one or two or more of peptides for enhancing immunity, and the peptides for enhancing immunity may be CD28, inducible costimulator (ICOS), cytotoxic T lymphocyte associated protein 4 (CTLA4), programmed cell death protein 1 (PD1), B and T lymphocyte associated protein (BTLA), death receptor 3 (DR3), 4-1BB, CD2, CD40, CD30, CD27, signaling lymphocyte activation molecule (SLAM), 2B4 (CD244), natural-killer group 2, member D (NKG2D)/DNAX-activating protein 12 (DAP12), T-Cell immunoglobulin and mucin domain containing protein 1 (TIM1), TIM2, TIM3, TIGIT, CD226, CD160, lymphocyte activation gene 3 (LAG3), B7-1, B7-H1, glucocorticoid-induced TNFR family related protein (GITR), fms-like tyrosine kinase 3 ligand (Flt3 ligand), flagellin, herpesvirus entry mediator (HVEM), or a cytoplasmic domain of OX40L[ligand for CD134(OX40) and CD252], or a linker of at least two thereof.

The expression vector may further include a polynucleotide encoding a secretory signal sequence, and the secretory signal sequence induces the secretion of recombinant proteins expressed in cells outside the cell, and may be tissue plasminogen activator (tPA) signal sequence, herpes simplex virus glycoproteins (HSV gDs) signal sequence, or a growth hormone signal sequence.

In another aspect of the present invention, there is provided a vaccine composition for prevention and treatment of virus infection includes, as active ingredients, the vaccine adjuvant and an antigen derived from infectious virus, an antigen gene construct in which the polynucleotide encoding the antigen is operably linked to a promoter, or an expression vector including the gene construct.

In the vaccine composition, the antigen derived from infectious virus may be an antigen derived from Epstein-Barr virus (EBV), hepatitis A virus (HAV), hepatitis B virus (HBV), hepatitis C virus (HCV), hepatitis D virus (HDV), hepatitis E virus (HEV), Hantaan virus, cytomegalovirus (CMV), human immunodeficiency virus (HIV), influenza virus, human papillomavirus (HPV), poliovirus, ebola virus, rotavirus, dengue virus, West Nile virus, yellow fever virus, adenovirus, Japanese encephalitis virus, BK virus, smallpox virus, Zika virus, severe fever with thrombocytopenia syndrome (SFTS) virus, or herpes simplex virus (HSV).

According to still another aspect of the present disclosure, there is provided a vaccine composition for cancer treatment includes, as active ingredients, the vaccine adjuvant and a cancer antigen, a polynucleotide encoding the cancer antigen, an antigen gene construct in which the polynucleotide is operably linked to a promoter, or an expression vector including the gene construct.

In the vaccine composition for cancer treatment, the cancer antigen may be a human papillomavirus (HPV)-derived antigen, a carcinoembryonic antigen, a prostate-specific membrane antigen (PSMA), Her2/neu, MUC-1, BCR/ABL, α-fetoprotein (AFP), an Epstein-Barr virus (EBV)-derived antigen, a human hepatitis B virus (HBV)-derived antigen, a human hepatitis C virus (HCV)-derived antigen, cancer antigen-125 (CA-125), cancer antigen-72-4 (CA-72-4), cancer antigen-15-3 (CA-15-3), or cancer antigen-19-9 (CA-19-9).

The vaccine composition may further include a pharmaceutically acceptable adjuvant, an excipient, or a diluent, in addition to the carrier.

As used herein, the term "pharmaceutically acceptable" refers to a composition which is physiologically acceptable and does not normally cause an allergic reaction (e.g., a gastrointestinal disorder, dizziness, etc.) or a similar reaction thereof when administered to humans. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methylhydroxybenzoate, propylhydroxybenzoate, talc, magnesium stearate, and mineral oil. In addition, fillers, anti-coagulants, lubricants, humectants, fragrances, emulsifiers, preservatives, etc. may be further included.

The vaccine composition may further include a conventionally used vaccine adjuvant, in addition to the vaccine adjuvant above. As the conventionally used vaccine adjuvant, aluminum hydroxide, aluminum phosphate, alum (potassium aluminum sulfate), MF59, virosome, AS04 [a mixture of aluminum hydroxide and monophosphoryl lipid A (MPL)], AS03 (a mixture of DL-α-tocopherol, squalene, and polysorbate 80 (an emulsifier)), CpG, Flagellin, Poly I:C, AS01, AS02, ISCOMs, ISCOMMATRIX, etc. may be used.

As used herein, the term "adjuvant" or "vaccine adjuvant" refers to a pharmaceutical or immunological preparation being administered for the purpose of improving the immune response of a vaccine.

Additionally, the vaccine adjuvant or the vaccine composition containing the vaccine adjuvant according to an exemplary embodiment of the present invention may be formulated using methods known in the art so as to enable rapid release, or sustained or delayed release of the active ingredient when administered to a mammal. These preparations may include powders, granules, tablets, emulsions, syrups, aerosols, soft or hard gelatin capsules, sterile injectable solutions, and sterile powders.

The vaccine adjuvant or the vaccine composition containing the vaccine adjuvant according to an exemplary embodiment of the present invention may be administered in various routes including, for example, oral, parenteral (e.g., suppository, transdermal, intravenous, intraperitoneal, intramuscular, intralesional, nasal, spinal canals, or may be administered using an implantable device for sustained, continuous, or repeated release. The number of administrations may be administered once or several times a day within a desired range, and the administration period is not particularly limited.

The vaccine adjuvant or the vaccine composition containing the vaccine adjuvant according to an exemplary embodiment of the present invention may be administered by conventional systemic or topical administration (e.g., intramuscular injection or intravenous injection), if provided as a DNA vaccine composition, the vaccine composition may be most preferably injected using an electroporator. As the electroporator, electroporators for injecting a commercially available DNA drug into the body (e.g., Glinporator™ of IGEA, Italy, CUY21EDIT of JCBIO, Korea, SP-4a of Supertech, Switzerland, OrbiJector of SLVAXiGEN, Korea, etc.) may be used.

The administration route of the vaccine adjuvant or the vaccine composition containing the vaccine adjuvant according to an exemplary embodiment of the present invention may be administered via any conventional route as long as the vaccine composition can reach the target tissue. The administration route may include, but is not limited to, parenteral administration (e.g., intraperitoneal, intravenous, intramuscular, subcutaneous, and intrathecal administration).

The administration route of the vaccine adjuvant or the vaccine composition containing the vaccine adjuvant according to an exemplary embodiment of the present invention may be formulated in a suitable form together with a commonly available pharmaceutically acceptable carrier. The pharmaceutically acceptable may include, for example, water, suitable oils, saline, parenteral vehicles (e.g., aqueous glucose, glycols, etc.) and may further contain stabilizers and preservatives. Suitable stabilizers may include antioxidants (e.g., sodium hydrogen sulfite, sodium sulfite, or ascorbic acid). Suitable preservatives may include benzalkonium chloride, methyl- or propyl-paraben and chlorobutanol. Additionally, the composition according to the present invention may appropriately include a suspending agent, a dissolution adjuvant, a stabilizer, an isotonic agent, a preservative, an adsorption inhibitor, a surfactant, a diluent, an excipient, a pH adjusting agent, an analgesic agent, a buffering agent, an antioxidant, etc., depending on the administration method and preparation, if necessary. Suitable examples of suitable pharmaceutically acceptable carriers and preparations suitable for the present disclosure, including those exemplified above, are described in detail in the literature [Remington's Pharmaceutical Sciences, New Edition].

The administration dose of the vaccine composition for a patient may vary depending on many factors including the patient's height, body surface area, age, the particular compound being administered, sex, time and route of administration, general health conditions, and other drugs being administered concurrently. The pharmaceutically active DNA may be administered in an amount of 100 ng/body weight (kg) to 10 mg/body weight (kg), more preferably from 1 μg/kg to 500 μg/kg (body weight), and most preferably from 5 μg/kg to 50 μg/kg (body weight), and the administration dose may be adjusted considering the factors.

In addition, the vaccine composition of the present invention may be administered in a pharmaceutically effective amount.

As used herein, the term "pharmaceutically effective amount" refers to an amount sufficient for the treatment of diseases at a reasonable benefit/risk ratio applicable to medical treatment, and the level of the effective dose may be determined based on the factors including the kind of subject, severity of illness, age, sex, drug activity, drug sensitivity, administration time, administration route and dissolution rate, length of treatment, factors including drug(s) to be used simultaneously in combination, and other factors well known in the medical field. The vaccine composition of the present invention may be administered at a dose of 0.1 mg/kg to 1 g/kg, and more preferably from 1 mg/kg to 500 mg/kg. Meanwhile, the administration dose may be appropriately adjusted according to age, sex, and health conditions of the patient.

In addition, according to still another aspect of the present disclosure, there is provided a method for stimulating a T lymphocyte-specific immune response by a vaccine composition including administering, to an individual, the vaccine adjuvant along with a vaccine composition, or before or after the administration of the vaccine composition.

In the method, the vaccine adjuvant may be administered by in vivo electroporation.

The method is characterized in that the method selectively induces only a T lymphocyte-specific immune response without inducing a B cell-specific immune response of the individual.

Hereinafter, the present invention will be described in more detail through Examples and Experimental Examples. However, the present invention is not limited to the Examples and Experimental Examples described below, but may be implemented in various other forms. The following Examples and Experimental Examples are provided to enable the disclosure of the present invention to be complete and to fully convey the scope of the invention to those skilled in the art to which the present invention belongs.

Example 1

Preparation of Expression Vectors for Human IL-12 and IL-21

1-1: Single Vector System

The present inventors have designed a single vector system such that IL-12 and IL-21 are expressed via a single vector.

For this purpose, specifically, the present inventors have prepared a gene construct by linking the polynucleotides (SEQ ID NOS: 4 and 5) which encode each of two subunits of human IL-12 protein (i.e., the hIL-12p35 polypeptide consisting of an amino acid sequence of SEQ ID NO: 1 and the hIL-12p40 polypeptide consisting of an amino acid sequence of SEQ ID NO: 2) to an EMCV-derived internal ribosome entry site (IRES) having a nucleic acid sequence of SEQ ID NO: 6; and sequentially linking the RSV promoter (pRSV) of SEQ ID NO: 7 and a polynucleotide (SEQ ID NO: 8), which encodes human IL-21 protein (hIL-21) consisting of an amino acid sequence of SEQ ID NO: 3, to the 3'-end of a polynucleotide encoding the hIL-12p40 polypeptide; and then inserting the gene construct into a multiple cloning site of the pGX-27 vector (KR Patent No. 1442254), thereby preparing a vector according to an exemplary embodiment of the present disclosure. The thus prepared vector was named as "hBD-121" (FIG. 1*a*).

1-2: Dual Vector System

The present inventors designed a dual vector system such that IL-12 and IL-21 are inserted into separate vectors to be expressed.

The dual vector system is prepared as follows:

A polynucleotide (SEQ ID NO: 4) encoding the hIL-12p35 polypeptide and a polynucleotide (SEQ ID NO: 5) encoding the hIL-12p40 polypeptide are linked to an EMCV-IRES having a nucleic acid sequence of SEQ ID NO: 6; and the resultant is inserted into a multiple cloning site of the pGX-27 vector; and likewise, a polynucleotide (SEQ ID NO: 8) encoding the human IL-21 protein (hIL-21) is also inserted into a multiple cloning site of the pGX-27 vector; and thereby a dual vector system is prepared.

1-3: Triple Vector System

Since the IL-12 is a dimer protein consisting of a hIL-12p35 polypeptide and a hIL-12p40 polypeptide, the hIL-12p35 polypeptide and the hIL-12p40 polypeptide may be expressed from an independent vector. As such, according to an exemplary embodiment of the present disclosure, the hIL-12p35 polypeptide, hIL-12p40 polypeptide, and IL-21 may be expressed via each of three independently constituted vectors, and for convenience purposes, this was named as "triple vector system".

The triple vector system may be prepared as follows:

The polynucleotides (SEQ ID NOS: 4, 5, and 8) encoding each of the hIL-12p35 polypeptide, hIL-12p40 polypeptide, and hIL-21 are inserted into a multiple cloning site of the pGX-27 vector, and thereby preparing a triple vector system.

Example 2

Preparation of Expression Vectors for Human IL-12, IL-21, and MIP-1α

A gene construct was prepared by linking the polynucleotides (SEQ ID NOS: 4 and 5), which encode each of the hIL-12p35 polypeptide consisting of an amino acid sequence of SEQ ID NO: 1 and the hIL-12p40 polypeptide consisting of an amino acid sequence of SEQ ID NO: 2, to an EMCV-derived internal ribosome entry site (IRES) having a nucleic acid sequence of SEQ ID NO: 6; and sequentially linking human EF-1α promoter (pEF-1α), which consists of a nucleic acid sequence of SEQ ID NO: 9, and a polynucleotide (SEQ ID NO: 11), which encodes human MIP-1α protein (hMIP-1α) consisting of an amino acid sequence of SEQ ID NO: 10, to a polynucleotide, to which the RSV promoter (pRSV) of SEQ ID NO: 7 and a polynucleotide (SEQ ID NO: 8), which encodes human IL-21 protein (hIL-21) consisting of an amino acid sequence of SEQ ID NO: 3, are sequentially linked; and inserting the gene construct into a multiple cloning site of the pGX-27 vector; and the thus prepared vector was named as "hBD-121A" (FIG. 1*b*).

Example 3

Preparation of Expression Vectors for Mouse IL-12 and IL-21

A gene construct was prepared by linking the polynucleotides (SEQ ID NOS: 14 and 15) which encode each of two subunits of mouse IL-12 protein (i.e., the mIL-12p35 polypeptide consisting of an amino acid sequence of SEQ ID NO: 12 and the mIL-12p40 polypeptide consisting of an amino acid sequence of SEQ ID NO: 13) to an EMCV-derived internal ribosome entry site (IRES) having a nucleic acid sequence of SEQ ID NO: 6; and sequentially linking the RSV promoter (pRSV) of SEQ ID NO: 7 and a polynucleotide (SEQ ID NO: 17), which encodes mouse IL-21 protein (mIL-21) consisting of an amino acid sequence of SEQ ID NO: 16, to the 3'-end of a polynucleotide encoding the mIL-12p40 polypeptide; and inserting the gene construct into a multiple cloning site of the pGX-27 vector, thereby preparing a vector according to an exemplary embodiment of the present disclosure. The thus prepared vector was named as "mBD-121" (FIG. 1*a*).

Example 4

Preparation of Expression Vectors for Mouse IL-12, IL-21 and MIP-1α

A gene construct was prepared by linking the polynucleotides (SEQ ID NOS: 14 and 15), which encode each of the mIL-12p35 polypeptide consisting of an amino acid sequence of SEQ ID NO: 12 and the mIL-12p40 polypeptide consisting of an amino acid sequence of SEQ ID NO: 13, to an EMCV-derived internal ribosome entry site (IRES) having a nucleic acid sequence of SEQ ID NO: 6; and sequentially linking human EF-1α promoter (pEF-1α), which consists of a nucleic acid sequence of SEQ ID NO: 9, and a polynucleotide (SEQ ID NO: 19), which encodes mouse MIP-1α protein (mMIP-1α) consisting of an amino acid sequence of SEQ ID NO: 18, to the 3'-end of a polynucleotide encoding the mIL-12p40 polypeptide (SEQ ID NO: 15), to which the RSV promoter (pRSV) of SEQ ID NO: 7 and a polynucleotide (SEQ ID NO: 17), which encodes mouse IL-21 protein (mIL-21) consisting of an amino acid sequence of SEQ ID NO: 16, are sequentially linked; and inserting the gene construct into a multiple cloning site of the pGX-27 vector; and the thus prepared vector was named as "mBD-121A" (FIG. 1*b*).

Example 5

Preparation of HPV DNA Vaccine Construct

To prepare a 14-valent HPV DNA vaccine, the present inventors have obtained polynucleotides encoding the N-terminal fragment and the C-terminal fragment of E6 and E7 antigens of each type obtained by PCR, in order to express the E6 and E7 antigens in the form of a shuffled fusion protein, in which the early expression proteins E6 and E7 of HPV types 6, 11, 16, 18, 31, 33, 35, 39, 45, 51, 52, 56, 58, and 59 belong to a high-risk group, and then have linked the polynucleotides by linking in the order disclosed in FIG. 2 and Table 1, thereby preparing three gene constructs. Each of the three gene constructs was inserted into a pGX-27 vector, thereby preparing a HPV DNA construct. Each of the three gene constructs was named as BD-14A, BD-14B, and BD-14C, respectively, and the composition containing these three vectors was named as BD-14. The reason why the polyvalent HPV DNA vaccine construct was prepared as a triple vector system was because the pGX-27 vector is inefficient in capacity when the size of the gene construct to be inserted is too large.

As shown in FIG. 2 and Table 1, the E6 and E7 antigens of each HPV type were constructed in such a structure where these antigens are divided into the N-terminal fragment and the C-terminal fragment in which a partial sequence is overlapping, respectively, and then a fusion polypeptide, where the C-terminal fragment of E7 is linked to the end of the N-terminal fragment of E6, and a fusion polypeptide, where the C-terminal fragment of E6 is linked to the end of the N-terminal fragment of E7, are linked again by a $(GS)_5$ linker peptide, so that 4 to 5 antigen units of each type are linked to the $(GS)_5$ linker to be included in a single vector. The kinds of each subtype to be inserted into one expression vector are exemplarily shown in Table 1, but they are for illustrative purposes only and may be prepared in any other order.

TABLE 1

Constitution of 14-valent HPV DNA vaccine construct of the present disclosure

| Constituting Element | | Specific Structure | SEQ ID NO Protein | SEQ ID NO Nucleic Acid | Origin |
|---|---|---|---|---|---|
| Common | linker | $(GS)_5$ | 20 | 21 | N/A |
| Element | tPA | $tPA_{1-22}$ | 22 | 23 | Uniprot: P00750 |
| | Flt3L | $Flt3L_{27-182,\ \Delta 1-26}$ | 24 | 25 | Uniprot: P49771 |
| BD-14A | 16E6E7 | $16E6N_{1-85}$-$16E7C_{41-105}$-$(GS)_5$-$16E7N_{1-60}$-$16E6C_{66-158}$ | 26 | 27 | GenBank: K02718.1 |
| | 18E6E7 | $18E6N_{1-85}$-$18E7C_{41-98}$-$(GS)_5$-$18E7N_{1-60}$-$18E6C_{66-158}$ | | | GenBank: X05015.1 |
| | 35E6E7 | $35E6N_{1-78}$-$35E7C_{42-99}$-$(GS)_5$-$35E7N_{1-61}$-$35E6C_{59-149}$ | | | GenBank: X74477.1 |
| | 45E6E7 | $45E6N_{1-85}$-$45E7C_{41-10}6$-$(GS)_5$-$45E7N_{1-60}$-$45E6C_{66-158}$ | | | GenBank: X74479.1 |
| | 58E6E7 | $58E6N_{1-85}$-$58E7C_{41-98}$-$(GS)_5$-$58E7N_{1-60}$-$58E6C_{66-149}$ | | | GenBank: D90400.1 |
| BD-14B | 31E6E7 | $31E6N_{1-85}$-$31E7C_{42-98}$-$(GS)_5$-$31E7N_{1-61}$-$31E6C_{66-149}$ | 28 | 29 | GenBank: J04353.1 |
| | 33E6E7 | $33E6N_{1-85}$-$33E7C_{42-96}$-$(GS)_5$-$33E7N_{1-61}$-$33E6C_{66-149}$ | | | GenBank: M12732.1 |
| | 06E6E7 | $6E6N_{1-85}$-$6E7C_{42-98}$-$(GS)_5$-$6E7N_{1-61}$-$6E6C_{66-150}$ | | | GenBank: X00203.1 |
| | 11E6E7 | $11E6N_{1-85}$-$11E7C_{42-98}$-$(GS)_5$-$11E7N_{1-61}$-$11E6C_{66-150}$ | | | GenBank: M14119.1 |
| | 52E6E7 | $52E6N_{1-85}$-$52E7C_{41-99}$-$(GS)_5$-$52E7N_{1-60}$-$52E6C_{66-148}$ | | | GenBank: X74481.1 |
| BD-14C | 39E6E7 | $39E6N_{1-85}$-$39E7C_{44-109}$-$(GS)_5$-$39E7N_{1-63}$-$51E6C_{66-158}$ | 30 | 31 | GenBank: M62849.1 |
| | 51E6E7 | $51E6N_{1-83}$-$51E7C_{45-101}$-$(GS)_5$-$51E7N_{1-64}$-$51E6C_{64-151}$ | | | Uniprot: P26554(E6), P26558(E7) |
| | 56E6E7 | $56E6N_{1-86}$-$56E7C_{48-105}$-$(GS)_5$-$56E7N_{1-67}$-$56E6C_{67-155}$ | | | Uniprot: P24836(E6), P36833(E7) |
| | 59E6E7 | $59E6N_{1-85}$-$59E7C_{50-107}$-$(GS)_5$-$59E7N_{1-69}$-$59E6C_{66-160}$ | | | GenBank: CAA54849.1(E6), CAA54850.1(E7) |

Example 6

Preparation of CMV DNA Vaccine Construct

To prepare a CMV DNA vaccine construct, the present inventors prepared a polynucleotide encoding the proteins in which the CMV glycoprotein B (gB) and the pp65 protein are included, and then inserted the polynucleotide into a multiple cloning site of the pGX-27 vector, and thereby preparing a CMV DNA vaccine construct (FIG. 3).

Example 7

Preparation of HBV DNA Vaccine Construct

To prepare a HBV DNA vaccine construct, the present inventors prepared a HBV DNA vaccine construct so as to express preS1, preS2, S antigen, a surface antigen, and a nuclear antigen, and then inserted the HBV DNA vaccine construct into the pGX-27 vector.

Example 8

Preparation of HSV-2 DNA Vaccine Construct

To prepare a HSV-2 DNA vaccine construct, the present inventors divided the UL39 antigen of HSV-2 into 5 fragments (i.e, N1: $UL39_{21-154(\Delta 78-104)}$, C2: $UL39_{1117-1142}$, N2: $UL39_{165-227}$, N4-C1: $UL39_{398-1116}$, and N3: $UL39_{208-398}$), and then inserted a shuffled UL-39 antigen of HSV-2 (arrayed by shuffling the 5 fragments) and a gene construct encoding the shuffled UL-39 into a multiple cloning site of the pGX-27 vector, and thereby preparing a HSV-2 DNA vaccine construct.

Specifically, the shuffled-UL39 plasmid DNA was prepared by inserting, into the pGX-27 plasmid vector, a gene construct which includes a polynucleotide (SEQ ID NO: 38) that encodes the form sequentially connected in the order of UL39-N1, UL39-C2, UL39-N2, UL39-N4-C1, and UL39-N3, based on the form divided into UL39-N1 (SEQ ID NO: 32), UL39-C2 (SEQ ID NO: 33), UL39-N2 (SEQ ID NO: 34), UL39-N4-C1 (SEQ ID NO: 35), and UL39-N3 (SEQ ID NO: 36) (FIG. 4*a*), and the shuffled-UL39 plasmid DNA was named as “BD-02B”.

Furthermore, the present inventors prepared a tPA-Flt3L-gD-ICP0-ICP4 plasmid DNA by inserting a gene construct into the pGX-27 vector, in which the gene construct includes a polynucleotide (SEQ ID NO: 43) encoding the tPA-Flt3L-gD-ICP0-ICP4 fusion protein (SEQ ID NO: 42), in which a HSV-2 antigen other than the shuffled UL39 antigen, that is, a glycoprotein D ($gD_{26-349}$) in which a signal sequence ($gD_{1-25}$) and a transmembrane domain ($gD_{350-363}$) are removed (SEQ ID NO: 39), an infected cell polypeptide 0 ($ICP0_{\Delta 510-516}$, SEQ ID NO: 40) in which a nuclear localization sequence (NLS, $ICP0_{510-516}$) is removed, and an infected cell polypeptide 4 ($ICP4_{\Delta 767-1318}$, SEQ ID NO: 41) in which the RS1.3 part ($ICP_{767-1318}$) is removed are connected (FIG. 4*b*). Both the above two plasmid DNAs are plasmid DNAs which are designed to be expressed in the form of a fusion protein, in which a tPA secretory signal sequence (SEQ ID NO: 22) which is codon optimized for efficient expression, and an FMS-like tyrosine kinase 3 ligand (Flt3L, SEQ ID NO: 24) (i.e., an immunoactive protein) are added to the N-terminus. The thus prepared plasmid DNA for a DNA vaccine was named as “BD-02C” and the DNA vaccine composition consisting of the “BD-02B” and the “BD-02C” were named as “BD-02”.

Example 9

Preparation of SFTS DNA Vaccine Construct

To express glycoproteins N and C (GnGc, SEQ ID NO: 44), nucleocapsid (NP, SEQ ID NO: 45), and nonstructural (NS) protein (SEQ ID NO: 46) antigens except the antigen RNA dependent RNA polymerase (RdRP) of SFTS, the present inventors amplified the polynucleotides encoding each of the proteins (SEQ ID NOS: 47 to 49) by PCR using the SFTS virus genome as a template. Each of the amplified polynucleotides was operably linked to CMV promoter (pCMV), RSV promoter (pRSV), and EF-1α promoter (pEF-1α), and thereby preparing a recombinant plasmid DNA (SFTS plasmid DNA), which is an SFTS DNA vaccine (FIG. 5).

Experimental Example 1

Confirmation of Potentials of IL-12 and IL-21 as Vaccine Adjuvant

The present inventors performed a preliminary experiment to confirm the potentials of IL-12 and IL-21 as the vaccine adjuvant in the form of a protein and DNA. For this purpose, specifically, the immune responses were examined by administering, to an individual, a HPV 2-valent DNA vaccine alone and in combination with IL-12 and/or IL-21 to HPV types 16 and 18.

Specifically, 2 μg each of type 16/18 HPV 2-valent DNA vaccine construct described in KR Patent Laid-open Publication No. 10-2017-0045254 was administered to the femoral muscles of C57BL/6 mice twice at two-week intervals using OrbiJector® (SLVAXiGEN, Korea) by in vivo electroporation, in combination with 2 μg each of a mIL-12 construct and/or a mIL-21 construct. Then, two weeks after the $2^{nd}$ administration day, spleens were extracted and the number of spleen immunocytes reactive to each type of HPV 16 and HPV18 was counted (FIG. 6).

As a result, as shown in FIG. 6, it was confirmed that the cells exhibiting an immune response in mice simultaneously treated with IL-12 and IL-21 were significantly increased, compared to the treatment with IL-12 or IL-21 alone, and in particular, it was confirmed that the effect was remarkable in type 18 HPV.

These results suggest that IL-12 and IL-21 are cytokines that can synergistically increase the immune response of the vaccine.

Experimental Example 2

Analysis of BD-121 Expression 2-1: ELISA Assay

The present inventors transformed each of the hBD-121 construct and the mBD-121 construct prepared in Examples 2 and 4 according to an exemplary embodiment of the present disclosure, respectively, into cells and examined whether IL-12 and IL-21 were normally expressed in the transformed cells. Specifically, the COS-7 cell line was inoculated on each 100 mm culture dish and cultured for 16 hours, transformed with each of an empty vector (mock plasmid DNA), the hBD-121 plasmid DNA prepared in Example 2-1, and the mBD-121 plasmid DNA prepared in Example 4, using Lipofectamine 2000. Each transformant was cultured in an incubator (37° C., $CO_2$) for 3 days, and the culture supernatant of the COS-7 cells under each condition was recovered and used as a sample. The IL-12 and IL-21 proteins present in each sample were quantified by ELISA assay using the antibodies (IL-12: R&D Systems, Cat #D1200, IL-21: BioLegend, Cat #433808) which specifically recognize IL-12 and IL-21, respectively (FIGS. 7*a* and 7*b*).

Figure 7A:
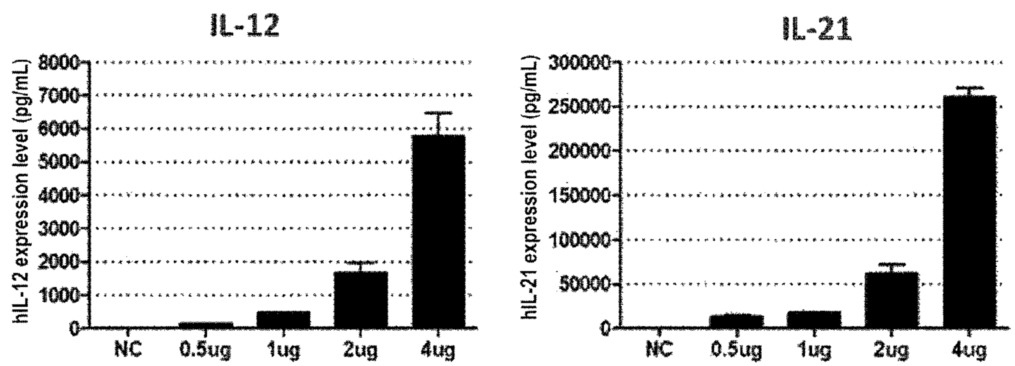
FIG. 7*a* is graphs showing the results of ELISA assay of concentrations of IL-12 and IL-21 in the culture supernatant of COS-7 cells transfected with a hBD-121 construct, which is a vaccine adjuvant in accordance with an exemplary embodiment.
Figure 7B:
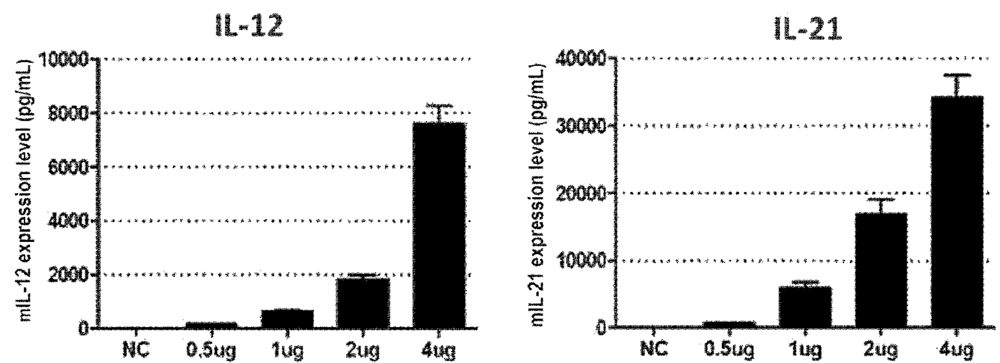
FIG. 7*b* is graphs showing the results of ELISA assay of concentrations of IL-12 and IL-21 in the culture supernatant of COS-7 cells transfected with an mBD-121 construct, which is a vaccine adjuvant in accordance with an exemplary embodiment.

As a result, as shown in FIG. 7*a*, when hIL-12 was introduced in an amount of 4 μg of DNA, the expression level of the proteins in the sample where the hBD-121 plasmid DNA was introduced was greater than 4,000 pg/mL thus confirming that these proteins were normally expressed, whereas when hIL-21 was introduced in an amount of 4 μg of DNA, the expression level of the proteins in the sample was as high as being close to 200 ng/mL thus confirming these proteins were expressed at high level. Furthermore, as shown in FIG. 7*b*, the mouse construct showed a result similar to that of the human construct. Meanwhile, in the control group where the empty vector was introduced, both proteins were not expressed at all thus confirming that the vaccine adjuvant expression system of the present invention acted normally.

1-2: Western Blot Analysis

Figure 7C:
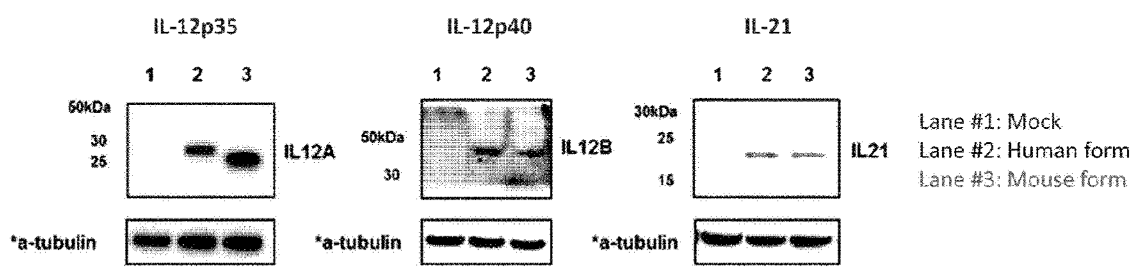
FIG. 7*c* shows the results of western blot analysis of expression levels of IL-12 and IL-21 in the culture supernatant of COS-7 cells transfected with a hBD-121 construct and an mBD-121 construct, respectively, which are vaccine adjuvants in accordance with an exemplary embodiment.

The present inventors performed SDS-PAGE electrophoresis using the cell lysate of the cells obtained in Experimental Example 1-1, transferred onto a nylon membrane, and performed western blot analysis using an anti-IL-12A antibody (Abcam, Cat #ab131039), an anti-IL-12B antibody (Abcam, Cat #ab133752), and an anti-IL-21 antibody (Abcam, Cat #ab5978) (FIG. 7*c*).

As a result, as shown in FIG. 7*c*, it was confirmed that both IL-12 and IL-21 were normally expressed by the transfection of BD-121 plasmid DNA according to an exemplary embodiment of the present disclosure.

Experimental Example 3

Analysis of Effect of BD-121 on Improving Immune Response Against Various Viruses Subsequently, from the results of Experimental Example 2, the present inventors examined whether a BD-121 construct according to an exemplary embodiment of the present invention can actually improve immune responses against various viruses.

3-1: T Cell-Specific Immune Response and Antibody Response Against CMV

Figure 8A:
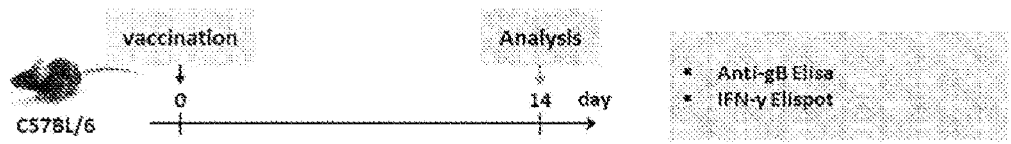
FIG. 8*a* shows the administration schedule for a CMV DNA vaccine prepared in accordance with an exemplary embodiment and BD-121, which is a vaccine adjuvant prepared in accordance with an exemplary embodiment.
Figure 8B:
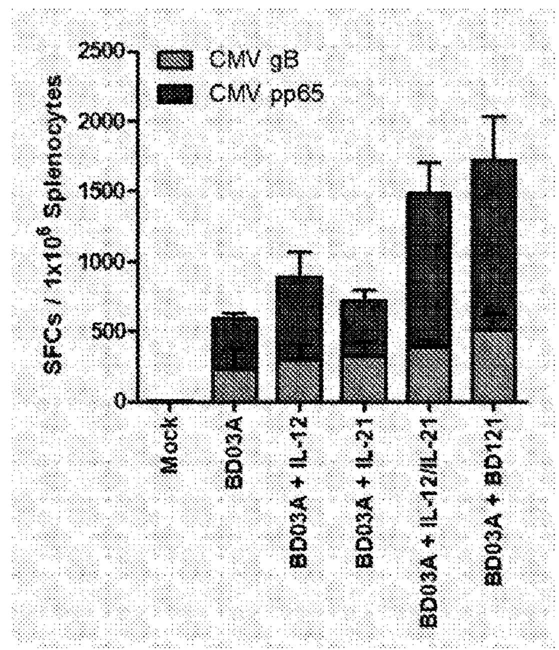
FIG. 8*b* is a graph showing the results of counting the number of spleen cells which responds in a CMV antigen-specific manner when a CMV DNA vaccine prepared in accordance with an exemplary embodiment is administered alone or in combination with IL-12, IL-21, or BD-121, which is a vaccine adjuvant prepared in accordance with an exemplary embodiment.
Figure 8C:
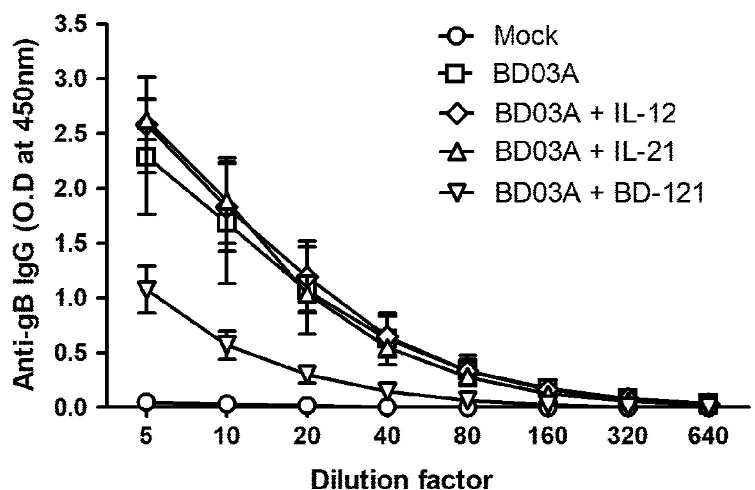
FIG. 8*c* is a graph showing the results of analysis of antigen-specific antibody responses when a CMV DNA vaccine prepared in accordance with an exemplary embodiment is administered alone or in combination with IL-12, IL-21, or BD-121, which is a vaccine adjuvant prepared in accordance with an exemplary embodiment.

First, the present inventors inoculated once the CMV DNA vaccine construct (0.5 μg), which was prepared in Example 6, alone or in combination with BD-121 (0.5 μg), to the femoral muscles of C57BL/6 mice using OrbiJector® (SLVAXiGEN, Korea) by in vivo electroporation. In particular, as comparative groups, expression vectors which express IL-12 and IL-21 (i.e., constituting elements of BD121), respectively, were administered alone or in combination (IL-12+IL-21), in an amount of 0.5 μg each in combination with the CMV DNA vaccine construct (0.5 μg) (Table 2). Two weeks after the inoculation of the vaccine, the experimental animals were sacrificed and spleens were extracted and the T cell-specific immune response against CMV was analyzed by ex vivo ELISPOT analysis using CMVpp65 (i.e., an antigen of CMV included in the CMV DNA vaccine) and a CMVgB peptide pool (FIG. 8*a*). The CMVgB-specific antibody response was analyzed via the CMV-specific antibody response ELISA test method using obtained blood plasma (FIGS. 8*a* to 8*c*).

TABLE 2

Compositions for administration of CMV vaccine of the present disclosure

| Group | No. of Heads for Experiment | Composition | Dose | Administration Route |
|---|---|---|---|---|
| 1 | 3 | Mock | 0.5 μg/plasmid | i. m. + Electroporation |
| 2 | 4 | CMV DNA vaccine | | |
| 3 | 4 | CMV DNA vaccine + IL-12 | | |
| 4 | 4 | CMV DNA vaccine + IL-21 | | |
| 5 | 4 | CMV DNA vaccine + IL-12 + IL-21 | | |
| 6 | 4 | CMV DNA vaccine + BD121 | | |

As a result, as shown in FIG. 8*b*, the BD-121 vaccine adjuvant according to an exemplary embodiment of the present invention resulted in a significantly higher T cell-specific immune response compared to when the CMV DNA vaccine was treated alone. Specifically, it was confirmed that when the CMV DNA vaccine was administered alone, the CMVpp65- and CMVgB-specific immune responses were 300 spot forming cells (SFCs) and 700 SFCs, respectively, whereas when the CMV DNA vaccine was administered in combination with BD-121, the CMVpp65- and CMVgB-specific immune responses were 2,000 SFCs and 2,100 SFCs, respectively, thus showing about 3-fold to 7-fold increase of antigen-specific T-cell responses. Meanwhile, as shown in FIG. 8*c*, as a result of the analysis of the level of the CMV-specific antibody production, the BD-121 of the present invention induced a rather lower antibody response compared to when the CMV DNA vaccine was treated alone. These results suggest that the BD-121 according to an exemplary embodiment of the present invention induces the enhancement of immunity by selectively strengthening the T cell-specific immune response (i.e., cell-mediated immune response), instead of a method of non-selectively increasing an immune response.

3-2: T Cell-Specific Immune Response and Antibody Response Against HBV

The present inventors inoculated the HBV DNA vaccine construct (2 μg), which was prepared in Example 7, alone or in combination with BD-121 (2 μg), to the femoral muscles of C57BL/6 mice twice at two-week intervals using OrbiJector® (SLVAXiGEN, Korea) by in vivo electroporation (priming and boosting, respectively). On the $2^{nd}$ inoculation day, i.e., two weeks from the boosting, the experimental animals were sacrificed and spleens were extracted and the T cell-specific immune response against HBV was analyzed by ex vivo ELISPOT analysis using the HBV antigens (HBsAg, HBcAg, and PreS1/S2) peptide pool included in the HBV DNA vaccine construct (FIG. 8*a*). In addition, with regard to the HBsAg-specific antibody response, the HBV-specific antibody response was analyzed by ELISA test method using the obtained blood plasma (FIGS. 9*a* and 9*b*).

Figure 9A:
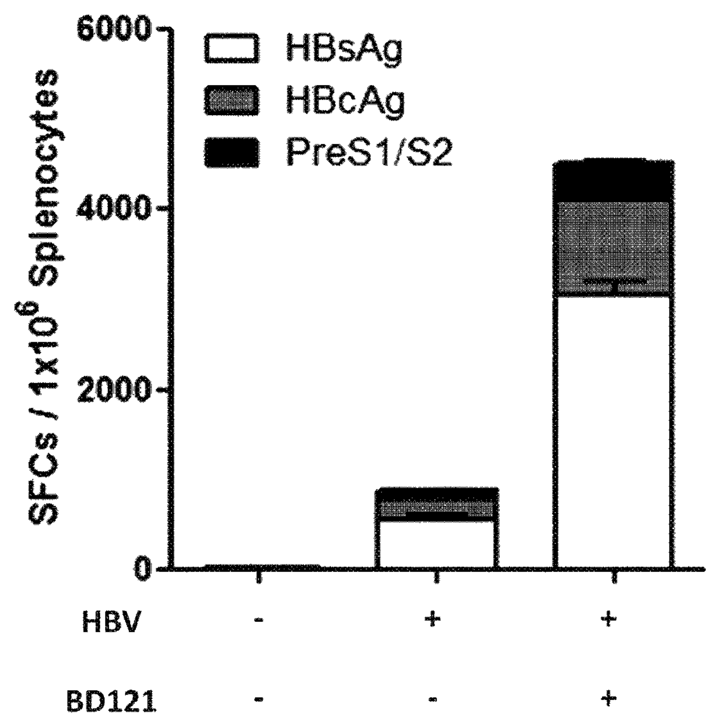
FIG. 9*a* is a graph showing the results of counting the number of spleen cells which responds in a HBV antigen (HBsAg, HBcAg, and PreS1/S2)-specific manner when a HBV DNA vaccine prepared in accordance with an exemplary embodiment is administered alone or in combination with BD-121, which is a vaccine adjuvant prepared in accordance with an exemplary embodiment.
Figure 9B:
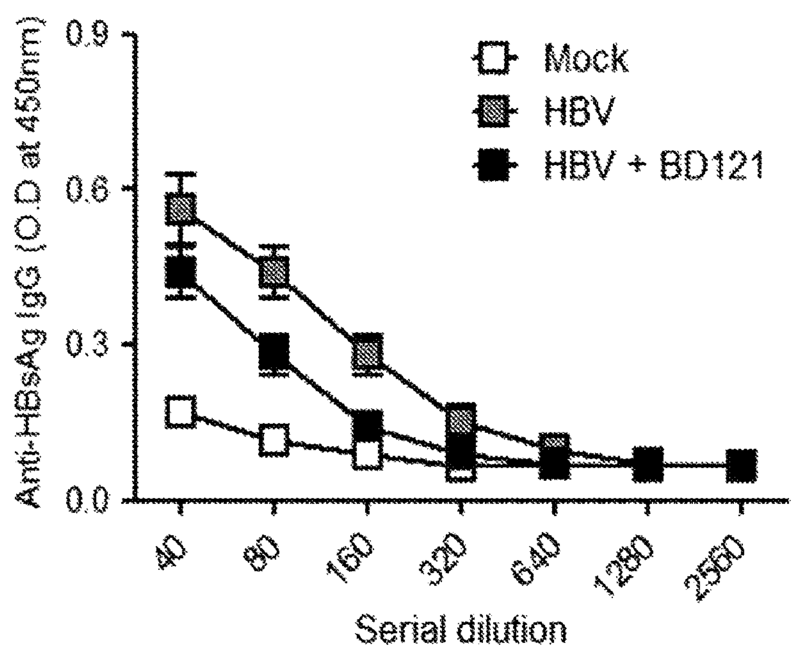
FIG. 9*b* is a graph showing the results of analysis of HBsAg-specific antibody responses when a HBV DNA vaccine prepared in accordance with an exemplary embodiment is administered alone or in combination with BD-121, which is a vaccine adjuvant prepared in accordance with an exemplary embodiment.

As a result, as shown in FIG. 9*a*, the BD-121 vaccine adjuvant according to an exemplary embodiment of the present invention resulted in a significantly higher T cell-specific immune response compared to when the HBV DNA vaccine construct was administered alone. In particular, the number of the spleen immune cells reactive to the HBsAg and the HBcAg antigens was drastically increased. However, as shown in FIG. 9*b*, as a result of the analysis of the level of HBV-specific antibody production, it was confirmed that, contrary to the expectation, the BD-121 of the present invention did not increase the antibody titer compared to when the HBV DNA vaccine construct treated alone. These results confirm that selective strengthening of the T cell-specific immune response by the BD-121 of the present invention is not limited to a particular viral antigen, but it is a phenomenon that appears in a similar feature for most infectious viruses.

3-3: T Cell-Specific Immune Response and Antibody Response Against SFTS

Figure 10A:
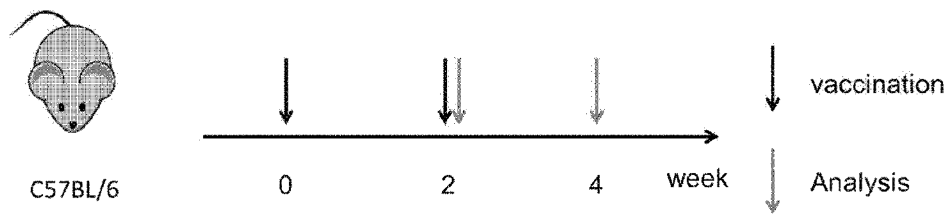
FIG. 10*a* shows the administration schedule for an SFTS DNA vaccine prepared in accordance with an exemplary embodiment and BD-121, which is a vaccine adjuvant prepared in accordance with an exemplary embodiment.

The pGX-27 (G1) was administered as an empty vector, or the SFTS DNA vaccine (12 μg) was administered alone (G2) or in combination with BD-121 (12 μg) (G3) to the femoral muscles of C57BL/6 mice twice at two-week intervals using OrbiJector® (SLVAXiGEN, Korea) by in vivo electroporation (boosting). Then, some mice were sacrificed after the 1$^{st}$ inoculation (priming) to extract spleens, and the T cell-specific immune response against the SFTS was then analyzed by the ELISPOT analysis using GnGc, NP, and NS, which are antigens of the SFTS included in the SFTS DNA vaccine, and the remaining experimental animals (n=5) were sacrificed two weeks after the 2$^{nd}$ inoculation day (boosting) to extract spleens, and the T cell-specific immune response was analyzed via ELISPOT analysis as described above (FIGS. 10*a* to 10*c*).

Figure 10B:
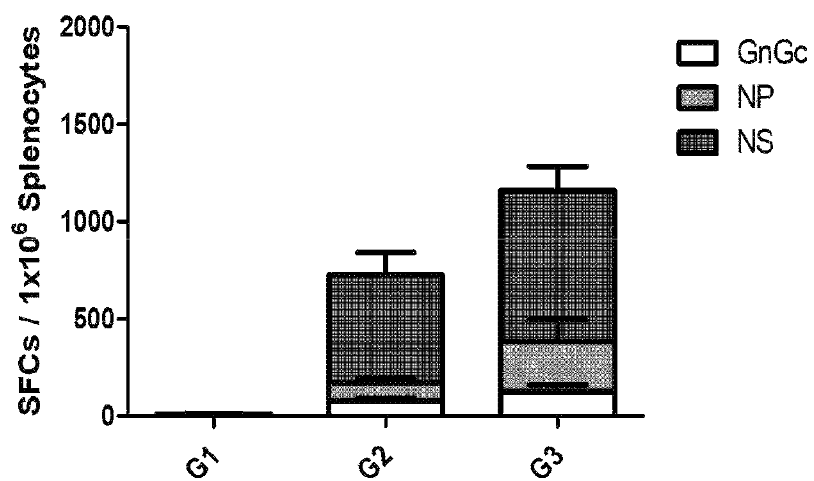
FIG. 10*b* is a graph showing the results of counting the number of spleen cells which responds in an SFTS antigen (GnGc, NP, and NS)-specific manner when an SFTS DNA vaccine prepared in accordance with an exemplary embodiment is administered alone or once in combination with BD-121, which is a vaccine adjuvant prepared in accordance with an exemplary embodiment (priming)
Figure 10C:
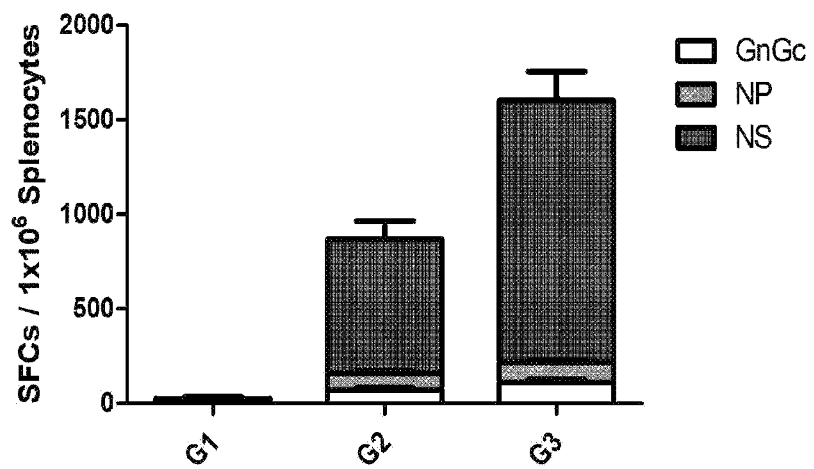
FIG. 10*c* is a graph showing the results of counting the number of spleen cells which responds in an SFTS antigen (GnGc, NP, and NS)-specific manner when an SFTS DNA vaccine prepared in accordance with an exemplary embodiment is administered alone or twice in combination with BD-121, which is a vaccine adjuvant prepared in accordance with an exemplary embodiment (priming and boosting)

As a result, as shown in FIG. 10*b*, the BD-121 vaccine adjuvant according to an exemplary embodiment of the present invention induced a significant T cell-specific immune response even based on priming alone, compared to when the SFTS DNA vaccine was treated alone, and as shown in FIG. 10*c*, the T cell-specific immune response was further increased at the time of boosting. Meanwhile, when the SFTS DNA vaccine was administered alone, no enhancement of immune responses by boosting was observed. Accordingly, it was confirmed that the BD-121 according to an exemplary embodiment of the present invention exhibits a more effective vaccine adjuvant effect when boosted by the 2$^{nd}$ inoculation as well as the priming by the 1$^{st}$ inoculation.

Then, the present inventors compared the effects of priming and boosting by varying the inoculation rate of the SFTS DNA vaccine and the BD-121 vaccine adjuvant according to an exemplary embodiment of the present disclosure.

Specifically, an empty vector (mock DNA, G1), an SFTS DNA vaccine alone (G2), a vaccine where the amount of SFTS DNA vaccine:BD-121 is 1:0.3 (G3), a vaccine where the amount of SFTS DNA vaccine:BD-121 is 1:1 (G4), and a vaccine where the amount of SFTS DNA vaccine:BD-121 is 1:3 (G5) were administered to the femoral muscles of C57BL/6 mice twice at two-week intervals using OrbiJector® (SLVAXiGEN, Korea) by in vivo electroporation (boosting), respectively. Then, some mice were sacrificed after the 1$^{st}$ inoculation (priming) to extract spleens, and the T cell-specific immune response against the SFTS was then analyzed by the ELISPOT analysis using GnGc, NP, and NS, which are antigens of the SFTS included in the SFTS DNA vaccine, and the remaining experimental animals (n=5) were sacrificed two weeks after the 2$^{nd}$ inoculation (boosting) to extract spleens, and the SFTS-specific antibody response was analyzed via ELISPOT analysis by obtaining blood plasma (Table 3, FIGS. 11*a* and 11*b*).

TABLE 3

Outline of BD-121 dose change experiment for SFTS DNA vaccine

| Experimental Group | No. of Heads for Experiment | DNA Construct for Administration | Administration Route |
|---|---|---|---|
| G1 | 3 | Mock DNA | Intramuscular Electroporation |
| G2 | 5 | SFTS DNA vaccine | |
| G3 | 5 | SFTS DNA vaccine + BD-121 (1:0.3) | |
| G4 | 5 | SFTS DNA vaccine + BD-121 (1:1) | |
| G5 | 5 | SFTS DNA vaccine + BD-121 (1:3) | |

Figure 11A:
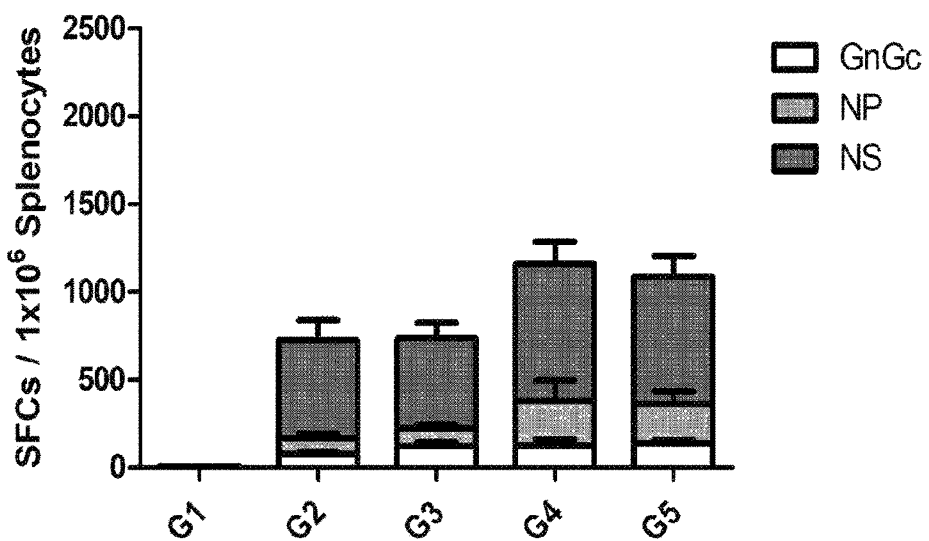
FIG. 11*a* is a graph showing the results of counting the number of spleen cells which responds in an SFTS antigen (GnGc, NP, and NS)-specific manner when an SFTS DNA vaccine prepared in accordance with an exemplary embodiment is administered alone or once in combination with BD-121, by varying a mixing ratio, which is a vaccine adjuvant prepared in accordance with an exemplary embodiment (priming)
Figure 11B:
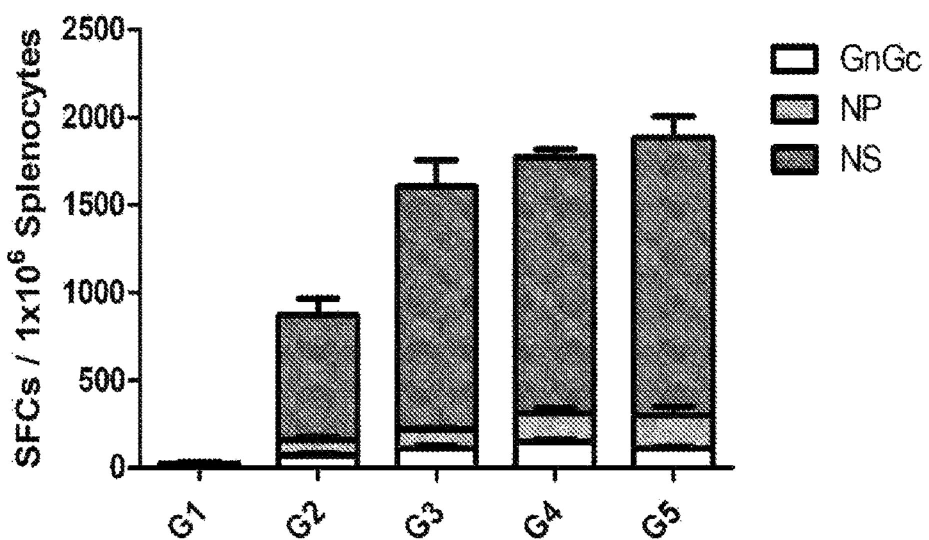
FIG. 11*b* is a graph showing the results of counting the number of spleen cells which responds in an SFTS antigen (GnGc, NP, and NS)-specific manner when an SFTS DNA vaccine prepared in accordance with an exemplary embodiment is administered alone or twice in combination with BD-121, by varying a mixing ratio, which is a vaccine adjuvant prepared in accordance with an exemplary embodiment (priming and boosting)

As a result, as shown in FIG. 11*a*, there was no significant change caused by priming between the group administered with the SFTS DNA vaccine alone and the group administered with a vaccine (where the SFTS DNA vaccine and the BD-121 according to an exemplary embodiment of the present invention were mixed in a ratio of 1:0.3). However, the experimental group where the dose ratio was increased to 1:1 showed a distinct increase in the effect of the T cell-specific immune response. Meanwhile, in the case of boosting, as shown in FIG. 11*b*, it was confirmed that there was a significant increase of the T cell-specific immune response compared to the group administered with SFTS alone, even when the dose ratio was 1:0.3. These results suggest that the BD-121 vaccine adjuvant can improve the T cell-specific immune response in a dose-dependent manner.

3-4: T Cell Specific Immune Response Against HSV-2

The present inventors examined whether the BD-121A prepared according to an exemplary embodiment of the present invention can enhance the T cell-specific immune response when the HSV-2 DNA vaccine construct prepared in Example 8 was administered.

Specifically, the experimental animals were divided into a group administered with an empty vector (pGX-27) (n=10); a group administered with the BD-02B (0.49 μg) and the BD-02C (0.49 μg) prepared in Example 8 (n=11); a group administered with the BD-02B (1.4 μg) and the BD-02C (1.4 μg) prepared in Example 8 (n=9); a group administered with the BD-02B (0.49 μg), the BD-02C (0.49 μg), and the BD121A (0.49 μg) (n=11); and a group administered with the BD-02B (1.4 μg), the BD-02C (1.4 μg), and the BD121A (1.4 μg) prepared in Example 8 (n=10), and were administered to the femoral muscles of C57BL/6 mice twice at two-week intervals using OrbiJector® (SLVAXiGEN, Korea) by in vivo electroporation (priming and boosting)). Then, after one week of the boosting, Depo-provera (2 mg) was administered to adjust the sexual hormone cycle between female mice, and infected with HSV-2 two weeks after the boosting, and the pathological scores and survival rates of the experimental animals over time were then analyzed (FIGS. 12*a* to 12*c*).

As a result, as shown in FIG. 12*b*, the pathological scores of the experimental group, in which the BD121A according to an exemplary embodiment of the present invention was co-administered, were lower than those in the group in which the BD-02 was administered alone, and such a phenomenon was shown to be dose-dependent. Furthermore, as a result of the analysis of survival rates, as shown in FIG. 12*c*, the group in which the BD-02 was administered alone showed an increase in the survival rates in a dose-dependent manner, compared to the control group, whereas the group (BD02 DP) in which the BD-121A according to an exemplary embodiment of the present invention was co-administered, the survival rates of experimental animals increased significantly. In particular, in the group where the BD-02 and BD-121A (BD02 DP) were administered in an amount of 1.4 μg, respectively, no dead animal was observed even after 18 days of infection.

Figure 13A:
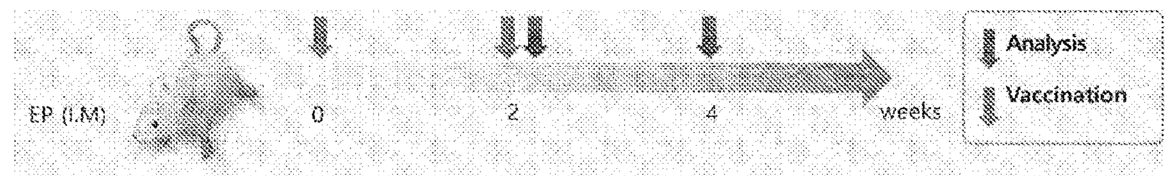
FIG. 13*a* is a schematic diagram showing the administration schedule for experimental animals, in which a HSV-2 DNA vaccine (BD02) prepared in accordance with an exemplary embodiment and BD-121, which is a vaccine adjuvant prepared in accordance with an exemplary embodiment (BD02 DP), are administered by adjusting the doses.

Then, to confirm the optimal mixing ratio between BD-02 and BD-121A, the present inventors adjusted the BD-02 and the BD-121A at various ratios (BD-02B:BD-02C:BD121A=2:2:0.2, 2:2:0.6, 2:2:2, and n=5+5 per group) and inoculated into the femoral muscle of C57BL/6 mice twice at two-week intervals using OrbiJector® (SLVAXiGEN, Korea) by in vivo electroporation (priming and boosting). Then, 5 mice in each group were sacrificed two weeks after the priming while the remaining 5 mice in each group were sacrificed two weeks after the boosting. Then, spleens were extracted therefrom and the number of spleen immune cells reactive to various HSV-2 antigens included in the BD-02 was counted by the ELISPOT analysis (Table 4, and FIGS. 13*a* and 13*b*).

TABLE 4

Outline of BD-121 dose change experiment for HSV-2 DNA vaccine

| Experimental Group | No. of Heads | DNA construct for Administration | Administration Route |
|---|---|---|---|
| 1 | 5 + 5 | BD-121A (6 μg) | Intramuscular Electroporation |
| 2 | 5 + 5 | BD-02B (2 μg) + BD-02C (2 μg) + BD-121A (0.2 μg) | Intramuscular Electroporation |
| 3 | 5 + 5 | BD-02B (2 μg) + BD-02C (2 μg) + BD-121A (0.6 μg) | Intramuscular Electroporation |
| 4 | 5 + 5 | BD-02B (2 μg) + BD-02C (2 μg) + BD-121A (2 μg) | Intramuscular Electroporation |

Figure 13B:
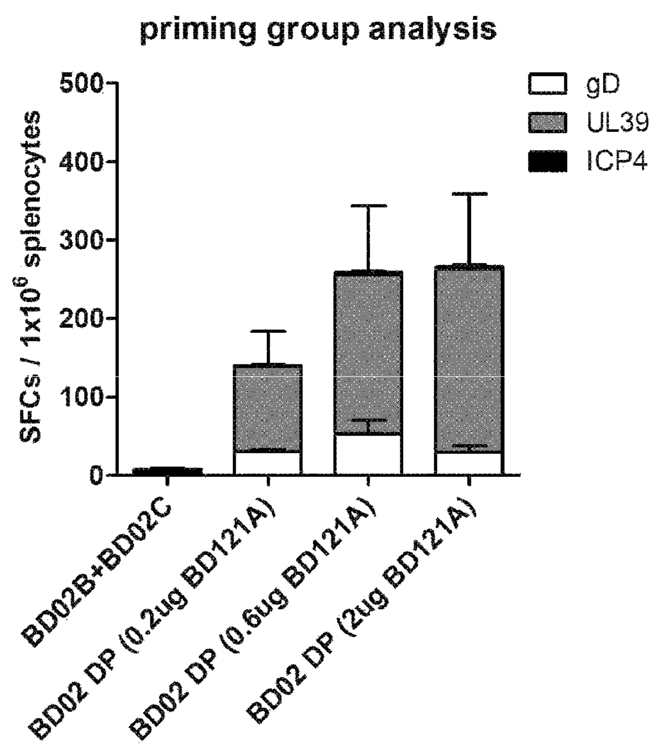
FIG. 13*b* is a graph showing the results of recording the number of spleen cells which responds in a HSV-2 antigen (gD, UL39, and ICP4)-specific manner according to the dose of a vaccine adjuvant in experimental animals, where the experimental animals are subjected to primary inoculation (priming) with a HSV-2 DNA vaccine (BD02) prepared in accordance with an exemplary embodiment and BD-121, which is a vaccine adjuvant prepared in accordance with an exemplary embodiment (BD02 DP), by adjusting the doses.

As a result, as shown in FIG. 13*b*, in the experimental group (BD-02B+BD-02C) where the BD-02 was administered alone, no T cell-specific immune response was observed two weeks after the priming. Meanwhile, in the group (BD02 DP) where the BD121A according to an exemplary embodiment of the present invention was co-administered, the T cell-specific immune response in a BD121A concentration-dependent manner was confirmed up to the ratio of 1:1:0.6. At higher doses, however, no further increase in the T cell-specific immune response was observed. Accordingly, in the BD-02 and BD121A vaccine composition according to an exemplary embodiment of the present disclosure, it was confirmed that a significant immunostimulating effect was shown even at a mixing ratio (BD-02B:BD-02C:BD121A=2:2:0.6).

3-5: Analysis of T Cell-Specific Immune Response Against HPV

The present inventors examined whether the BD-121 can enhance a T cell-specific immune response using DNA vaccine constructs of 2-valent HPV types 16 and 18 described in KR Patent Laid-open Publication No. 10-2017-0045254.

Specifically, C57BL/6 mice (experimental animals) were divided into a group administered with an empty vector (administration of pGX-27, n=10), a group administered with the 2-valent HPV DNA vaccine construct alone (n=10), a group administered with the 2-valent HPV DNA vaccine construct (8 μg)+BD-121 (1 μg) (n=10), and a group administered with the 2-valent HPV DNA vaccine construct (8 μg)+BD-121 (3 μg) (n=10). Then, two weeks after the 1st vaccine administration (priming), a half of the experimental animals (per each experimental group, n=5) were sacrificed and the spleens were extracted and used for the analysis of the T cell-specific immune response according to the priming while the remaining half (per each experimental group, n=5) were subjected to the 2nd inoculation (boosting) two weeks after the priming, and likewise, the remaining half were sacrificed two weeks after the boosting and the spleens were extracted and the T cell-specific immune response was analyzed by a method of counting the number of spleen immune cells which are specifically reactive to antigens by the ELISPOT analysis (FIG. 14).

Figure 14:
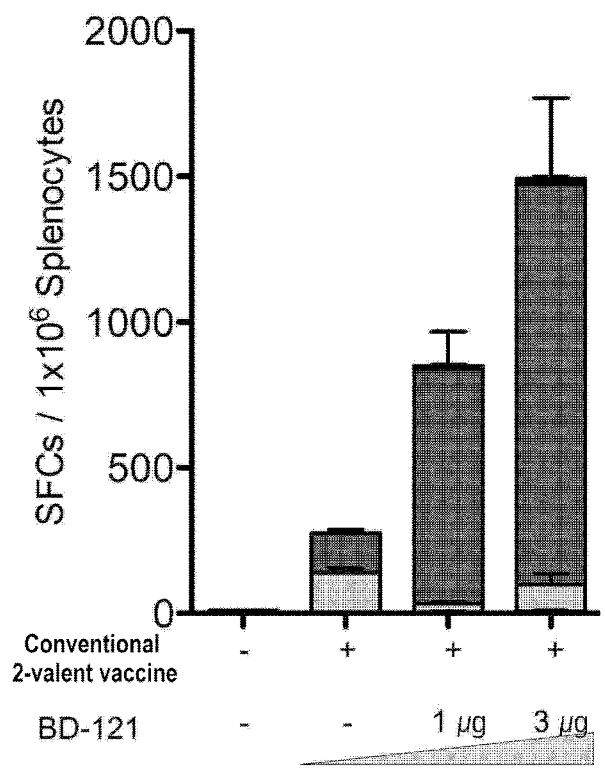
FIG. 14 is a graph showing the results of analysis of the effect of improving T cell-specific immune responses by BD-121, which is a vaccine adjuvant in accordance with an exemplary embodiment, for a conventional 2-valent HPV DNA vaccine, obtained by counting the number of spleen cells which responds in an antigen-specific manner.

As a result, as shown in FIG. 14, the T cell-specific immune response was negligible when the 2-valent HPV DNA vaccine construct was administered alone, whereas when the BD-121 according to an exemplary embodiment of the present invention was administered, the T cell-specific immune response which is concentration-dependent was enhanced.

Then, the present inventors, in order to confirm the performance of the BD-121 and the BD-121A, as vaccine adjuvants, for the HPV 14 DNA vaccine (BD-14A) which was prepared according to an exemplary embodiment of the present disclosure, administered the BD-14s (BD-14A, BD-14B, and BD-14C), which were prepared in Example 5, alone or in combination with BD-121A and then analyzed the results (Table 5.

TABLE 5

Outline of effect analysis experiment of various vaccine adjuvants against 14-valent HPV DNA vaccine

| Experimental Group | DNA construct for Administration | Administration Dose | Administration Route |
|---|---|---|---|
| 1 | Mock | — | Intermuscular Electroporation |
| 2 | BD-14 | 2 μg | |
| 3 | BD-14 + Mip-1α | 2 μg + 2 μg | |
| 4 | BD-14 + IL-12/IL-21 | 2 μg + 2 μg | |
| 5 | BD-14 + IL-12/IL-21 + Mip-1α | 2 μg + 2 μg + 2 μg | |

Figure 15A:
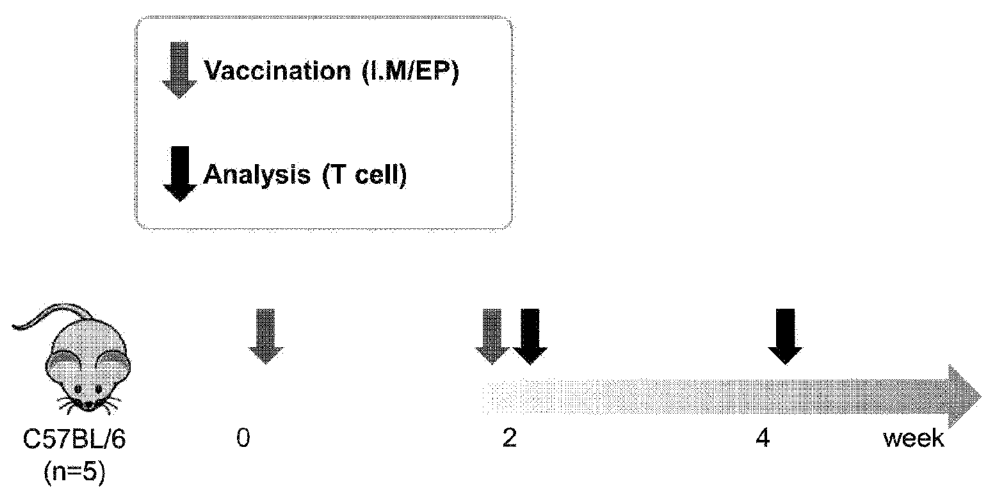
FIG. 15*a* shows the administration schedule for a 14-valent HPV DNA vaccine prepared in accordance with an exemplary embodiment and BD-121 or BD-121A, which is a vaccine adjuvant prepared in accordance with an exemplary embodiment.

Specifically, C57BL/6 mice (i.e., experimental animals) were divided into a group administered with an empty vector (n=10), a group administered with BD-14 (2 μg) (n=10), a group administered with BD-14 (2 μg)+MIP-1α (2 μg) (n=10), a group administered with BD-14 (2 μg)+BD-121 (2 μg) (n=10), and a group administered with BD-14 (2 μg)+BD-121 (2 μg)+Mip-1α (2 μg) (n=10). Then, two weeks after the 1st vaccine administration (priming), a half of the experimental animals (per each experimental group, n=5) were sacrificed and the spleens were extracted and used for the analysis of the T cell-specific immune response according to the priming while the remaining half (per each experimental group, n=5) were subjected to the 2nd inoculation (boosting) two weeks after the priming, and likewise, the remaining half of the experimental animals were sacrificed two weeks after the boosting and the spleens were extracted and the T cell-specific immune response was then analyzed by a method of counting the number of spleen immune cells which are specifically reactive to antigens by the ELISPOT analysis (FIGS. 15*a* and 15*b*).

Figure 15B:
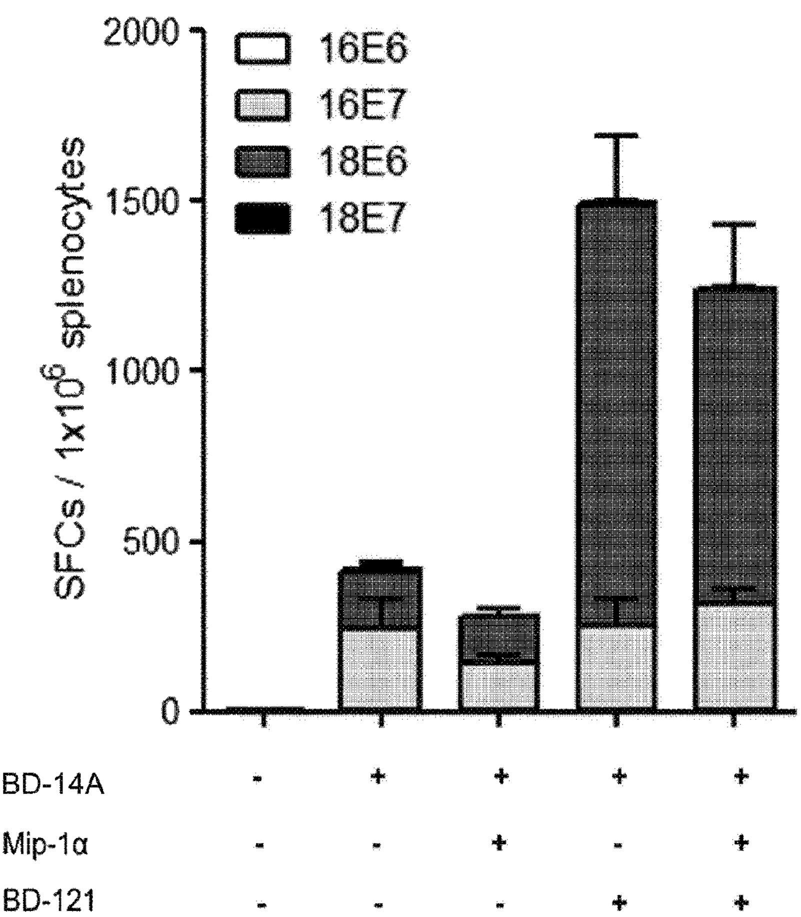
FIG. 15*b* is a graph showing the results of analysis of the effect of improving T cell-specific immune responses by BD-121 and BD-121A, which are vaccine adjuvants in accordance with an exemplary embodiment, for a 14-valent HPV DNA vaccine prepared in accordance with an exemplary embodiment, obtained by counting the number of spleen cells which responds in an antigen-specific manner.

As a result, as shown in FIG. 15*b*, both BD-121 and BD-121A significantly enhanced the T cell-specific immune response compared to the group administered with BD-10A alone and the group co-administered with BD-10A and MIP-1α.

Experimental Example 4

Preclinical Analysis

From the results of Example 3, the present inventors confirmed that the BD-121 according to an exemplary embodiment of the present invention can enhance a T cell-specific immune response against various virus antigens without much effect on antibody production. In this regard, the present inventors examined whether the BD-121 can alleviate pathological symptoms due to virus infection compared to the administration of a DNA vaccine alone, even in preclinical studies using a real animal model.

Figure 16A:
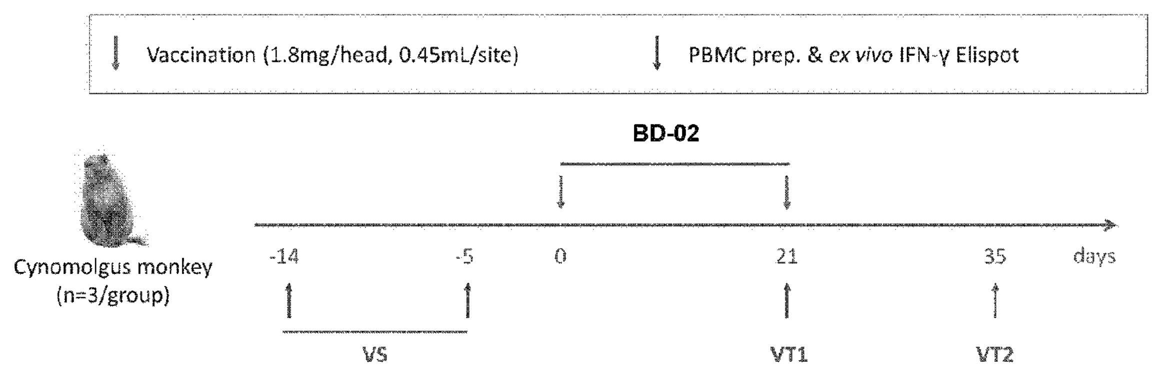
FIG. 16*a* shows the administration schedule in preclinical experiments for the analysis of the effect of a HSV-2 DNA vaccine (BD-02) in accordance with an exemplary embodiment and BD-121A, which is a vaccine adjuvant in accordance with an exemplary embodiment in cynomolgus monkeys, which are experimental animals.

Specifically, as experimental animals, three cynomolgus monkeys were used per each experimental group, and the administration groups were divided into a group administered with BD-02 alone and a group co-administered with BD-121A. Each group was administered twice at intervals of three weeks with 1.8 mg of DNA via the muscular route by electroporation, and evaluation of immune responses specific for BD-02 was performed at a time point before the administration (VS, day −14 and day −5), a time point after the 1$^{st}$ administration (VT1, day 21), and a time point after the 2$^{nd}$ administration (VT2, day 35) (FIG. 16*a*). At each time point, the separated peripheral blood mononuclear cells (PBMCs) were stimulated with a peptide pool for HSV-2 gD and UL39 antigens, which are antigens included in BD-02, and those cells which exhibited specific responses were evaluated via the ex vivo ELIPOST analysis method and indicated them as spot forming cells (SFCs).

Figure 16B:
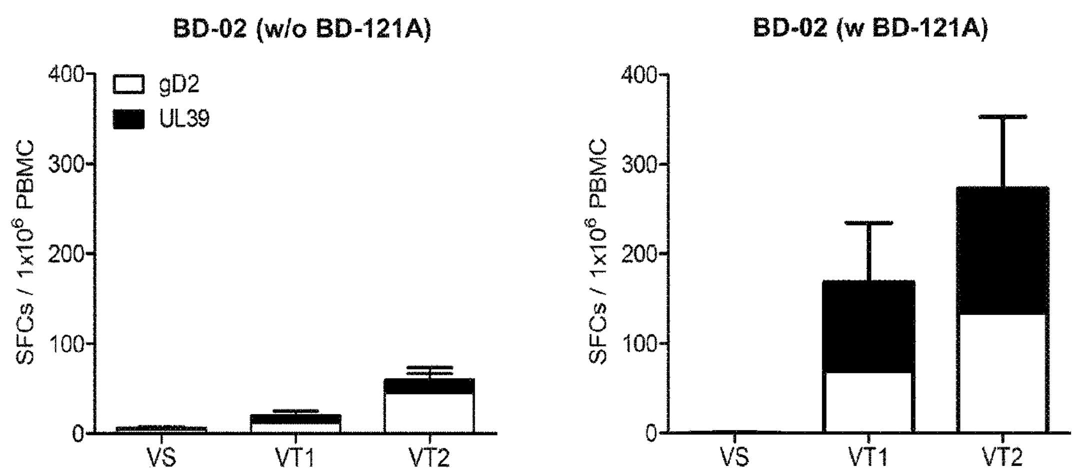
FIG. 16*b* is graphs showing the results of counting the number of spleen cells which responds in a HSV-2 antigen (gD2 and UL39)-specific manner in a group where BD-02 is administered alone (left) without a vaccine adjuvant in accordance with an exemplary embodiment and a group where BD-02 is administered in combination with BD-121A (right), pre-administration (VS), one administration (VT1), and two administrations (VT2).

As a result, as shown in FIG. 16*b*, it was confirmed that the BD-02-specific immune response was not observed at the time point before the administration, but the BD-02-specific immune response was increased after the administration in a dose frequency dependent manner. In particular, it was confirmed that the BD-02-specific immune response was significantly increased by the co-administration with BD-121A compared to the group administered with BD-02 alone, and it was observed that the difference became greater with the increase/decrease of the administration frequency.

As described above, it was confirmed that the BD-121 and the BD-121A according to an exemplary embodiment of the present invention can drastically enhance T cell-specific immune responses against various virus antigens from various virus infections, without much effect of antibody production. Accordingly, since the BD-121 and the BD-121A according to an exemplary embodiment of the present invention can drastically enhance T cell-specific immune responses which selectively increases T cells that react specifically to antigens without affecting antibody production, the BD-121 and the BD-121A according to an exemplary embodiment of the present invention can be used as an immunotherapeutic agent via cancer cell-mediated immunity enhancement for cancers (e.g., cervical cancer) as well as prevention and treatment of various infectious viruses. For example, in the case of antitumor immunotherapy responses, antibody responses is known to have little therapeutic effect on tumor cells or tumor-associated antigens, it is very important to effectively increase T cell responses specific for tumor cells or tumor-associated antigens. Even in the therapeutic immune response for the infections of viruses, such as HSV-2 or HPV, it is very important to effectively increase a T cell response because the T cell response, not the antibody response, plays a crucial role. For these reasons, the application of the BD-121 and the BD-121A, which can selectively improve only T cell responses that are specific for antigens or vaccines, has an advantage in that it can be led to the development of novel therapeutic agents for various diseases mentioned above.

Although a novel vaccine adjuvant has been described with reference to the specific embodiments, they are for illustrative purposes only. Therefore, it will be understood by those skilled in the art that various modifications and changes can be made thereto without departing from the spirit and scope of the present invention defined by the appended claims. Hence, the real protective scope of the present invention shall be determined by the technical scope of the accompanying claims.

INDUSTRIAL APPLICABILITY

The immune adjuvant according to an embodiment of the present invention may be usefully used as an immunotherapeutic agent through cellular immune enhancement of cancer, such as cervical cancer, as well as prevention and treatment of infection by various infectious viruses.

Sequence Listing Free Text

SEQ ID NO: 1 is the amino acid sequence of human IL-12p35 polypeptide.

SEQ ID NO: 2 is the amino acid sequence of a human IL-12p40 polypeptide.

SEQ ID NO: 3 is the amino acid sequence of a human IL-21 polypeptide.

SEQ ID NO: 4 is a nucleic acid sequence of a polynucleotide encoding the human IL-12p35 polypeptide.

SEQ ID NO: 5 is a nucleic acid sequence of a polynucleotide encoding the human IL-12p40 polypeptide.

SEQ ID NO: 6 is the nucleic acid sequence of the EMCV-derived internal ribosome entry site.

SEQ ID NO: 7 is the nucleic acid sequence of the RSV promoter.

SEQ ID NO: 8 is a nucleic acid sequence of a polynucleotide encoding the human IL-12 polypeptide.

SEQ ID NO: 9 is the nucleic acid sequence of the human EF-1α promoter.

SEQ ID NO: 10 is the amino acid sequence of a human MIP-1α polypeptide.

SEQ ID NO: 11 is a nucleic acid sequence of a polynucleotide encoding the human MIP-1α polypeptide.

SEQ ID NO: 12 is the amino acid sequence of the mouse IL-12p35 polypeptide.

SEQ ID NO: 13 is the amino acid sequence of a mouse IL-12p40 polypeptide.

SEQ ID NO: 14 is a nucleic acid sequence of a polynucleotide encoding the mouse IL-12p35 polypeptide.

SEQ ID NO: 15 is a nucleic acid sequence of a polynucleotide encoding the mouse IL-12p40 polypeptide.

SEQ ID NO: 16 is the amino acid sequence of a mouse IL-21 polypeptide.

SEQ ID NO: 17 is a nucleic acid sequence of a polynucleotide encoding the mouse IL-21 polypeptide.

SEQ ID NO: 18 is the amino acid sequence of a mouse MIP-1α polypeptide.

SEQ ID NO: 19 is a nucleic acid sequence of a polynucleotide encoding the mouse MIP-1α polypeptide.

SEQ ID NO: 20 is the amino acid sequence of the (GS)5 linker peptide.

SEQ ID NO: 21 is the nucleic acid sequence of a polynucleotide encoding the (GS)5 linker peptide.

SEQ ID NO: 22 is the amino acid sequence of the tPA leader peptide.

SEQ ID NO: 23 is a nucleic acid sequence of a polynucleotide encoding the tPA leader peptide.

SEQ ID NO: 24 is the amino acid sequence of the Flt3L polypeptide whose signal sequence is truncated.

SEQ ID NO: 25 is a nucleic acid sequence of a polynucleotide encoding the Flt3L polypeptide.

SEQ ID NOs: 26, 28 and 30 are amino acid sequences of shuffled antigen fusion proteins included in a DNA vaccine construct according to an embodiment of the present invention, respectively.

SEQ ID NOs: 27, 29, and 31 are nucleic acid sequences of polynucleotides encoding the shuffled antigen complexes, respectively.

SEQ ID NO: 32 is the amino acid sequence of the UL39-N1 polypeptide.

SEQ ID NO: 33 is the amino acid sequence of the UL39-C2 polypeptide.

SEQ ID NO: 34 is the amino acid sequence of the UL39-N2 polypeptide.

SEQ ID NO: 35 is the amino acid sequence of the UL39-N4-C1 polypeptide.

SEQ ID NO: 36 is the amino acid sequence of the UL39-N3 polypeptide.

SEQ ID NO: 37 is the amino acid sequence of the shuffled UL39 antigen protein sequentially linked by UL39-N1, UL39-C2, UL39-N2, UL39-N4-C1, and UL39-N3.

SEQ ID NO: 39 is the amino acid sequence of the HSV-2 glycoprotein D (gD) with the signal sequence and transmembrane domain removed.

SEQ ID NO: 40 is the amino acid sequence of the ICP0 protein from which the nuclear positioning sequence has been removed.

SEQ ID NO: 41 is the amino acid sequence of the ICP4 protein from which the RS1.3 portion has been removed.

SEQ ID NO: 42 is the amino acid sequence of the tPA-Flt3L-gD-ICP0-ICP4 fusion protein.

SEQ ID NO: 43 is a nucleic acid sequence of a polynucleotide encoding the fusion protein of SEQ ID NO: 42.

SEQ ID NO: 44 is the amino acid sequence of the antigen GnGc protein of SFTS.

SEQ ID NO: 45 is the amino acid sequence of the NP protein of SFTS.

SEQ ID NO: 46 is the amino acid sequence of the NS protein of SFTS.

SEQ ID NOs: 47 to 49 are nucleic acid sequences of polynucleotides encoding the GnGc, NP and NS proteins, respectively.

SEQ ID NOs: 50 to 68 are amino acid sequences of various linker peptides that can be used in the present invention.

What is claimed is:

1. A adjuvant composition for stimulating a T lymphocyte-specific immune response, comprising a polynucleotide encoding a p35 chain of IL-12 protein (IL-12p35), a polynucleotide encoding a p40 chain of IL-12 protein (IL-12p40) and a polynucleotide encoding an IL-21 protein as active ingredients,
   wherein the adjuvant composition induces a lower antibody response compared to where a vaccine is treated alone;
   wherein an internal ribosome entry site (IRES) links between at least two of the polynucleotides that encode the IL-12p35, IL-12p40, and IL-21 protein, respectively, and
   wherein the adjuvant composition is formulated in a form suitable for administration via intramuscular injection, intravenous injection or electroporation.

2. The adjuvant composition of claim 1, wherein the vaccine adjuvant composition comprises:
   a composition comprising one to three vectors, each of which comprises: polynucleotides that respectively encode the IL-12p35 and the IL-12p40; and a polynucleotide that encodes the IL-21 protein; or
   a composition comprising mRNA molecules, each of which encodes the IL-12p35, IL-12p40, and IL-21 proteins.

3. The adjuvant composition of claim 1, wherein the IL-12p35 is a human IL-12p35 consisting of the amino acid sequence of SEQ ID NO: 1.

4. The vaccine adjuvant composition of claim 1, wherein the IL-12p40 is a human IL-12p40 consisting of the amino acid sequence of SEQ ID NO: 2.

5. The adjuvant composition of claim 1, wherein the IL-21 protein is a human IL-21 consisting of the amino acid sequence of SEQ ID NO: 3.

6. The adjuvant composition of claim 1, further comprising at least one among:
   a MIP-1α gene construct, in which a polynucleotide encoding the MIP-1α protein is operably linked to a promoter;
   a complex gene construct, in which a polynucleotide encoding the MIP-1α protein is operably linked to at least one among the IL-12p35, IL-12p40, and IL-21 proteins, by a polynucleotide encoding an internal ribosome entry site (IRES) or linker peptide; and
   a mRNA molecule encoding MIP-1α protein.

7. The adjuvant composition of claim 6, wherein the MIP-1α protein consists of the amino acid sequence of SEQ ID NO: 10.

8. The adjuvant composition of claim 6, wherein the MIP-1α gene construct is comprised in a separate expression vector or comprised in any one or more of the one to three vectors, each of which comprises: polynucleotides that respectively encode a p35 chain (IL-12p35) and a p40 chain (IL-12p40) that constitute the IL-12 protein; and a polynucleotide that encodes the IL-21 protein.

9. An immunogenic composition for inducing immune response against virus infection, comprising, as active ingredients:
   the adjuvant composition according to claim 1; and
   an antigen of infectious virus;
   a polynucleotide encoding the antigen;
   an antigen gene construct in which the polynucleotide is operably linked to a promoter; or
   an expression vector comprising the antigen gene construct.

10. The immunogenic composition of claim 9, wherein the antigen of infectious virus is an antigen of Epstein-Barr virus (EBV), hepatitis A virus (HAV), hepatitis B virus (HBV), hepatitis C virus (HCV), hepatitis D virus (HDV), hepatitis E virus (HEV), Hantaan virus, cytomegalovirus (CMV), human immunodeficiency virus (HIV), influenza virus, human papillomavirus (HPV), poliovirus, ebola virus, rotavirus, dengue virus, West Nile virus, yellow fever virus, adenovirus, Japanese encephalitis virus, BK virus, smallpox virus, Zika virus, severe fever with thrombocytopenia syndrome (SFTS) virus, or herpes simplex virus (HSV).

11. An immunogenic composition for treating cancer, comprising, as active ingredients:
   the adjuvant composition according to claim 1; and
   a cancer antigen,
   a polynucleotide encoding the cancer antigen,
   a gene construct in which the polynucleotide is operably linked to a promoter, or
   an expression vector comprising the gene construct.

12. The immunogenic composition of claim 11, wherein the cancer antigen is a human papillomavirus (HPV) antigen, a carcinoembryonic antigen, a prostate-specific membrane antigen (PSMA), Her2/neu, MUC-1, BCR/ABL, α-fetoprotein (AFP), an Epstein-Barr virus (EBV) antigen, a human hepatitis B virus (HBV) antigen, a human hepatitis C virus (HCV) antigen, cancer antigen-125 (CA-125), cancer antigen-72-4 (CA-72-4), cancer antigen-15-3 (CA-15-3), or cancer antigen-19-9 (CA-19-9).

13. A method for stimulating a T lymphocyte-specific immune response by a immunogenic composition, comprising administering, to an individual, the adjuvant composition according to claim 1, along with an immunogenic composition, or before or after the administration of the immunogenic composition, wherein the vaccine adjuvant composition induces a lower antibody response compared to when an immunogenic was treated alone.

14. The method of claim 13, wherein the adjuvant composition is administered to an individual by in vivo electroporation.

15. The method of claim 13, wherein the method selectively induces only a T lymphocyte-specific immune response without inducing a B cell-specific immune response of the individual.

* * * * *